US009988603B2

(12) United States Patent
Li et al.

(10) Patent No.: US 9,988,603 B2
(45) Date of Patent: Jun. 5, 2018

(54) LARGE SCALE GENERATION OF FUNCTIONAL MEGAKARYOCYTES AND PLATELETS FROM HUMAN EMBRYONIC STEM CELLS UNDER STROMAL-FREE CONDITIONS

(75) Inventors: Feng Li, Marlborough, MA (US); Shi-Jiang Lu, Shrewsbury, MA (US)

(73) Assignee: Stem Cell & Regenerative Medicine International, Marlborough, MA (US)

( * ) Notice: Subject to any disclaimer, the term of this patent is extended or adjusted under 35 U.S.C. 154(b) by 219 days.

(21) Appl. No.: 13/512,827

(22) PCT Filed: Dec. 3, 2010

(86) PCT No.: PCT/US2010/058990
§ 371 (c)(1),
(2), (4) Date: Aug. 29, 2012

(87) PCT Pub. No.: WO2011/069127
PCT Pub. Date: Jun. 9, 2011

(65) Prior Publication Data
US 2012/0315338 A1 Dec. 13, 2012

Related U.S. Application Data

(60) Provisional application No. 61/266,939, filed on Dec. 4, 2009, provisional application No. 61/384,165, filed on Sep. 17, 2010.

(51) Int. Cl.
*C12N 5/078* (2010.01)
(52) U.S. Cl.
CPC ........ *C12N 5/0644* (2013.01); *C12N 2500/90* (2013.01); *C12N 2501/115* (2013.01); *C12N 2501/125* (2013.01); *C12N 2501/145* (2013.01); *C12N 2501/155* (2013.01); *C12N 2501/165* (2013.01); *C12N 2501/2311* (2013.01); *C12N 2501/26* (2013.01); *C12N 2501/91* (2013.01); *C12N 2502/1394* (2013.01); *C12N 2506/02* (2013.01); *C12N 2506/45* (2013.01)

(58) Field of Classification Search
CPC ................................................... C12N 5/0644
See application file for complete search history.

(56) References Cited

U.S. PATENT DOCUMENTS

| | | | |
|---|---|---|---|
| 5,128,259 A | 7/1992 | Morgan | |
| 8,017,393 B2 | 9/2011 | Lanza et al. | |
| 9,410,123 B2 | 8/2016 | Lanza et al. | |
| 2004/0052771 A1 | 3/2004 | Lim | |
| 2004/0229350 A1 | 11/2004 | Strelchenko et al. | |
| 2005/0153443 A1 | 7/2005 | Lanza et al. | |
| 2005/0221482 A1 | 10/2005 | Burt et al. | |
| 2006/0099198 A1 | 5/2006 | Thomson et al. | |
| 2008/0014180 A1* | 1/2008 | Lanza ............... C12N 5/0647 424/93.7 |
| 2008/0057041 A1 | 3/2008 | Chung et al. | |
| 2008/0160564 A1 | 7/2008 | Rich | |
| 2009/0246875 A1 | 10/2009 | Yamanaka et al. | |
| 2009/0304646 A1 | 12/2009 | Sakurada et al. | |
| 2011/0064705 A1 | 3/2011 | Lanza et al. | |
| 2011/0086424 A1 | 4/2011 | Lanza et al. | |
| 2017/0121681 A1 | 5/2017 | Lanza et al. | |
| 2017/0152481 A1 | 6/2017 | Lanza et al. | |

FOREIGN PATENT DOCUMENTS

| | | |
|---|---|---|
| AU | 2009244236 B2 | 6/2015 |
| AU | 2009244231 B2 | 7/2015 |
| CN | 1556197 A | 12/2004 |
| CN | 101045914 A | 10/2007 |
| CN | 102083963 A | 6/2011 |
| EP | 2507359 | 10/2012 |
| EP | 2712921 A1 | 4/2014 |
| HK | 1151064 A | 1/2012 |
| HK | 1153774 A | 4/2012 |
| JP | 2011-519576 A | 7/2011 |
| JP | 2013512676 | 4/2013 |
| JP | 2015-57070 A | 3/2015 |
| JP | 2015-61539 A | 4/2015 |
| JP | 5748654 B2 | 7/2015 |
| WO | 03/046141 A2 | 6/2003 |
| WO | 2007095064 A2 | 8/2007 |
| WO | 2007120811 A2 | 10/2007 |
| WO | 2009137624 | 11/2009 |
| WO | 2009137629 A2 | 11/2009 |
| WO | 2011069127 A1 | 6/2011 |

OTHER PUBLICATIONS

Mercher et al., 2008, Cell Stem Cell, vol. 3, pp. 314-326.*
Tober et al. (2007, Blood, vol. 109(4), pp. 1433-1441).*
Lu et al. (2008, Regen. Med., vol. 3(5), pp. 693-704).*
Lowry et al. (2008, PNAS, vol. 105(8), pp. 2883-2888).*
Reubinoff et al. (2000, Nature Biotechnology, vol. 18, pp. 399-404).*
2008, Ireland KA., Visualizing Human Biology, 3rd Ed., Wiley and Sons Inc., 3 pages total.*

(Continued)

*Primary Examiner* — Thaian N Ton
*Assistant Examiner* — David A. Montanari
(74) *Attorney, Agent, or Firm* — Stephen W. Chen; Nixon Peabody LLP

(57) ABSTRACT

The present invention provides a method of generating megakaryocytes and platelets. In various embodiments, method involves the use of human embryonic stem cell derived hemangioblasts for differentiation into megakaryocytes and platelets under serum and stromal-free condition. In this system, hESCs are directed towards megakaryocytes through embryoid body formation and hemangioblast differentiation. Further provided is a method of treating a subject in need of platelet transfusion.

17 Claims, 25 Drawing Sheets

(56) References Cited

OTHER PUBLICATIONS

Reijo et al. (2009, Differentiation, vol. 78, pp. 18-23).*
Dolzhanskiy et al. (1997, Blood, vol. 89(2), pp. 426-434).*
Bhatia, M. Hematopoiesis from Human Embryonic Stem Cells. New York Academy of Sciences (2007), 1106(1): 219-222.
Cerdan et al. Hematopoietic Differentiation. Embryonic Stem Cells (2007). Chapter 5:53-83.
Kaufman et al. Hemotopoietic Colony-Forming Cells Derived from Human Embryonic Stem Cells. PNAS (2001). 98 (19):10716-10721.
Lu et al. Generation of Functional Hemangioblasts from Human Embryonic Stem Cells. Nature Methods (2007). 4 (6):501-509.
Lu et al. Recombinant HoxB4 Fusion Proteins Enhance Hematopoietic Differentiation of Human Embryonic Stem Cells. Stem Cells and Development (2007). 16:547-559.
Ma et al. Novel Method for Efficient Production of Multipotential Hematopoietic Progenitors from Human Embryonic Stem Cells. International Journal of Hematology (2007). 85:371-379.
Seliger et al. Chemical Production of Excited States. Chemiluminescence of Carcinogenic Hydrocarbons Accompanying Their Metabolic Hydroxylation and a Proposal for Common Active Site Geometrics for Hydroxylation. The Journal of Physical Chemistry (1976). 82(20):2296-2306.
Schenke-Layland et al. Reprogrammed Mouse Fibroblasts Differentiate into Cells of the Cardiovascular and Hematopoietic Lineages. Stem Cells (2008). 26:1537-1546.
Shinoda et al. a4-Integrin + Endothelium Derived from Primate Embryonic Stem Cells Generates Primitive and Definitive Hematopoietic Cells. Blood (2007). 109(6): 2406-2415.
Umeda et al. Development of Primitive and Definitive Hematopoiesis from Non-Human Primate Embryonic Stem Cells in vitro. Development and Disease (2004). 131:1869-1879.
Vodyanik et al. Human Embryonic Stem Cell-Derived CD34+ cells: Efficient Production in the Coculture with OP9 Stromal Cells and Analysis of Lymphohematopoietic Potential. Blood (2005). 105(2):617-626.
Wernig et al. In Vitro Reprogramming of Fibroblasts into a Pluripotent ES-Cell-Like State. Nature (2007). 448:318-325.
Zhao et al. Effect of Different Hemopoietic Microenvironment on the Differentiation of Hemopoietic Cells from Human Embryonic Stem Cells. J. Cent. South Univ (Med Sci). (2007). 32(6)992-996. Abstract Only.
Douay et al. Stem Cells—A source of adult red blood cells for transfusion purposes: present and future. Crit Care Clin (2009). 25:383-398.
Hematti et al. Nonhuman primate embryonic stem cells as a preclinical model for hematopoietic and vascular repair. Experimental Hematology. (2005). 33: 980-986.
Klimanskaya et al. Approaches for Derivation and Maintenance of Human ES Cells: Detailed Procedures and Alternatives. Handbook of Stem Cells. (2004). 1:437-.
Life Technologies. Guidelines for Maintaining Cultured Cells. What is Subculture? (2014). Retrieved from http://www.lifetechnologies.com/us/en/home/references/gibco-cell-culture-basics/cell-cult . . . pp. 1-4.
Qiu et al. Globin switches in yolk sac like primitive and fetal-like definitive red blood cells produced from human embryonic stem cells. Blood (2008). 111(4):2400-2408.
Rajesh et al. Differential requirements for hematopoietic commitment between human and rhesus embryonic stem cells. Stem Cells. (2007). 25:490-499.
Takahashi et al. Induction of pluripotent stem cells from adult human febroblasts by defined factors. Cell (2007). 131:1-12.
Takashi et al. Establishment of mouse embryonic stem cell-derived erythroid progenitor cell lines able to produce functional red blood cells. PLoS One (2008). 2:1-11.
Tian et al. Cytokine requirements differ for stroma and embryoid body-mediated hematopoiesis from human embryonic stem cells. Experimental Hematology (2004). 32:1000-1009.
Verfaillie et al. Kinetics of engraftment of CD34(-) and CD34(+) cells from mobilized blood differs from that of CD34. Exper Hematol (2000). 28(9): 1071-1079.
Yu et al. Pluripotent stem cell lines. Genes Dev. (2008). 22:1987-1997.
Giarratana et al. Ex vivio generation of fully mature human red blood cells from hematopoietic stem cells. Nature Biotechnology (2005). 23(1):69-74.
Li et al., In vitro differentiation into megakaryocytes and generation of platelets from CD34 cells of umbilical cord blood, J. Cent. South Univ., 2006, pp. 776-781, vol. 31(5), (abstract).
Takayama et al., Generation of functional platelets from human embryonic stem cells in vitro via ES-sacs, VEGF-promoted structures that concentrate hematopoietic progenitors, Blood, Jun. 1, 2008, pp. 5298-5306, vol. 111, No. 11, American Society of Hematology, Washington DC.
Tober et al., The megakaryocyte lineage originates from hemangioblast precursors and is an integral component both of primitive and of definitive hematopoiesis, Blood, Feb. 15, 2007, pp. 1433-1441, vol. 109, No. 4, American Society of Hematology, Washington DC.
International Search Report and Written Opinion for International Application No. PCT/US2010/058990, Apr. 4, 2011.
International Preliminary Report on Patentability for International Application No. PCT/US2010/058990, Jun. 5, 2012.
Springer et al., VEGF Gene Delivery to Muscle: Potential Role for Vasculogenesis in Adults, Molecular Cell, Nov. 1998, pp. 549-558, vol. 2.
Kennedy et al., Development of the hemangioblast defines the onset of hematopoiesis in human ES cell differentiation cultures, Blood, Apr. 1, 2007, pp. 2679-2687, vol. 9, No. 7, American Society of Hematology, Washington DC.
Life Technologies, Guidelines for Maintaining Cultured Cells, 2014, pp. 1-4, Life Technologies Corporation.
European Extended Search Report of EP 17174456.8 EP, dated Nov. 24, 2017, 11 Pages.
Extended Search Report of EP 09743610.9 dated Jan. 26, 2012, 8 pages.
Extended Search Report of EP 09743615.8, dated Jan. 26, 2012.
International Report on Patentability of PCT/US2009/043043, dated Nov. 18, 2010, 18 Pages.
International Search Report and Written Opinion of PCT/US2009/043043, dated Sep. 22, 2009, 21 Pages.
Chun et al., Megakaryocyte Production from Feeder Cell-Free Cultures of Human Embryonic Stem Cells (hESC), 2009, Blood, vol. 114: Abstract 2528.
Feng et al., Large Scale Generation of Functional Megakaryocytes from Human Embryonic Stem Cells (hESCs) under Stromal-Free Conditions, 2009, Blood, vol. 114: Abstract 2540.
Grant et al. "Adult hematopoietic stem cells provide functional hemangioblast activity during retinal neovascularization," Nature Medicine, vol. 8, No. 6, Jun. 2002; 607-612.
Huangfu et al. Induction of pluripotent stem cells from primary human fibroblasts with only Oct4 and Sox2. Nature Biotechnology (2008). 26(11):1269-1275.
Klimanskaya et al., "Approaches for Derivation and Maintenance of Human ES Cells: Detailed Procedures and Alternatives," Reference 6 from Specification-Klimanskaya and McMahon Book Chapter Stem Cells vol. 1.
Loges, et al., Identification of the adult human hemangioblast, Stem Cells and Development, Elsevier, NL, vol. 13, No. 3, Jun. 1, 2004, pp. 229-242.
Lu et al. "Biologic properties and enucleation of red blood cells from human embryonic stem cells," Blood, vol. 112, 2008; 1-10.
Lu et al. Protocol for culturing, differentiating and expanding hES-BC cells. Supplemental Protocol. Nature Methods (2007), 4, pp. 1-3.
Maherali et al. Guidelines and Techniques for the Generation of Induced Pluripotent Stem Cells. Cell Stem Cell (2008). 3:595-605.
Park et al. Reprogramming of human somatic cells to pluripotency with defined factors. Nature (2008). 451 (7175):141-146.

(56) References Cited

OTHER PUBLICATIONS

Sauvageau, Overexpression of HOXB4 in hempotopoietic cells causes the selective expanision of more primitive populations in vitro and in vivo, Genes &Development, 9:1753-1765, 1995 Cold Spring Harbor Laboratory Press.
Takahashi et al. Induction of pluripotent stem cells from adult human fibroblasts by defined factors. Cell (2007) 131 (5): 861-872.
Verfaillie et al. Kinetics of engraflment of CD34(−) and CD34 (+) cells from mobilized blood differs from that of CD34. Exper Hematol (2000) 28(9):1071-1079.
Wang et al, "Endothelial and hematopoietic cell fate of human embryonic stem cells originates from primitve endothelium with hemangioblastic properties" Immunity (2004), vol. 21, No. 1, pp. 31-41.
Xiong, Jing-Wei et al., Molecular and Developmental Biology of the Hemangioblast, Developmental Dynamics, 2008, vol. 237, pp. 1218-1231.
Zwaka, Thomas P., Chapter 4 from Regenerative Medicine. Department of Health and Human Services. Aug. 2006. </info/scireport/regenerativemedicine>, accessed on Sep. 11, 2017.
EP 13180755.4 Extended Search Report dated Mar. 3, 2014; 9 pages.
EP 10835231.1 Extended Search Report dated Apr. 14, 2015; 7 pages.
Fan et al. Megakaryocyte Production from Feeder Cell-Free Cultures of Human Embryonic Stem Cells (hESC). Blood (ASH Annual Meeting Abstracts) 2009. 114: Abstract 2528.
Li et al. Large Scale Generation of Functional Megakaryocyties from Human Embryonic Stem Cells (hESCs) Under Stromal-Free Conditions. Blood (ASH Annual Meeting Abstracts) 2009. 114: Abstract 2540.
Reems et al. In Vitro Megakaryocyte Production and Platelet Biogenesis: State of the Art. Transfusion Medicine Reviews (2010). 24(1): 33-43.

\* cited by examiner

US 9,988,603 B2

LARGE SCALE GENERATION OF FUNCTIONAL MEGAKARYOCYTES AND PLATELETS FROM HUMAN EMBRYONIC STEM CELLS UNDER STROMAL-FREE CONDITIONS

FIELD OF INVENTION

This invention relates to the production of functional megakaryocytes and platelets, and their uses thereof.

BACKGROUND

All publications herein are incorporated by reference to the same extent as if each individual publication or patent application was specifically and individually indicated to be incorporated by reference. The following description includes information that may be useful in understanding the present invention. It is not an admission that any of the information provided herein is prior art or relevant to the presently claimed invention, or that any publication specifically or implicitly referenced is prior art.

After vascular injury, platelets rapidly adhere to damaged blood vessels and trigger a complex cascade of events that result in thrombus formation. The demand lot platelet transfusions has continued to increase during the last several decades[51]. Platelets can only be stored for less than a week, creating a continuous challenge for donor dependent programs. Shortages in the supply of platelets can have potentially life-threatening consequences, especially in patients where multiple transfusions are necessary. Repeated transfusions may also lead to refractory responses that are linked to immunity mediated host reaction and may require costly patient matching[52;53]. The ability to generate patient-matched platelets in vitro would provide significant advantages in these clinical scenarios.

Limitations in the supply of platelets can have potentially life-threatening consequences for transfusion-dependent patients with unusual/rare blood types, particularly those who are alloimmunized, and patients with cancer or leukemia who, as often happens, develop platelet alloimmunity. Frequent transfusion of platelets is clinically necessary because the half-life of transfused human platelets is 4-5 days. Moreover, platelets from volunteer donor program are at the constant risk of contaminations of various pathogens. Platelets cannot be stored frozen, thus the ability to generate platelets in vitro would provide significant advances for platelet replacement therapy in clinical settings. For more than a decade, human hematopoietic stem cells (HSC, CD34+) from bone marrow (BM), cord blood (CB) or peripheral blood (PB) have been studied for megakaryocyte (MK) and platelet generation. With the combinations of cytokines, growth factors and/or stromal feeder cells, functional platelets have been produced from HSCs with significant success[1;2]. However, HSCs are still from donors and have limited expansion capacity under current culture conditions, which likely prevent the large-scale production and future clinical applications.

Human embryonic stem cells (hESC) can be propagated and expanded in vitro indefinitely, providing a potentially inexhaustible and donorless source of cells for human therapy. Differentiation of hESCs into hematopoietic cells has been extensively investigated in vitro for the past decade. The directed hematopoietic differentiation of hESCs has been successfully achieved in vitro by means of two different types of culture systems. One of these employs co-cultures of hESCs with stromal feeder cells, in serum-containing medium[3;4]. The second type of procedure employs suspension culture conditions in ultra-low cell binding plates, in the presence of cytokines with/without serum[5-7]; its endpoint is the formation of EBs. Hematopoietic precursors as well as mature, functional progenies representing erythroid, myeloid, macrophage, megakaryocytic and lymphoid lineages have been identified in both of the above differentiating hESC culture systems[3-6;8-14]. Previous studies also generated megakaryocytes/platelets from hESCs by co-culturing with stromal cells in the presence of serum[15;16]. Platelets derived from hESCs possess the potential for transfusion medicine purposes if they can be generated efficiently and in large scale. More importantly, platelets do not have a nucleus and contain only minimal genetic material, and can be irradiated before transfusion to effectively eliminate any contaminating cells, such as an undifferentiated hESC. Therefore, safety should not be an issue. However, the yield of megakaryocytes/platelets in the above studies was low[15;16]. There remains a need in the art for efficient and controlled differentiation of hESCs into homogeneous megakaryocytic populations and subsequent functional platelets.

SUMMARY OF THE INVENTION

The following embodiments and aspects thereof are described and illustrated in conjunction with compositions and methods which are meant to be exemplary and illustrative, not limiting in scope.

The present invention provides for a method of generating megakaryocytes, comprising: providing hemangioblasts; and culturing the hemangioblasts to differentiate into megakaryocytes (MKs). In certain embodiments, the hemangioblasts can be differentiated in vitro from pluripotent stem cells. In certain embodiments, the pluripotent stem cells can be human embryonic stem cells (hESCs). In certain embodiments, the pluripotent stem cells can be induced pluripotent stem cells (iPSCs). In certain embodiments, the iPSCs can be induced from somatic cells of human origin. In certain embodiments, the somatic cells can be from adult tissue. In certain embodiments, the somatic cells can be from fetal tissue. In certain embodiments, the differentiation of pluripotent stem cells can comprise dissociation of the pluripotent stem cells and culturing the pluripotent stem cells with medium comprising a growth factor or cytokine selected from the group consisting of BMP-4, VEGF, bFGF, TPO, Flt3 ligand, SCF and combinations thereof to form embryoid bodies (EBs). In certain embodiments, the medium can comprise BMP-4 and VEGF and culturing the pluripotent stem cells can be for about 48 hours to form the EBs. In certain embodiments, the concentration of BMP-4 can be 50 ng/ml and VEGF can be 50 ng/ml. In certain embodiments, the medium can be Stemline II medium.

In certain embodiments, the formed EBs can be chemically and/or mechanically dissociated and at least a portion of the culture medium can be replaced with medium comprising a growth factor or cytokine selected from the group consisting of BMP-4, VEGF, bFGF, TPO, Flt3 ligand, SCF and combinations thereof to generate the hemangioblasts. In certain embodiments, the concentration of bFGF can be 20 ng/ml, TPO can be 50-100 ng/ml, Flt3 ligand can be 50 ng/ml and SCF can be 50 ng/ml. In certain embodiments, the medium further comprises IL6, estradiol, vitamin B3, one or more extracellular matrix protein or combinations thereof. In certain embodiments, the dissociated EBs can be cultured in blast colony growth medium for about 3 to 4 days to generate the hemangioblasts.

Other embodiments of the present invention provides for a method of generating megakaryocytes, comprising: providing hemangioblasts; and culturing the hemangioblasts to differentiate into megakaryocytes (MKs). In certain embodiments, differentiation of the hemangioblasts into the MKs can comprise culturing the hemangioblasts in medium comprising a growth factor or cytokine selected from the group consisting of TPO, SCF, IL11 and combinations thereof for about 2 to 8 days. In certain embodiments, the concentration of TPO can be 50 ng/ml, SCF can be 20 ng/ml and IL11 can be 20 ng/ml. In certain embodiments, the medium can be Stemline II medium. In certain embodiments, the method can further comprise replacing at least a portion of the culture medium with medium comprising a growth factor or cytokine selected from the group consisting of TPO, SCF, IL11 and combinations thereof every 2 to 3 days to differentiate the hemangioblasts into the MKs.

The present invention also provides a method of generating platelets, comprising: providing megakaryocytes (MKs); and culturing the MKs to differentiate into platelets. In certain embodiments, the MKs can be differentiated from hemangioblasts. In certain embodiments, differentiation of the hemangioblasts into the MKs can comprise culturing the hemangioblasts in medium comprising a growth factor or cytokine selected from the group consisting of TPO, SCF, IL11 and combinations thereof for about 2 to 8 days. In certain embodiments, the concentration of TPO can be 50 ng/ml, SCF can be 20 ng/ml and IL11 can be 20 ng/ml. In certain embodiments, the medium can be Stemline II medium. In certain embodiments, the method can further comprise replacing at least a portion of the culture medium with medium comprising a growth factor or cytokine selected from the group consisting of TPO, SCF, IL11 and combinations thereof every 2 to 3 days to differentiate the hemangioblasts into the MKs.

In certain embodiments, the hemangioblasts can be differentiated in vitro from pluripotent stem cells. In certain embodiments, the pluripotent stem cells can be human embryonic stem cells (hESCs). In certain embodiments, the pluripotent stem cells can be induced pluripotent stem cells (iPSCs). In certain embodiments, iPSCs can be induced from somatic cells of human origin. In certain embodiments, the somatic cells can be from adult tissue. In certain embodiments, the somatic cells can be from fetal tissue. In certain embodiments, the differentiation of pluripotent stem cells can comprise dissociation of the pluripotent stem cells and culturing the pluripotent stem cells with medium comprising a growth factor or cytokine selected from the group consisting of BMP-4, VEGF, bFGF, TPO, Flt3 ligand, SCF and combinations thereof to form embryoid bodies (EBs). In certain embodiments, the medium can comprise BMP-4 and VEGF and culturing the pluripotent stem cells can be for about 48 hours to form the EBs. In certain embodiments, the concentration of BMP-4 can be 50 ng/ml and VEGF can be 50 ng/ml. In certain embodiments, the medium can be Stemline II medium.

In certain embodiments, the formed EBs can be chemically and/or mechanically dissociated and at least a portion of the culture medium can be replaced with medium comprising a growth factor or cytokine selected from the group consisting of BMP-4, VEGF, bFGF, TPO, Flt3 ligand, SCF and combinations thereof to generate the hemangioblasts. In certain embodiments, the concentration of bFGF can be 20 ng/ml, TPO can be 50-100 ng/ml, Flt3 ligand can be 50 ng/ml and SCF can be 50 ng/ml. In certain embodiments, the medium can further comprise IL6, estradiol, vitamin B3, one or more extracellular matrix protein or combinations thereof. In certain embodiments, the dissociated EBs can be cultured in blast colony growth medium for about 3 to 4 days to generate the hemangioblasts.

Other embodiments of the present invention provides for a method of generating platelets, comprising: providing megakaryocytes (MKs); and culturing the MKs to differentiate into platelets.

In certain embodiments, the MKs can be resuspended and cultured for at least 4 days in medium comprising a growth factor or cytokine selected from the group consisting of TPO, SCF, sodium heparin, IL11 and combinations thereof to differentiate into the platelets. In certain embodiments, the concentration of TPO can be 100 ng/ml, SCF can be 50 ng/ml, sodium heparin can be 25 units/ml, and IL11 can be 20 ng/ml. In certain embodiments, the method can further comprise an addition of GM 6001 or IL3 after the at least 4 days of culturing the MKs. In certain embodiments, the method can further comprise replacing at least a portion of the medium with medium comprising a growth factor or cytokine selected from the group consisting of TPO, SCF, sodium heparin, IL11 and combinations thereof at least every 2 days. In certain embodiments, the medium can be IMDM medium.

In certain embodiments, the MKs can be dissociated and cultured on a mitotically arrested feeder layer for at least 4 days in medium comprising a growth factor or cytokine selected from the group consisting of TPO, SCF, sodium heparin, IL11 and combinations thereof to differentiate into the platelets. In certain embodiments, the feeder layer can comprise OP9 cells. In certain embodiments, the feeder layer can comprise C3H 10T1/2 cells. In certain embodiments, the method can further comprise an addition of GM 6001 or IL3 after the at least 4 days of culturing the MKs. In certain embodiments, the method can further comprise replacing at least a portion of the medium with medium comprising a growth factor or cytokine selected from the group consisting of TPO, SCF, sodium heparin, IL11 and combinations thereof at least every 2 days. In certain embodiments, the medium can be IMDM medium.

The present invention also provides a quantity of megakaryocytes generated from any of the methods of the present invention.

The present invention also provides a quantity of platelets generated from any of the methods of the present invention. In certain embodiments, the platelets can be stored in a solution that does not contribute to an HLA alloimmunogenic response in a subject upon administration of the platelets to the subject. In certain embodiments, the platelets cannot be activated in the presence of apyrase and/or EDTA.

The present invention also provides a method of screening for a modulator of cellular differentiation comprising: providing a quantity of megakaryocytes (MKs); contacting the MKs with a test compound; determining the presence or absence of a functional effect from the contact between the MKs and the test compound; wherein the presence of a functional effect indicates that the test compound can be a megakaryopoietic, thrombopoietic, and/or hematopoietic factor that modulates cellular differentiation and the absence of a functional effect indicates that the test compound may not be a megakaryopoietic, thrombopoietic, and/or hematopoietic factor that modulates cellular differentiation. The present invention also provides a method of treating a subject in need of platelet transfusion, comprising: providing a quantity of hemangioblasts; culturing the hemangioblasts to differentiate into megakaryocytes (MKs); culturing the MKs in vitro to differentiate into platelets; providing a quantity of the in vitro differentiated platelets; and administering the quantity of the in vitro differentiated platelets to the subject in need of the platelet transfusion, thereby treating the subject in need of platelet transfusion. In certain embodiments, the in vitro differentiated platelets can be matched to the subject to reduce or eliminate an immunity mediated host reaction.

Other features and advantages of the invention will become apparent from the following detailed description, taken in conjunction with the accompanying drawings, which illustrate, by way of example, various features of embodiments of the invention.

BRIEF DESCRIPTION OF THE FIGURES

Exemplary embodiments are illustrated in referenced figures. It is intended that the embodiments and figures disclosed herein are to be considered illustrative rather than restrictive.

DESCRIPTION OF THE INVENTION

Figure 1:
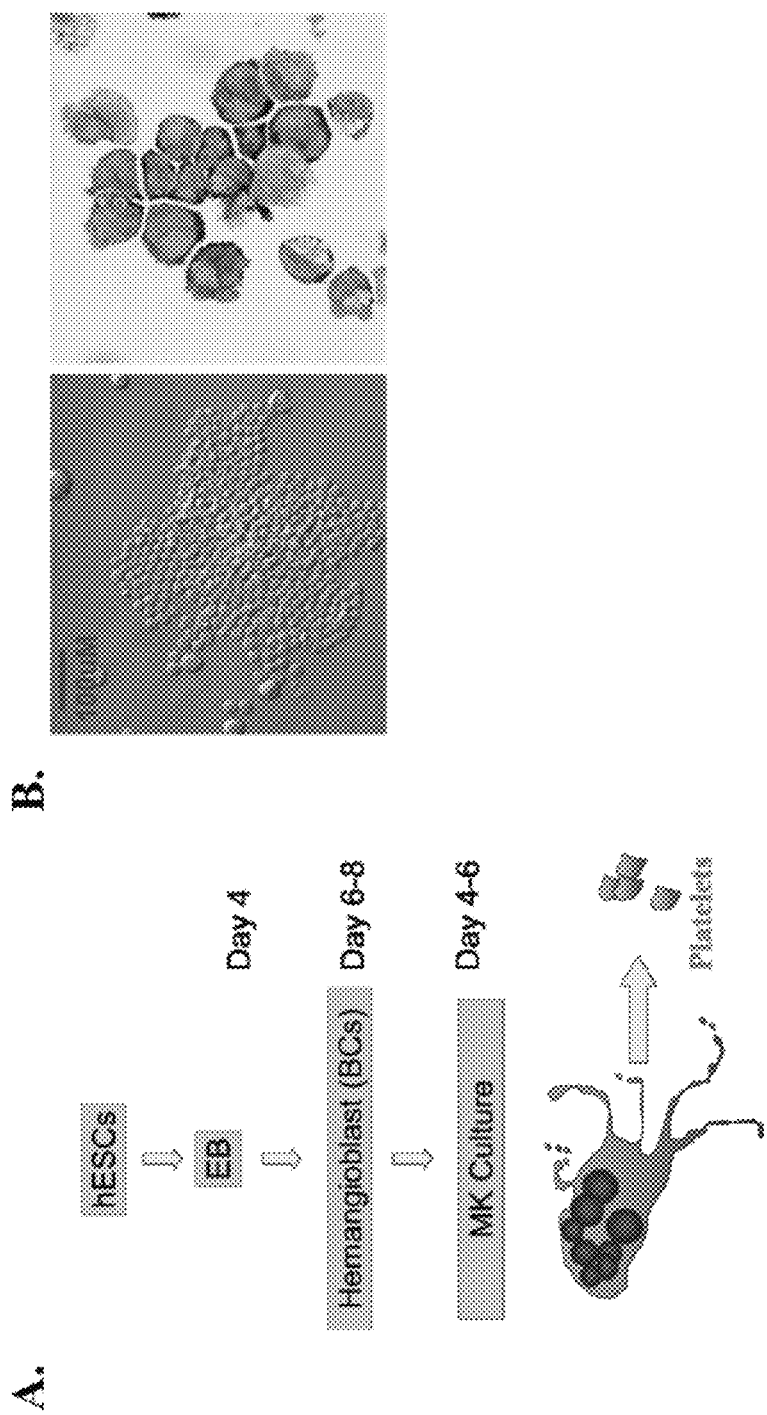
FIG. 1 depicts hESC derived blast cells generate megakaryocyte progenitors in accordance with various embodiments of the present invention. A. Flow chart of generating megakaryocytes from hESCs under serum and stromal free conditions. As described previously, hESCs were cultured in suspension to give rise EBs. EBs were harvested on day 4 and dissociated with trypsin into single cells prior to methylcellulose based semi-solid hemangioblast cultures. Blast cells were harvested from day 6 to day 8 cultures for MK cultures which then produced mature megakaryocytes in the next 4 to 6 days in suspension. B. Representative images of day 6 blast colony (Phase contrast, left) and blast cells (Giemsa staining, right). C. Bar graphs show the CFU-MK colony assays for HUES3 and H1 hESC derived BCs. D. Microscopic image shows a CD41 stained CFU-MK colony generated from H1 hESC derived BCs. The insert shows cellular processes from megakaryocytes. E. FACS analyses show differences in the percentages of CD41a+ cells in blast cultures from three different hESC HUES3, MA01 and MA09.
Figure 1:
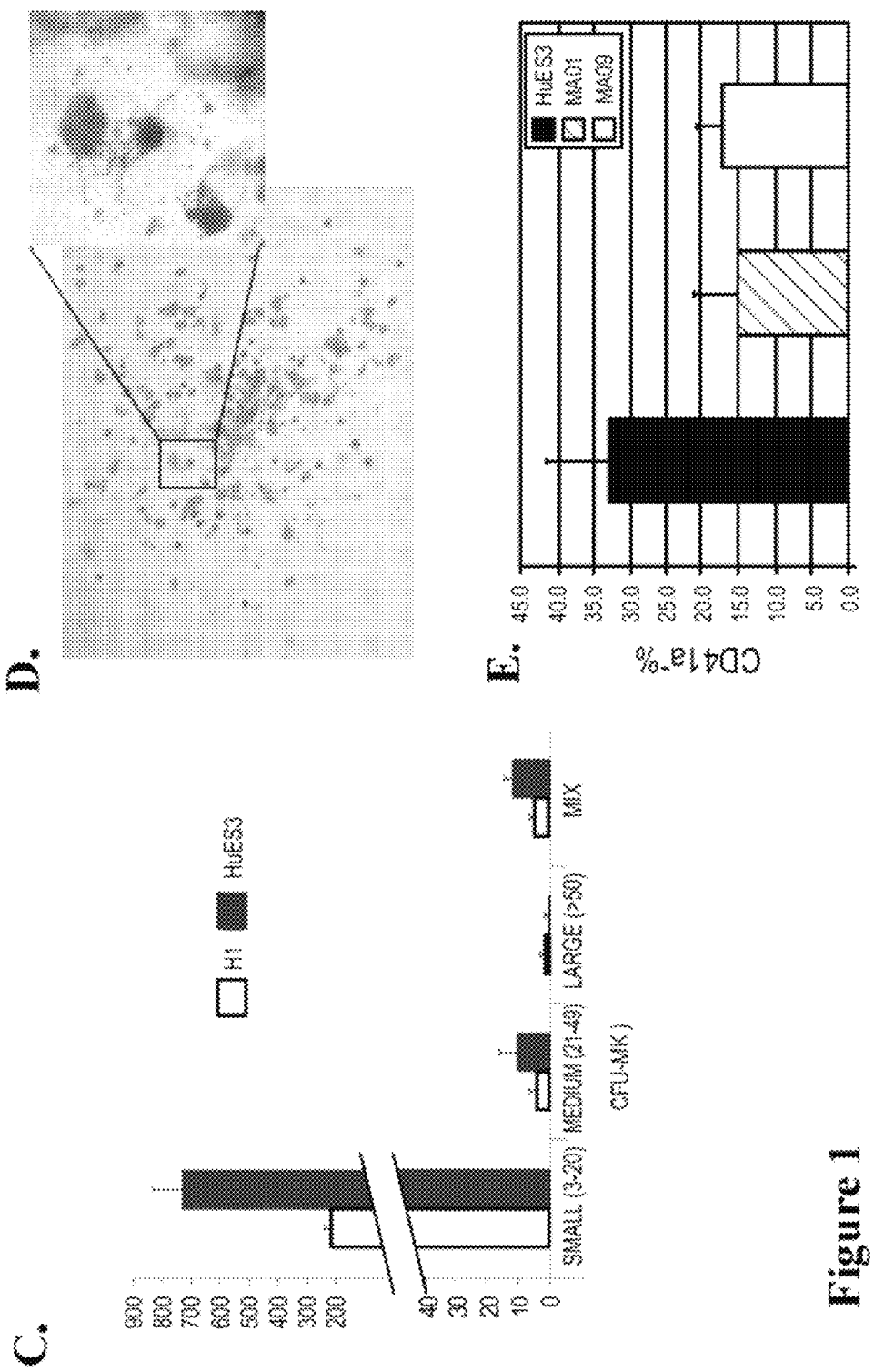

All references cited herein are incorporated by reference in their entirety as though fully set forth. Unless defined otherwise, technical and scientific terms used herein have the same meaning as commonly understood by one of ordinary skill in the art to which this invention belongs. Singleton et al., *Dictionary of Microbiology and Molecular Biology* 3rd ed., J. Wiley & Sons (New York, N.Y. 2001); March, *Advanced Organic Chemistry Reactions, Mechanisms and Structure* 5$^{th}$ ed., J. Wiley & Sons (New York, N.Y. 2001); and Sambrook and Russel, *Molecular Cloning: A Laboratory Manual* 3rd ed., Cold Spring Harbor Laboratory Press (Cold Spring Harbor, N.Y. 2001), provide one skilled in the art with a general guide to many of the terms used in the present application.

One skilled in the art will recognize many methods and materials similar or equivalent to those described herein, which could be used in the practice of the present invention. Indeed, the present invention is in no way limited to the methods and materials described. For purposes of the present invention, the following terms are defined below.

As used in the description herein and throughout the claims that follow, the meaning of "a," "an," and "the" includes plural reference unless the context clearly dictates otherwise. Also, as used in the description herein, the meaning of "in" includes "in" and "on" unless the context clearly dictates otherwise.

The term "embryonic stem cells" (ES cells) is used herein as it is used in the art. This term includes cells derived from the inner cell mass of human blastocysts or morulae, including those that have been serially passaged as cell lines. The ES cells may be derived from fertilization of an egg cell with sperm, as well as using DNA, nuclear transfer, parthenogenesis, or by means to generate ES cells with homozygosity in the HLA region. ES cells are also cells derived from a zygote, blastomeres, or blastocyst-staged mammalian embryo produced by the fusion of a sperm and egg cell, nuclear transfer, parthenogenesis, androgenesis, or the reprogramming of chromatin and subsequent incorporation of the reprogrammed chromatin into a plasma membrane to produce a cell. Embryonic stem cells, regardless of their source or the particular method use to produce them, can be identified based on (i) the ability to differentiate into cells of all three germ layers, (ii) expression of at least Oct 4 and alkaline phosphatase, and (iii) ability to produce teratomas when transplanted into immunodeficient animals.

As used herein, the term "pluripotent stem cells" includes embryonic stem cells, embryo-derived stem cells, and induced pluripotent stem cells, regardless of the method by which the pluripotent stem cells are derived. Pluripotent stem cells are defined functionally as stem cells that are: (a) capable of inducing teratomas when transplanted in immunodeficient (SCID) mice; (b) capable of differentiating to cell types of all three germ layers (e.g., can differentiate to ectodermal, mesodermal, and endodermal cell types); and (c) express one or more markers of embryonic stem cells (e.g., express Oct 4, alkaline phosphatase. SSEA-3 surface antigen, SSEA-4 surface antigen, nanog, TRA-1-60, TRA-1-81, SOX2, REX1, etc). Exemplary pluripotent stem cells can be generated using, for example, methods known in the art. Exemplary pluripotent stem cells include embryonic stem cells derived from the ICM of blastocyst stage embryos, as well as embryonic stem cells derived from one or more blastomeres of a cleavage stage or morula stage embryo (optionally without destroying the remainder of the embryo). Such embryonic stem cells can be generated from embryonic material produced by fertilization or by asexual means, including somatic cell nuclear transfer (SCNT), parthenogenesis, and androgenesis. Further exemplary pluripotent stem cells include induced pluripotent stem cells (iPSCs) generated by reprogramming a somatic cell by expressing a combination of factors (herein referred to as reprogramming factors). The iPSCs can be generated using fetal, postnatal, newborn, juvenile, or adult somatic cells.

In certain embodiments, factors that can be used to reprogram somatic cells to pluripotent stem cells include, for example, a combination of Oct 4 (sometimes referred to as Oct 3/4), Sox2, c-Myc, and Klf4. In other embodiments, factors that can be used to reprogram somatic cells to pluripotent stem cells include, for example, a combination of Oct 4, Sox2, Nanog, and Lin28. In certain embodiments, at least two reprogramming factors are expressed in a somatic cell to successfully reprogram the somatic cell. In other embodiments, at least three reprogramming factors are expressed in a somatic cell to successfully reprogram the somatic cell. In other embodiments, at least four reprogramming factors are expressed in a somatic cell to successfully reprogram the somatic cell. In other embodiments, additional reprogramming factors are identified and used alone or in combination with one or more known reprogramming factors to reprogram a somatic cell to a pluripotent stem cell. Induced pluripotent stem cells are defined functionally and include cells that are reprogrammed using any of a variety of methods (integrative vectors, non-integrative vectors, chemical means, etc).

Induced pluripotent stem cells can be produced by protein transduction of reprogramming factors in a somatic cell. In certain embodiments, at least two reprogramming proteins are transduced into a somatic cell to successfully reprogram the somatic cell. In other embodiments, at least three reprogramming proteins are transduced into a somatic cell to successfully reprogram the somatic cell. In other embodiments, at least four reprogramming proteins are transduced into a somatic cell to successfully reprogram the somatic cell.

The pluripotent stem cells can be from any species. Embryonic stem cells have been successfully derived in, for example, mice, multiple species of non-human primates, and humans, and embryonic stem-like cells have been generated from numerous additional species. Thus, one of skill in the art can generate embryonic stem cells and embryo-derived stem cells from any species, including but not limited to, human, non-human primates, rodents (mice, rats), ungulates (cows, sheep, etc), dogs (domestic and wild dogs), cats (domestic and wild cats such as lions, tigers, cheetahs), rabbits, hamsters, gerbils, squirrel, guinea pig, goats, elephants, panda (including giant panda), pigs, raccoon, horse, zebra, marine mammals (dolphin, whales, etc.) and the like. In certain embodiments, the species is an endangered species. In certain embodiments, the species is a currently extinct species.

Similarly, iPSCs can be from any species. These iPSCs have been successfully generated using mouse and human cells (hiPSCs). Furthermore, iPSCs have been successfully generated using embryonic, fetal, newborn, and adult tissue. Accordingly, one can readily generate iPSCs using a donor cell from any species. Thus, one can generate iPSCs from any species, including but not limited to, human, non-human primates, rodents (mice, rats), ungulates (cows, sheep, etc), dogs (domestic and wild dogs), cats (domestic and wild cats such as lions, tigers, cheetahs), rabbits, hamsters, goats, elephants, panda (including giant panda), pigs, raccoon, horse, zebra, marine mammals (dolphin, whales, etc.) and the like. In certain embodiments, the species is an endangered species. In certain embodiments, the species is a currently extinct species.

Induced pluripotent stem cells can be generated using, as a starting point, virtually any somatic cell of any developmental stage. For example, the cell can be from an embryo, fetus, neonate, juvenile, or adult donor. Exemplary somatic cells that can be used include fibroblasts, such as dermal fibroblasts obtained by a skin sample or biopsy, synoviocytes from synovial tissue, foreskin cells, cheek cells, or lung fibroblasts. Although skin and cheek provide a readily available and easily attainable source of appropriate cells, virtually any cell can be used. In certain embodiments, the somatic cell is not a fibroblast.

The terms "hemangioblast" and "hemangio-colony forming cell" will be used interchangeably throughout this application. The cells have numerous structural and functional characteristics. Amongst the characteristics of these cells is the ability to engraft into the bone marrow when administered to a host. These cells can be described based on numerous structural and functional properties including, but not limited to, expression (RNA or protein) or lack of expression (RNA or protein) of one or more markers. Hemangio-colony forming cells are capable of differentiating to give rise to at least hematopoietic cell types or endothelial cell types. Hemangio-colony forming cells are preferably bi-potential and capable of differentiating to give rise to at least hematopoietic cell types and endothelial cell types. As such, hemangio-colony forming cells of the present invention are at least uni-potential, and preferably hi-potential. Additionally however, hemangio-colony forming cells may have a greater degree of developmental potential and can, in certain embodiments, differentiate to give rise to cell types of other lineages. In certain embodiments, the hemangio-colony forming cells are capable of differentiating to give rise to other mesodermal derivatives such as cardiac cells (for example, cardiomyocytes) and/or smooth muscle cells.

The terms "non-engrafting hemangioblasts" and "non-engrafting hemangio cells" are used throughout this application to refer to a population of cells that share some of the characteristics of hemangio-colony forming cells. However, the non-engrafting hemangio cells are distinguishable in that they do not engraft into the bone marrow when administered to an immunodeficient host. Despite this difference, non-engrafting hemangio cells may share one or more than one (2, 3, 4, 5, 6, 7, 8, 9, 10) of the functional or structural characteristics and properties of hemangio-colony forming cells. For example, in certain embodiments, the non-engrafting hemangio cells are loosely adherent to each other. In other embodiments, the non-engrafting hemangio cells do not express one or more than one (2, 3, 4) of the following proteins: CD34, KDR, CD133, CD31. Without being bound by theory, non-engrafting hemangio cells may provide a distinct stem cell population that is somewhat more committed than hemangio-colony forming cells, and yet still capable of producing a range of hematopoietic cell types.

Limitations in the supply of platelets can have potentially life-threatening consequences for transfusion-dependent patients. hESCs can be propagated in vitro indefinitely, and represent a potentially inexhaustible and donorless source of platelets for human therapy. The ability to create banks of hESC lines with matched or reduced incompatibility could potentially decrease or eliminate the need for immunosuppressive drugs and/or immunomodulatory protocols. With the advent of induced pluripotent stem cells (iPSCs)[41;42;43;44], it can be possible to adapt these techniques to produce patient-specific platelets for transfusion-dependent patients who develop platelet alloimmunity.

Platelets collected from donors have very limited shelf life and are increasingly needed for prophylactic transfusions in patients. In contrast to donor dependent cord blood or bone marrow CD34+ human hematopoietic stem cells, human embryonic stem cells (hESCs) can be a promising alternative source for continuous in vitro production of platelets under controlled conditions. The inventors have developed a novel system to generate megakaryocytes (MKs) from hESCs under serum- and stromal-free conditions. In this system, hESCs are directed towards megakaryocytes through embryoid body formation and hemangioblast differentiation. A transient bi-potential cell population expressing both CD41a and CD235a markers has been identified at the end of hemangioblast culture. These cells are capable of generating both MKs and erythroid cells as demonstrated by FACS sorting and CFU assays. In the presence of TPO, SCF and other cytokines in serum-free suspension culture, up to 100 fold expansion can be achieved from hESCs to MKs in 14-15 days. This system represents a robust in vitro method to generate MKs from hESCs. When plated on OP9 cells, hESC derived MKs are able to generate platelet-like particles (ES-PLTs). These ES-PLTs are responsive to thrombin stimulation and able to participate in micro-aggregate format ion.

An efficient method to generate functional megakaryocytes from hESCs under serum- and stromal-free conditions is described. In the current system, hESCs were directed towards megakaryocyte differentiation using hemangio-blasts (herein also referred to as blast cells (BCs)) as intermediates[17], and up to $1 \times 10^8$ megakaryocytes were generated from $1 \times 10^6$ cells hESCs, which is approximately 10-20 times more efficient than that of the most recently reported methods by Takayama et al.[16] Without further purification, >90% of live cells from the suspension cultures are CD41a+ and the majority of these cells are also expressing CD42a and CD42b. These in vitro derived MK cells can undergo endomitosis and become mature, polyploid MKs as demonstrated by Giemsa staining and immunofluorescent staining of vWF in cytoplasmic granules. Importantly, pro-platelet forming cells are constantly observed at the late stage of MK culture indicating that MKs generated in this system are able to undergo terminal differentiation under feeder-free conditions. These results also show that when plated on OP9 stromal cells, these megakaryocytes generated platelet like particles sharing functional properties of blood platelets.

Described herein is an efficient system which is adaptable for massive in vitro megakaryocyte production using hESCs as source cells under controlled conditions. The cells expressed CD41a, CD42a and CD42b, and underwent endomitosis and formed mature polyploid MKs. Upon further maturation they generated platelets that can be activated by thrombin stimulation and able to spread on fibrinogen and von Willebrand factor (vWF) surfaces. The hESC-derived platelets also formed micro-aggregates, and facilitated clot formation and retraction in a manner comparable to normal human blood platelets. Importantly, these results also demonstrated that these in vitro derived megakaryocytes were capable of producing platelets functionally comparable to their blood counterparts. These ES-PLTs are responsive to platelet agonist by showing their ability to adhere and spread, and to form microaggregates together with normal blood platelets. Because no stromal cells or hand-picking process are involved for megakaryocyte productions, the current platform will also enable the establishment of conditions for stromal-free platelet generation. This is technically possible since stromal free conditions have been described for in vitro platelet production elsewhere including a recently published 3-D bioreactor system[30]. Factors including estradiol, vitamin B3 and extracellular matrix proteins have been previously reported to enhance platelet production[31-33]. These factors are tested in the system to stimulate megakaryocyte maturation and platelet productions without stromal cells.

The production of megakaryocytes under serum-free and stromal free conditions will allow screening for factors that are critical in regulating megakaryopoiesis and thrombopoiesis under well defined conditions. Factors identified in these future studies might contribute to future clinical applications. Advances in this area will also likely provide insights into the cellular and molecular mechanisms regulating different aspects of megakaryopoiesis including lineage commitment, expansion and maturation. The inventors' identification of a dual-potential CD41a+CD235a+ population in blast cultures will certainly facilitate the mechanistic studies into the lineage specifications of erythroid versus megakaryocytic cells. Recently, Klimchenko et al. reported similar megakaryocyte/erythroid bi-potent cells co-expressing both CD41a and CD235a from hematopoietic differentiation of human ES cells on OP9 stromal cells[34]. It is likely that these cells represent a branching point of erythropoiesis versus megakaryopoiesis. Detailed studies on this population will likely shed light on events that are involved in the regulation of this important process during hematopoiesis.

The system integrates step-wise inductions of megakaryocyte differentiation from hESCs. Further optimization and establishment of in-process controls can be performed to improve the consistency and efficiency of this system for clinical applications. At current stage, the underlying cellular or extra-cellular mechanisms regulating megakaryocyte maturation are not completely defined. Since majority of these cells are still diploid in the MK cultures, other factors promote polyploidization and cytoplasmic maturation may need to be identified and included in the system to facilitate the terminal differentiation of in vitro derived megakaryocytes. For instance, in the system, ROCK kinase inhibitor can induce endomitosis of megakaryocytes at early stage. However, this effect is likely due to an artificial blocking of chromosome segregation and cytokinesis rather than an orchestrated cellular and nuclear maturation of a differentiating megakaryocyte. It is important to reach a balance between the expansion, endomitosis and the cytoplasmic maturation to achieve the best outcome for the in vitro megakaryocyte yields, the terminal differentiation status and the downstream production of functional platelets under defined conditions.

These current results demonstrated that in vitro derived platelets are responsive to agonist stimulation induced integrin receptor remodeling and platelet spreading. Furthermore, the in vitro derived platelets can work together with plasma platelets and form aggregates. These in vitro derived human platelets are able to function in vivo as well. FACS characterizations and three functional tests (PAC1 binding assay, spreading assay and micro aggregate assay) that the inventors preformed for the human ES cell derived platelets show that the in vitro produced platelets are sharing morphological and functional properties of normal blood platelets. A recent report by Nichii et al., the in vivo functionality of in vitro derived mouse ES cell derived platelets has been tested with promising results's.

In vitro studies cannot mimic the myriad hemodynamic events that occur during the generation and propagation of platelet thrombi in the living organism. The availability of new intravital imaging technology provides a means to directly examine and quantify the platelet-dependent thrombotic process that occurs after vascular injury in complex in vivo systems. Using intravital high-speed widefield microscopy, the inventors demonstrated that hESC-derived platelets are incorporated into the developing mouse platelet thrombus at the site of laser-induced arteriolar wall injury in living mice similar to normal human blood platelets. Pretreatment of the hESC-derived and control platelets with ReoPro markedly reduced the number of platelets incorporating in the thrombi, confirming the binding was mediated by αIIbβ3 integrin. These results provide valuable evidence that hESC-derived platelets are functional at the site of vascular injury in living animals.

Platelets are anucleate cells that adhere to tissue and to each other in response to vascular injury. This process is primarily mediated by the platelet integrin αIIbβ3, which binds to several adhesive substrates such as vWF and fibrinogen to bridge and further activate platelets in a growing thrombus[36]. The results herein demonstrate that platelets generated from hESCs are functionally similar to normal blood platelets both in vitro and in living animals. The hESC-PLTs were shown to possess important functions involved in hemostasis, including the ability to adhere and spread on fibrinogen and vWF coated surfaces, as well as to aggregate when stimulated with physiological agonists. Importantly, it is shown for the first time that platelets derived from hESCs are able to retract fibrin clots. In addition to their central role in primary hemostasis, the results show hESC-PLTs can facilitate coagulation by interacting with fibrin, which promotes wound healing by the integrin-mediated retractile motion.

A critical scientific and clinical issue is whether hESC-derived platelets are functional in the complex in vivo setting. A large number of experimental models have been established in the past decade to investigate thrombus formation in mice, including the laser-injury thrombosis model recently used by several groups[37;38;39]. The laser-induced thrombosis model initiates platelet thrombus formation as fast as 5-30 second following injury. Therefore, this model allows the monitoring of the real-time incorporation of rapidly cleared human platelets and hESC-PLTs into the developing mouse platelet thrombus, which involves a large number of signaling pathways, enzymatic cascades, as well as the interplay of a myriad of cellular and protein components. This model also mirrors the inflammatory reactions associated with thrombin-induced thrombosis.

Figure 7:
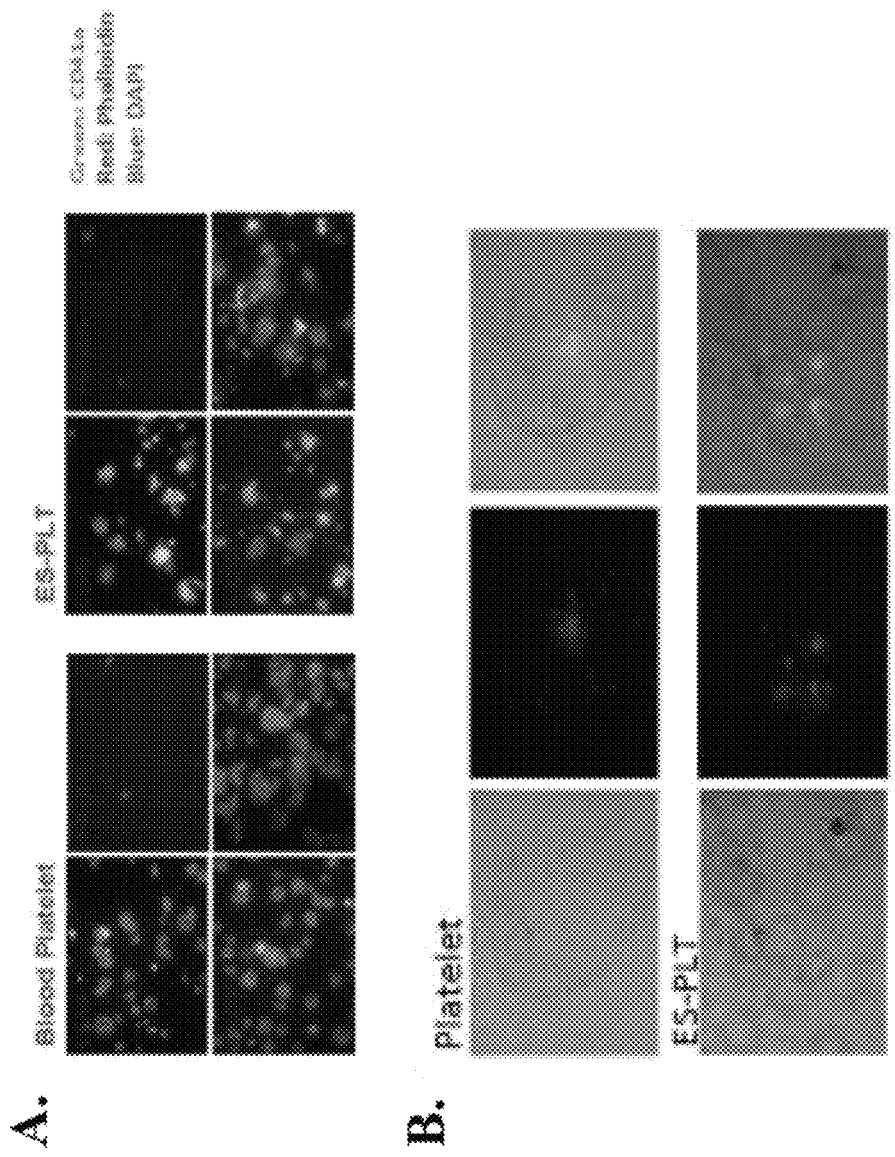
FIG. 7 depicts ES-PLTs binding to immobilized fibrinogen and form micro-aggregates in accordance with various embodiments of the present invention. A. Spreading assay shows blood platelets (left panels) and ES-PLTs (right panels) are able to spread on glass slides coated with fibrinogen. This process is dependent on integrin receptor signaling because adding of RGDS blocks the spreading. Addition of either ADP (+ADP) or thrombin (+T) enhances the spreading process on fibrinogen comparing to fibrinogen only (Con). Integrin dependent rearrangement of F-actin fibers and formation filopodia are shown by fluorescent staining of CD41a (green) and phalloidin (F-Actin, red). B. Micro-aggregate formation assay. Same numbers of PKH67 (green) labeled blood platelets (upper panels) or ES-PLTs (lower panels) were mixed with unlabeled blood platelets to form aggregates under the stimulation of thrombin (0.5 u/ml). Phase contrast and fluorescent images show that comparable participation of labeled ES-PLTs into micro-aggregates to human blood platelet control. C. Histograms of FACS analyses show HLA expression in ES-PLTs. Blood platelets were used as control (left).
Figure 7:
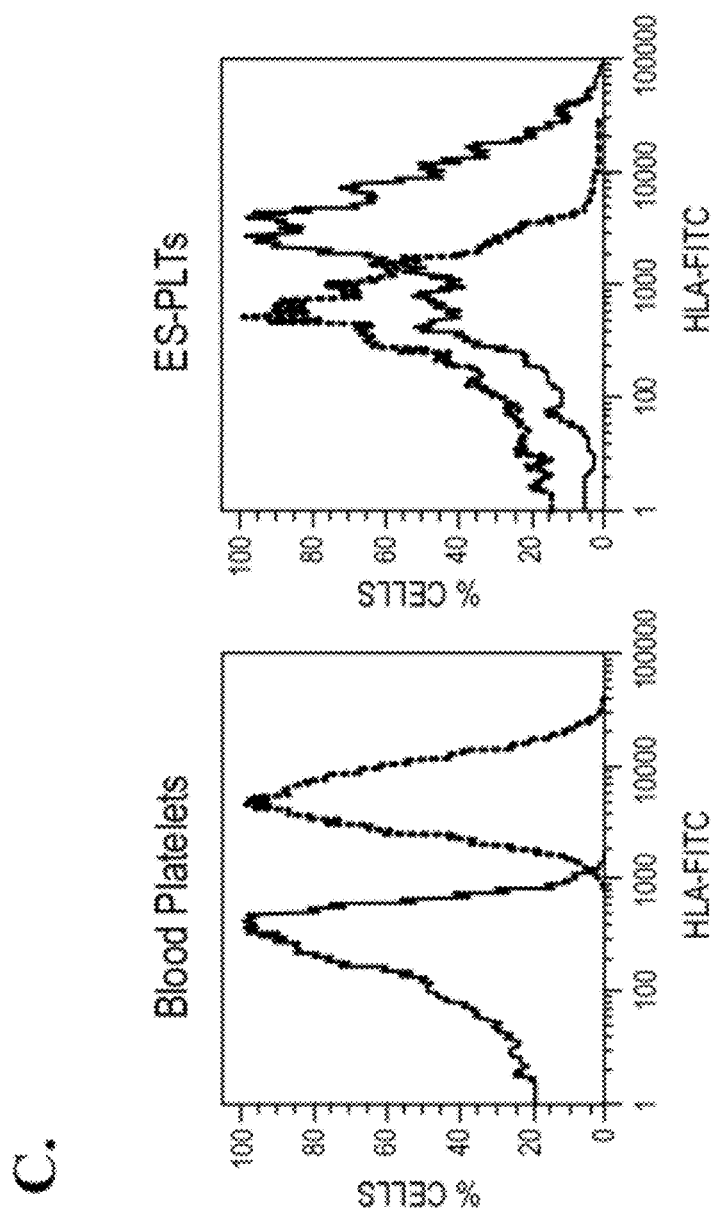
Figure 11:
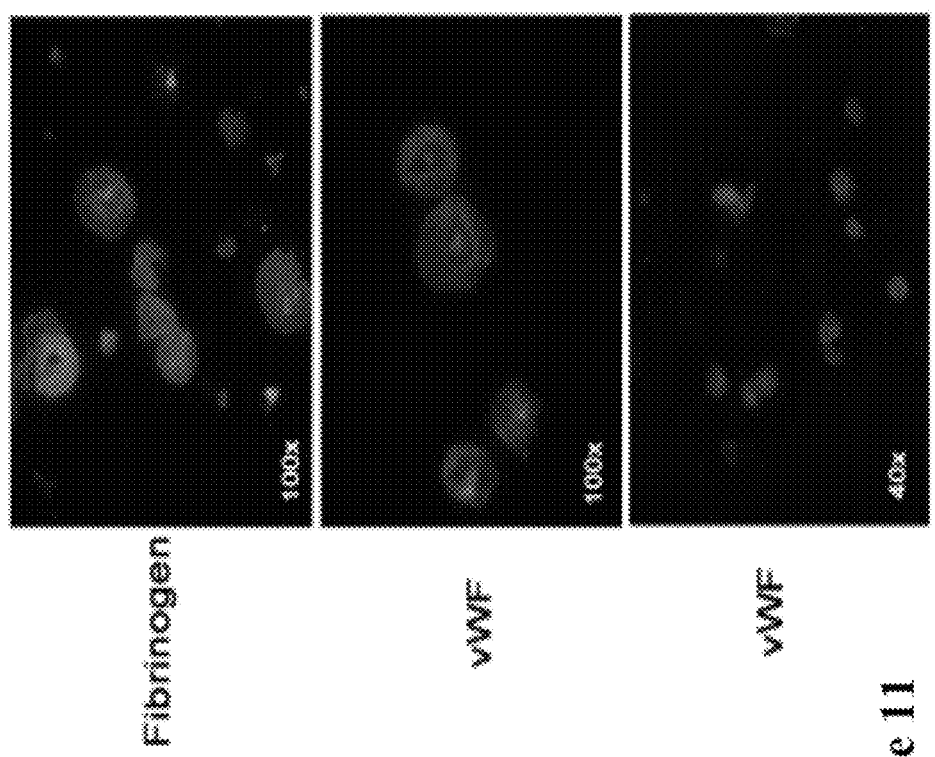
FIG. 11 depicts spreading assay of hESC-platelets generated under feeder and serum-free condition in accordance with various embodiments of the present invention. Microtiter chamber slides were coated with 100 µg/mL fibrinogen (upper panel) or 30 µg/mL vWF (middle and lower panels). hESC-platelets were allowed to spread for 90 minutes. Adherent platelets were stained with Alexa Fluor 568 phalloidin, FITC conjugated anti-human CD41a antibody and DAN, and photographed under a fluorescence microscope.

Using the laser-induced vessel injury model, the intravital microscopy analyses demonstrate that hESC-PLTs, like blood platelets, are incorporated into the developing mouse platelet thrombus through αIIbβ3 integrin following vascular injury. The number of hESC-PLTs interacting with the mouse platelet thrombus was lower than that of human blood platelets (FIG. 9C), which may be due to the reduced PAC-1 binding to activated hESC-PLTs compared to activated human blood platelets (FIG. 7G and FIG. 11). These results provide clear evidence that hESC-PLTs are functional at the site of vascular injury in vivo.

Two previous studies have reported the generation of MKs from hESCs. The yield in these systems is extremely low (<100-fold than reported here), and unlike the current system, rely on co-culture with animal stromal cells supplemented with serum [15;16]. Moreover, only one of which demonstrated the generation of hESC-platelets that was functional in vitro, but their in vivo functionality was not reported[16]. The elimination of these two variables in hESC differentiation allows the generation of platelets without exposure to animal products. While it was observed that the feeder-free system used in the present study generates MKs with high efficiency, the final step of generating functional platelets under the feeder-free conditions is less efficient than that of the OP9 cell co-culture system.

Therefore, these results suggest that OP9 stromal cells provide additional supporting factors that can enhance the generation of functional platelets from hESC-MKs. The underlying mechanism remains to be investigated. Thrombopoiesis is a highly complex process, with sophisticated reorganization of membrane and microtubules and precise distributions of granules and organelles[40]. Despite recent advances in the understanding of platelet biogenesis, mechanistic details underlying membrane reorganization, initiation of proplatelets, transportation of platelet organelles and secretary granules, and control of platelet size remain to be elucidated. The ability to generate MKs under serum- and feeder-free conditions should aid in the screening of factors that are critical in regulating different aspects of megakaryopoiesis under well-defined conditions, including lineage commitment, expansion and maturation.

Megakaryocytes

Various embodiments of the present invention provide for a method of generating functional megakaryocytes from human embryonic stem cells and pluripotent stem cells (including iPSCs and hiPSCs) under stromal-free conditions. Pluripotent stem cells, including hiPSCs and hESCs were directed towards megakaryocyte differentiation using hemangioblasts/blast cells as intermediates.

In one embodiment, the method comprises: providing hemangioblasts (also referred to as blast cells); and differentiating the hemangioblasts into megakaryocytes. In one embodiment, the hemangioblasts are human hemangioblasts. In another embodiment, the hemangioblasts are derived from hESCs. In another embodiment, the hemangioblasts are derived from induced pluripotent stem cells (iPSCs). In another embodiment, the hemangioblasts are human iPSCs (hiPSCs) derived from reprogramming somatic cells. In one embodiment, the somatic cells are from fetal tissue. In another embodiment, the somatic cells are from adult tissue. In an alternative embodiment, the hemangioblasts may be non-engrafting hemangioblasts.

In one embodiment, differentiating the hemangioblasts into megakaryocytes comprises: purifying and plating the Day 6 to Day 8 hemangioblasts in media supplemented with TPO, SCF to induce BC differentiation toward MKs. In various embodiments, the concentrations are TPO (50 ng/ml) and SCF (20 ng/ml). In another embodiment, the concentrations are TPO (100 ng/ml) and SCF (50 ng/ml). In another embodiment, the media is also supplemented with IL11 (e.g., 20 ng/ml). In a further embodiment, the MKs express CD41a, CD42a and CD42b. In alternative embodiments, the media is also supplemented with IL6, IL11, VEGF, bFGF, estradiol, vitamin B3, and/or extracellular matrix proteins. In a further embodiment, the method further comprises replacing the media supplemented with TPO, SCF, and/or IL11 with fresh media every 2 to 3 days. In another embodiment, the method comprises replacing at least a portion of the media supplemented with TPO, SCF, and/or IL11, with fresh media every 2 to 3 days. In an alternative embodiment, the method further comprises replacing half of the media supplemented with TPO, SCF, and/or IL11, with fresh media every 2 to 3 days. In various embodiments, about 1 to $5\times10^5$ cells/ml are plated. In various embodiments, Stemline II media is used.

In another embodiment, the present invention provides for a method of screening for a modulator of cellular differentiation comprising: providing a quantity of megakaryocytes (MKs); contacting the MKs with a test compound; and determining the presence or absence of a functional effect from the contact between the MKs and the test compound, wherein the presence of a functional effect indicates that the test compound is a megakaryopoietic, thrombopoietic, and/or hematopoeitic factor that modulates cellular differentiation and the absence of a functional effect indicates that the test compound is not a megakaryopoietic, thrombopoietic, and/or hematopoeitic factor that modulates cellular differentiation. In other embodiments, megakaryopoietic, thrombopoietic, and/or hematopoeitic factors relate to the expansion, endomitosis, cytoplasmic maturation, and terminal differentiation of functional platelets.

Platelets

Other embodiments of the present invention provide for a method of generating platelets from human embryonic stem cells and pluripotent stem cells (including iPSCs and hiPSCs). In one embodiment, the method comprises: providing human embryonic stem cells (hESCs); forming embryoid bodies (EB); generating hemangioblasts (also referred to as blast cells (BCs)); differentiating the BCs into megakaryocytes; and differentiating the megakaryocytes into platelets. In an alternative embodiment, the hemangioblasts may be non-engrafting hemangioblasts.

Other embodiments of the present invention provide for a method of generating platelets from pluipotent stem cells. In one embodiment, the method comprises: providing pluripotent stem cells; forming embryoid bodies (EB); generating hemangioblasts (also referred to as blast cells (BCs)); differentiating the BCs into megakaryocytes; and differentiating the megakaryocytes into platelets. In one embodiment, the hemangioblasts are human hemangioblasts. In another embodiment, the hemangioblasts are derived from hESCs. In another embodiment, the hemangioblasts are derived from induced pluripotent stem cells (iPSCs). In one embodiment, the iPSCs are human iPSCs (hiPSCs) derived from reprogramming somatic cells. In one embodiment, the somatic cells are from fetal tissue. In another embodiment, the somatic cells are from adult tissue. In an alternative embodiment, the hemangioblasts may be non-engrafting hemangioblasts.

In another embodiment, the method of generating platelets comprises: providing hemangioblasts; differentiating the hemangioblasts into megakaryocytes; and differentiating the megakaryocytes into platelets. In an alternative embodiment, the hemangioblasts may be non-engrafting hemangioblasts. The process of differentiating the hemangioblasts into megakaryocytes can be performed as described above. In one embodiment, the hemangioblasts are human hemangioblasts. In another embodiment, the hemangioblasts are derived from hESCs. In another embodiment, the hemangioblasts are derived from induced pluripotent stem cells (iPSCs). In one embodiment, the iPSCs are human iPSCs (hiPSCs) derived from reprogramming somatic cells. In one embodiment, the somatic cells are from fetal tissue. In another embodiment, the somatic cells are from adult tissue. In an alternative embodiment, the hemangioblasts may be non-engrafting hemangioblasts.

In various embodiments, the process of differentiating the megakaryocytes into platelets comprises continuing to culture the megakaryocytes to allow the megakaryocytes to differentiate into platelets. In various embodiments, the process of differentiating the megakaryocytes into platelets is under feeder free conditions and comprises collecting the megakaryocytes from Day 4 to 6 megakaryocyte culture; and resuspending the megakaryocytes in media supplemented with TPO, SCF, and sodium heparin. In certain embodiments, the concentrations of TPO (100 ng/ml), SCF (50 ng/ml), and sodium heparin (25 units/ml). In certain embodiments, the media is also supplemented with IL11 (e.g., 20 ng/ml). In an alternative embodiment, the media is also supplemented with IL3, IL6, IL11, VEGF, bFGF, estradiol, vitamin B3, and/or extracellular matrix proteins. In certain embodiments, IL3 is added from Day 4 to 7 megakaryocyte culture. In another embodiment, metalloproteinase inhibitor GM 6001 is added after Day 4 megakaryoyte culture. In certain embodiments, the media is IMDM media. In further embodiments, the media comprising TPO, SCF, and sodium heparin and optionally IL11 is replaced every 2 days. In another embodiment, the method further comprises replacing at least a portion of the media comprising TPO, SCF, and sodium heparin and optionally IL11 with fresh media every 2 to 3 days. In an alternative embodiment, the method further comprises replacing half of the media comprising TPO, SCF, and sodium heparin and optionally IL11 with fresh media every 2 to 3 days. In further embodiments, platelets are collected from Day 4 to Day 12 megakaryocyte culture. In various embodiments, the process of differentiating megakaryocytes into platelets comprises continuing to culture the megakaryocytes to allow the megakaryocytes to differentiate into platelets. In various embodiments, a variety of factors improve efficient platelet formation from megakaryocytes. In various embodiments, IL6, IL3, Notch, or other types of cytokines, interleukins, growth factors, small molecules and combinations thereof improve efficiency of platelet differentiation from megakaryocytes.

In other embodiments, the method of differentiating the megakaryocytes into platelets comprises co-culturing the megakaryocytes with OP9 stromal cells or C3H 10T1/2 cells. In various embodiments, co-culturing the megakaryocytes with OP9 stromal cells or C3H 10T1/2 cells comprises collecting the megakaryocytes from Day 4 to 6 megakaryocyte cultures; and resuspending the megakaryocytes in media supplemented with TPO, SCF, and sodium heparin. In certain embodiments, the concentrations of TPO (100 ng/ml), SCF (50 ng/ml), and sodium heparin (25 units/ml). In certain embodiments, the media is also supplemented with IL11 (e.g., 20 ng/ml). In an alternative embodiment, the media is also supplemented with IL3, IL6, IL11, VEGF, bFGF, estradiol, vitamin B3, and/or extracellular matrix proteins. In certain embodiments, IL3 is added from Day 4 to 7 megakaryocyte culture. In another embodiment, metalloproteinase inhibitor GM 6001 is added after Day 4 megakaryoyte culture. In further embodiments, the media comprising TPO, SCF, and sodium heparin and optionally IL11 is replaced every 2 days. In another embodiment, the method further comprises replacing at least a portion of media comprising TPO, SCF, and sodium heparin and optionally IL11 with fresh media every 2 to 3 days. In an alternative embodiment, the method further comprises replacing half of the media comprising TPO, SCF, and sodium heparin and optionally IL11 with fresh media every 2 to 3 days. In various embodiments, a variety of factors improve efficient platelet formation from megakaryocytes. In various embodiments, IL6, IL3, Notch, or other types of cytokines, interleukins, growth factors, small molecules and combinations thereof improve efficiency of platelet differentiation from megakaryocytes.

In further embodiments, platelets are collected from Day 4 to Day 12 megakaryocyte culture. In certain embodiments, the platelets are purified using density gradient centrifugation. In further embodiments, the density gradient centrifugation uses Percoll medium. In another embodiment, the platelet purification method separates particles that are CD41a negative. In another embodiment, the platelet purification method retains cell viability and morphological integrity. In other embodiments, the platelets express CD41a and CD42b. In other embodiments, the platelets are responsive to thrombin stimulation. In another embodiment, the platelets are able to spread on fibrinogen and von Willebrand factor (vWF) surfaces. In alternative embodiments, the platelets have capacity for PAC-1 binding and integrin activation. In another embodiment, the platelets form microaggregates and facilitate clot formation and retraction. In another embodiment, the platelets are not activated in the presence of apyrase and/or EDTA.

Various embodiments of the present invention provide for a method of using hESC-derived platelets. In certain embodiments, the hESC-derived platelets are used in platelet transfusions. The method may comprise providing a quantity of hESC-derived platelets; and administering the quantity hESC-derived platelets to a subject in need thereof. In various embodiments the hESC-derived platelets can be patient-matched platelets. In another embodiment, the platelets are derived from iPSCs. In a certain embodiment, the platelets are derived from hiPSCs. In other embodiments, the platelets are stored in a solution that does not contribute to an HLA alloimmunogenic response in a subject upon administration of the platelets to the subject.

Hemangioblasts

In various embodiments, hemangioblasts may be generated by a method comprising: providing human embryonic stem cells (hESCs); forming embryoid bodies (EB); and generating blast cells (BCs). In alternative embodiments, the method comprises providing pluripotent stem cells (including iPSCs and hiPSCs); forming embryoid bodies (EB); and generating blast cells (BCs). In certain embodiments, the iPSCs are derived from reprogramming somatic cells. In one embodiment, the somatic cells are from fetal tissue. In another embodiment, the somatic cells are from adult tissue.

In one embodiment, forming EBs comprises: dissociating hESCs; plating the dissociated hESCs with medium supplemented BMP-4 and VEGF for about 48 hours; and replacing half of the medium with fresh medium comprising BMP-4, VEGF, bFGF, SCF, Flt3 ligand and/or Tpo. In another embodiment, the media supplemented with BMP-4, VEGF, bFGF, SCF, Flt3 ligand and/or Tpo is replaced every 2 days. In an another embodiment, at least a portion of the media supplemented with BMP-4, VEGF, bFGF, SCF, Flt3 ligand and/or Tpo is replaced every 2 days. In alternative embodiments, pluripotent stem cells (including iPSCs and hiPSCs) are used in place of the hESCs.

In various embodiments, dissociating hESCs comprises dissociating hESCs by trypsin. In one embodiment, the concentration of trypsin is 0.05%. In various embodiments, the medium is Stemline II medium. In various embodiments, the concentration of BMP-4 and VEGF are both 50 ng/ml. In various embodiments, the concentrations of bFGF, SCF, Flt3 ligand and Tpo are bFGF (20 ng/ml), SCF (50 ng/ml), Flt3 ligand (50 ng/ml) and Tpo (50 ng/ml). In an alternative embodiment, the media is also supplemented with IL6, IL11, VEGF, bFGF, estradiol, vitamin B3, and/or extracellular matrix proteins. In another embodiment, forming EBs further comprises continued culturing of the cells. In another embodiment, the media supplemented with BMP-4, VEGF, bFGF, SCF, Flt3 ligand and/or Tpo is replaced every 2 days. In an another embodiment, at least a portion of the media supplemented with BMP-4, VEGF, bFGF, SCF, Flt3 ligand and/or Tpo is replaced every 2 days. In one embodiment, half of the media supplemented with BMP-4, VEGF, bFGF, SCF, Flt3 ligand and/or Tpo is replaced every 2 days.

In one embodiment, generating hemangioblasts comprises: collecting embryoid bodies (EBs) on Day 4 EB culture; dissociating the EBs; obtaining single-cell suspensions; mixing live cells with blast colony growth medium (BGM); and plating the live cells to generate the hemangioblasts.

In various embodiments dissociating the EBs comprises dissociating by trypsin. In various embodiments, obtaining single-cell suspensions comprises passing the cells through a 22-gauge needle and through a 40 µm cell strainer, collecting the cells by centrifugation and resuspending the cells in media. In one embodiment, the media is Stemline II media. In various embodiments, mixing live cells with blast colony growth medium (BGM) comprises mixing 1 to $2 \times 10^5$ cells/ml with BGM. In a further embodiment, blast colonies form 3-4 days after plating the live cells to generate the hemangioblasts. In a further embodiment, the hemangioblast are rapidly expanded. In another embodiment, the hemangioblasts are CD71 positive, CXCR4 positive, and express TPO receptor. In another embodiment, the hemangioblasts are CD31 negative, CD 34 negative, and KDR negative.

International Application Nos. PCT/US09/43050 and PCT/US09/43043 both filed May 6, 2009 and herein incorporated by reference as though fully set forth in their entirety, provide additional guidance on the generation of hemangioblasts and non-engrafting hemangioblasts.

EXAMPLES

The following examples are provided to better illustrate the claimed invention and are not to be interpreted as limiting the scope of the invention. To the extent that specific materials are mentioned, it is merely for purposes of illustration and is not intended to limit the invention. One skilled in the art may develop equivalent means or reactants without the exercise of inventive capacity and without departing from the scope of the invention.

Example 1

Culture of hESCs

Human ESC lines (HUES3, H1, MA01 and MA09) used in this study were maintained as previously described[18]. Briefly, hESCs were grown on mitomycin C-treated mouse embryonic fibroblast (MEF) in complete hESC growth media supplemented with 8 ng/ml bFGF. The hESCs were passaged every 3-4 days at 60-80% confluence using 0.05% trypsin-EDTA. Cells were maintained at 37° C. under 5% $CO_2$ and the medium was replenished daily.

Example 2

Embryoid Body (EBs) Formation and the Generation of Blast Cells (BCs)

The procedure for EB formation and BC generation were performed as previously reported[17;19]. In brief, hESCs at 70% confluency were dissociated by 0.05% trypsin and plated in Ultra-Low dishes (Corning, N.Y.) with Stemline II (Sigma) medium supplemented with BMP-4, VEGF (50 ng/ml). Half of the medium was replaced after 48 hours with fresh medium containing the same cytokines plus bFGF 20 ng/ml, SCF, Flt3 ligand (FL) and Tpo (50 ng/ml each, R&D System). On day 4, EBs were collected and dissociated by 0.05% trypsin. Single-cell suspensions were obtained by passing the cells through 22-gauge needle and through a 40 μm cell strainer, collected by centrifugation, and resuspended in Stemline II media. Live cells were counted by trypan blue exclusion, and 1 to $2\times10^5$/ml were mixed with blast colony growth medium (BGM) as previously described, and plated in Ultra-Low dishes. Blast colonies were observed 3-4 days after plating, followed by rapid expansion.

Example 3

Megakaryocyte Differentiation Culture

BCs from day 6 to 8 blast cultures were purified and plated (1 to $5\times10^5$/ml) in Stemline II media supplemented with 50 ng/ml TPO, 20 ng/ml SCF and other cytokines to induce BC differentiation toward MKs. Half of the MK culture media was replaced with fresh media every 2 or 3 days.

OP9 stromal cells were maintained in α-MEM with 15% fetal bovine serum (Hyclone). Confluent OP9 cells were treated with 100 ng/ml mitomycin-C the day before co-culture. Cells were gently washed twice with PBS and recovered over night in OP9 culture media prior to co-culture. For OP9 co-culture, megakaryocytes from Day 4 to 6 MK cultures were collected and resuspended in IMDM medium supplemented with 100 ng/ml TPO, 50 ng/ml SCF and 25 units/ml sodium heparin as described by Takayama et al.[16], and refreshed every 2 days. Platelet-like particles were collected from day 4 to day 12 for analyses.

Example 4

FACS Analysis

Cells from blast cultures or megakaryocyte cultures are monitored routinely by flow cytometry analyses on FACS Caliber. Fluorochrome conjugated antibodies for lineage markers, CD41a, CD42a, CD42b and CD235a (BD Biosciences) were used to characterize the megakaryocyte and erythroid lineages. Antibodies were freshly prepared (1:100 dilution for CD42a and CD42b antibodies; 1:250 dilution for CD41a antibody; 1:2000 for CD235a antibody) in PBS with 5% new born calf serum. Typically 1 to $2\times10^5$ cells were used for antibody labeling. Cells were stained in 100 μl antibody cocktail for 1 hour on ice, then washed twice with buffer, and resuspended in 250 μl buffer supplemented with 1 μg/ml propidium iodide. To detect the expression level of HLA-ABC, platelets were incubated with a fluorescein isothiocyanate (FITC)-conjugated antihuman HLA-ABC antibody or FITC-conjugated mouse immunoglobulin G (IgG) as a control. The samples were then analyzed using a flow cytometer (FACSCalibur, Becton Dickinson), and data were analyzed using Cellquest or Flowjo software. Cell sorting was performed on BD FACS Aria system at UMASS Medical School Core Facility. Sorted cells were collected by centrifugation at 1000 rpm for 10 minutes and resuspended in appropriate media for colony formation assays.

Example 5

Colony Formation Assay with Megacult-C and Methylcellulose

Megacult-C and 119436 methylcellulose media (Stem Cell Technology) were used for CFU-MK and CFU-E colony formation assays. After 10 days of plating, CFU-MK cultures were dehydrated, fixed, and stained with anti-CD41 antibody as suggested by the manufacturer. CFU-MK colonies were scored according to the standards provided in the Megacult-C protocol. CFU-E colonies were scored on day 12.

Example 6

Cytospin Preparation, Giemsa Staining and Immunofluorescent Microscopy

Cells (1 to $2\times10^4$) from either blast cultures or megakaryocytes cultures were cytospun on polylysine coated slides by cyto-centrifugation (Cytopro). Slides were used for either Wright-Giemsa (Sigma) or immunofluorescent staining. Anti-CD41 (DAKO, 1:100) and anti-vWF (DAKO, 1:200) antibodies were used for identifying megakaryocytes in cytospin preparations. All the incubations were performed at room temperature. Cells were blocked with animal-free blocker (Vector Laboratories) for 30 minutes. Cells were incubated with primary antibodies for 1 hour, then washed three times with PBS. The following incubations and washes were performed in dark. Cells were then incubated with secondary antibodies (1:200 each) for 30 minutes. Cells were washed again with PBS three times. Hoechst dye (1 μg/ml) in PBS was used to stain the nuclei DNA for 5 minutes followed by additional 3×PBS washes. Slides were then mounted and examined under fluorescent microscope (Olympus BXV). Fluorescent images were captured by using a QICAM Fast camera (Qimaging, Canada) and analyzed with QCapture Pro version 5.1 software (Media Cybernetics Inc., Bethesda, Md.). Phase contrast live cell images were captured using Nikon microscope, PAXCAM digital camera and PAX-it software.

Example 7

Preparation of Platelets

Human peripheral platelets were isolated by differential centrifugation of platelet rich plasma (AllCells, Emeryville, Calif.) with 1 U/mL apyrase and 5 mM EDTA (Sigma-Aldrich, St Louis, Mo.). Platelets were washed and resuspended in modified Tyrode's buffer (12 mM $NaHCO_3$, 138 mM NaCl, 5.5 mM Glucose, 2.9 mM KCl, 0.42 mM $NaHPO_4$, 10 mM HEPES, 1 mM $CaCl_2$, 1 mM $MgCl_2$). Culture media containing platelets derived from hESCs (ES-PLTs) were gently collected, apyrase (1 U/ml) and EDTA (5 mM) (Sigma-Aldrich, St Louis, Mo.) were added to prevent platelet activation, then spun at 300 g for 10 minutes to pellet cells. The supernatant was transferred to a new tube and centrifuged at 1000 g for 10 minutes in the presence of apyrase (1 U/ml) and EDTA (5 mM) to collect platelets. Platelets were then washed once and resuspended in the modified Tyrode's buffer. Washed platelets were incubated at 37° C. for 1-2 hours before functional assays.

Example 8

Platelet Spreading on Immobilized Fibrinogen

Chamber slides with microtiter wells (Nalgen Nunc, Rochester, N.Y.) were coated with 100 pg/mL fibrinogen (Sigma) in 0.1M $NaHCO_3$ (pH 8.3) at 4° C. overnight. Washed human peripheral platelets or hESC-platelets ($1×10^7$/mL) were allowed to adhere and spread on fibrinogen-coated wells at 37° C. for 90 minutes. In some samples, platelets were preincubated with an integrin antagonist, RGDS peptide, for 5 minutes before loading. In other samples, platelets were mixed with ADP (10 μM) or thrombin (1 U/ml) (Sigma-Aldrich, St Louis, Mo.), and immediately loaded on to fibrinogen-coated wells. After wash with PBS, cells were fixed, permeabilized, and stained with Alexa Fluor 568 phalloidin (Molecular Probes, Eugene, Oreg.), FITC conjugated anti-human CD41a antibody (Dako cytomation, Carpinteria, Calif.) and DAPI. Adherent platelets were viewed with an Olympus BX51 fluorescence microscope (MVI, Avon, Mass.) using a PlanApo lens at 100×/1.40 oil objective. Images were acquired using a QICAM Fast camera (QImaging, Surrey, BC Canada) and processed with Q Capture version 5.1 software (Media Cybernetics Inc., Bethesda, Md.).

Example 9

Platelet Aggregation

Washed human peripheral platelets and hESC-platelets were resuspended in modified Tyrode buffer and labeled with a PKH67 Green Fluorescent Cell Linker (10 μM, Sigma, St. Louis, Mo.). Human peripheral platelets ($6×10^7$) were mixed with fluorescence labeled human peripheral platelets ($3×10^5$) or hESC-platelets ($3×10^5$) in a 450 μl cuvette (Chronolog, Havertown, Pa.), then added with thrombin (0.5 U/mL) and stirred at 1200 rpm at 37° C. to trigger platelet aggregation. In control experiments, RGDS peptide was preincubated with platelets at 37° C. for 5 minutes before addition of thrombin, and performed the aggregation assay as above. Platelet micro-aggregates in 50 μL buffer were spread onto a glass slide and visualized under a florescence microscope.

Example 10

PAC-1 Binding Assay

ES-PLTs with or without thrombin stimulation (1 U/ml, incubation at room temperature for 20 minutes) were stained with APC-conjugated CD41a, PE-conjugated CD42b and FITC-conjugated PAC-1 antibodies in the modified Tyrode's buffer. The samples were then analyzed using a flow cytometer (FACSCalibur, Becton Dickinson), Forward scatter and side scatter gating were determined using human blood platelets as controls. FACS data were analyzed using Cellquest or Flowjo software.

Example 11

Blast Cells (BCs) Derived from hESCs Generated Megakaryocytes

The inventors' previous study showed that BCs derived from hESCs can be efficiently differentiated into erythroid cells in vitro under appropriate conditions[20]. Since megakaryocytes (MKs) and erythrocytes share a common progenitor during mammalian hematopoiesis, the inventors reasoned that BCs derived from hESCs might also to able to differentiate into megakaryocytes under megakaryocytic-promoting conditions with TPO and other cytokines. A similar strategy as demonstrated in FIG. 1A was devised to differentiate MKs from hESCs. Early-stage EBs were generated from hESCs cultured in serum-free media supplemented with a combination of morphogens and early hematopoietic cytokines as reported previously[17;19]. The EBs were then dissociated and individual cells were plated in serum-free semi-solid blast-colony growth medium (BGM) for the growth and expansion of BCs. Grape-like blast colonies first appeared at the beginning of 3 day culture, and rapidly expanded from day 4 to day 6. At this stage, BCs are relatively homogenous in morphology with a size of ~15 μm in diameter on cytospin preparation (FIG. 1B). These BCs were first tested for their megakaryopoetic potential by colony-forming unit (CFU)-MK assay. As shown in FIGS. 1C and 1D, day 6 BCs derived from both HUES3 and H1 cells developed CFU-MK colonies in 10-12 days after replating, and these colonies were stained positive for CD41. In some CFU-MK colonies, cellular processes resemble proplatelet were observed in CD41 positive cells (FIG. 1D insert). These results demonstrated that hESC-derived BCs are able to differentiate into megakaryocytes. At the same time, significant differences in their CFU-MK potential were observed between HUES3 and H1 cell lines. BCs derived from HUES3 generated approximately 3.5 times more CFU-MK colonies than the same number of H1 blast cells.

The initial BGM medium contains EPO for efficient BC generation and erythroid cells (CD235a+) become dominant at the late stage of blast culture[20]. From the inventors' experiments, results showed that higher concentration of TPO (100 ng/ml) and SCF (50 ng/ml) during second phase of EB formation (2 days after plating of hESCs) and blast colony growth and expansion increased the percentage of CD41a+ cells at the end of blast culture. The addition of IL-11 (20 ng/ml) in BGM medium further increased the ratio of CD41a+ cells in day 6 to 8 of blast cultures. Therefore, the inventors adapted these modifications in the blast cultures to improve megakaryocyte lineage commitment in the current study. HUES3, MA01 and MA09 hESC lines were tested with the modified conditions. All three lines showed megakaryocytic potential. Similar to the observation made in CFU-MK assays (FIG. 1C), significant differences in the percentages of CD41a+ cells in BCs (day 6 to 8) generated from different hESC lines was observed by FACS analyses. For instance, 32.9+8.4% (n=13) of BCs from HUES3 cells, which is significantly more than MA01 and MA09 cell lines (P<0.001, student test). In MA01 or MA09 derived blast cells, 15.3%+5.8% (n=5) or 17.2%+3.7% (n=5) of these cells were CD41a+ respectively (FIG. 1E).

Example 12

Bi-Potential Blast Cells Gave Rise to Both Erythroid and Megakaryocytes

Figure 2:
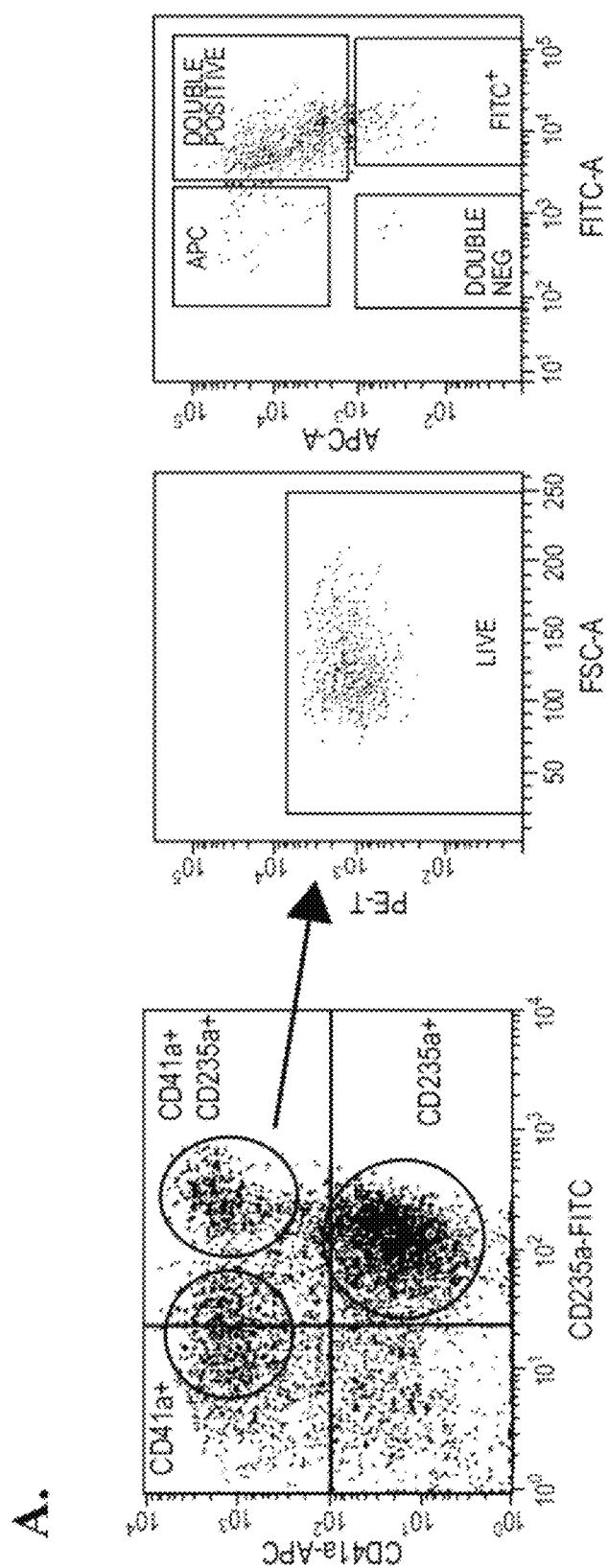
FIG. 2 depicts bi-potential progenitors from blast cultures give rise to both erythroid and megakaryocyte lineages in accordance with various embodiments of the present invention. A. FACS analysis of day 6 HUES3 derived blasts shows distinct populations defined by the expression of CD41a and CD235a markers (left) and sorted CD41a+CD235a+ cells (right). B. Images of CFU-MK colonies derived from either CD41a+CD235a− or CD41a+CD235a+ cells. Bar graph shows the quantification of CFU-MK colony assay. C. Images of CFU-E colonies derived from either CD41a−CD235a+ or CD41a+CD235a+ cells. Bar graph shows the quantification of CFU-E colony assay.
Figure 2:
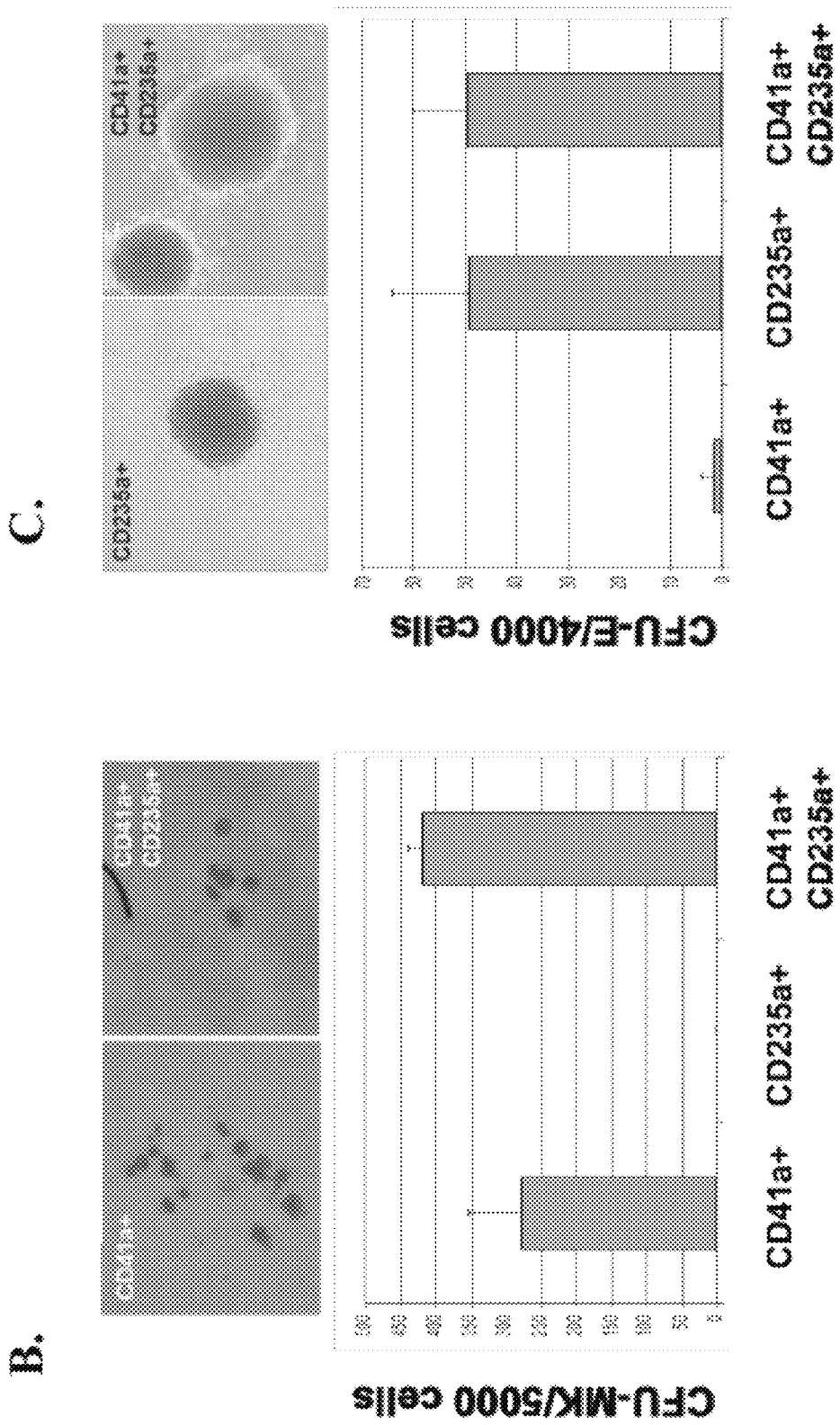

A major expansion occurred from day 5 to day 8 in blast cultures, and some blast colonies turned reddish during this period of time, indicating erythroid commitment and hemoglobin synthesis. FACS analyses showed that there were four distinct cell populations in BCs defined by the expression of megakaryocyte marker CD41a and erythroid marker CD235a: CD41a+CD235a−, CD41a−CD235a+, CD41a+CD235a+ and CD41a−CD235a− populations (FIG. 2A). Since the CD41a and CD235a double positive population share the markers for both erythroid and megakaryocyte lineage, it was tested if these cells represent a bi-potential precursors for both lineages.

Sorted CD41a+ CD235a−, CD41a−CD235a+ and CD41a+CD235a+ cells from day 6 blast cultures were then tested by two colony formation assays for either CFU-MK or CFU-E progenitors. Equal numbers of the sorted cells were plated for these colony assays. As expected, CD41a+CD235a− and CD41a−CD235a+ generated CFU-MK and CFU-E colonies respectively. At the same time, similar numbers of CFU-MK colonies were generated by CD41a+CD235a− and CD41a+CD235a+ cells, and comparable numbers of CFU-E were developed by CD41a−CD235a+ and CD41a+CD235a+ cells (FIGS. 2B and C). Therefore, these results show that CD41a+CD235a+ cells are bi-potential precursors for both megakaryocyte and erythroid lineages. These CD41a+CD235a+ cells appeared to be a transient population and disappeared shortly after cultured in megakaryocytic differentiation culture.

Example 13

Figure 3:
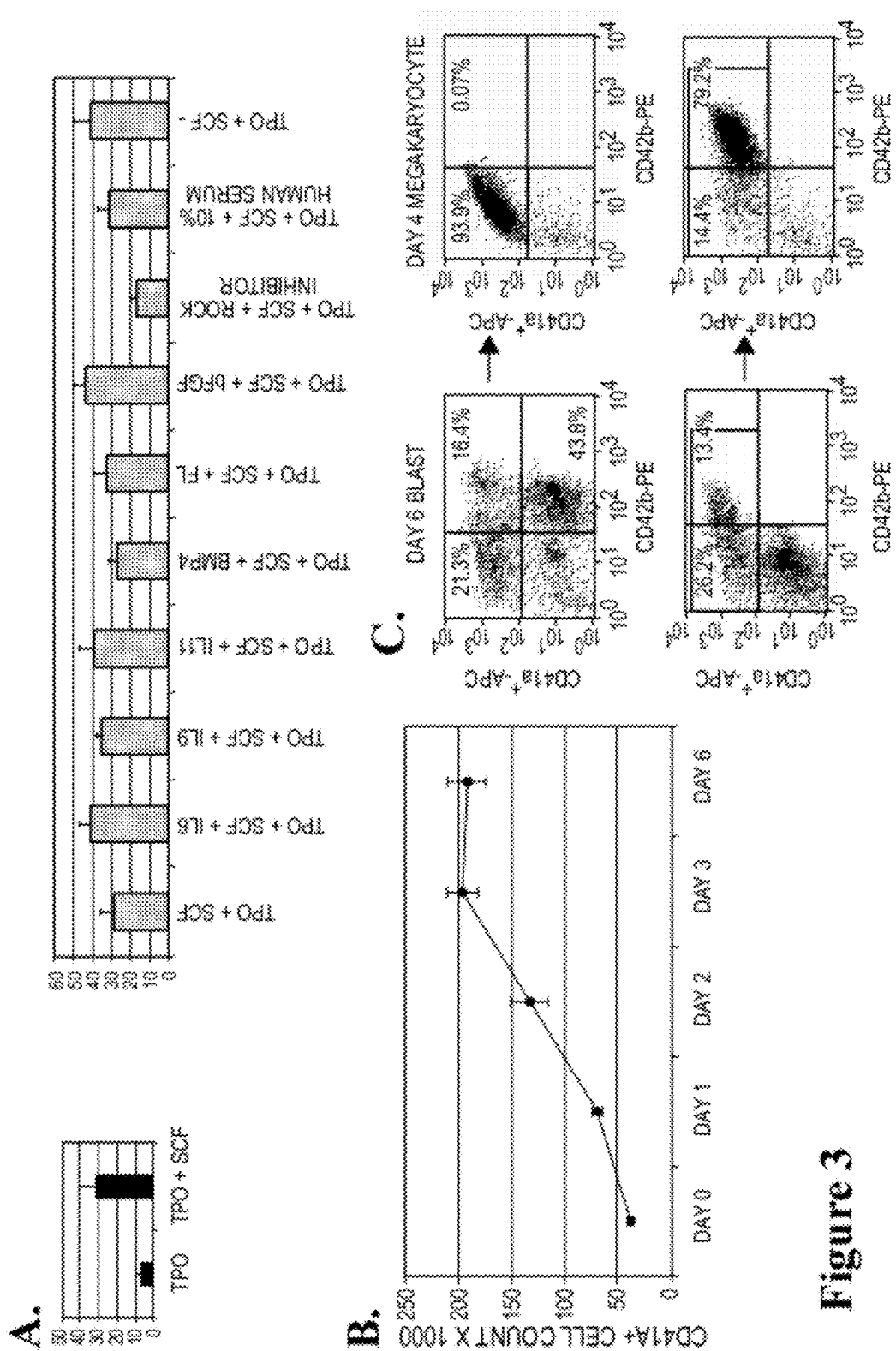
FIG. 3 depicts directed megakaryocyte differentiation from hESC derived blasts cells under stromal-free conditions in accordance with various embodiments of the present invention. A. The effects of TPO, SCF and other cytokines/factors on megakaryocyte differentiation and expansion. B. Time course experiment shows the expansion of CD41a+ megakaryocytes during 6 day culture. C. FACS analyses of day 6 blast cultures and day 4 MK cultures show the change of expression levels of CD41a, CD42b and CD235a lineage markers. While CD235a+ cells disappeared in MK culture, greater than 90% of live cells became CD41a+. A small number of CD41a+ cells were positive for CD42b in day 6 blast cultures (lower panel, left). By day 4 in MK culture, majority of CD41a+ cells also expressed high level of CD42b indicating maturation of megakaryocyte (lower panel, right).

Establishment of Defined Culture Conditions to Direct Megakaryocyte Expansion and Maturation from hESC Derived BCs In order to further direct the differentiation of megakaryocytes, day 6 to day 8 BCs from methylcellulose semi-solid cultures were harvested and then resuspended in serum-free media, i.e., Stemline II supplemented with cytokines for MK culture. The cell count of CD41a+ cells was used as readout to determine the expansion megakaryocytes during the suspension culture, which was calculated by multiplying the percentage of CD41a+(FACS) and total live cell count (Trypan blue exclusion). The initial tests showed that high concentration TPO (50 to 100 μg) alone was not sufficient to support the expansion of CD41a+ megakaryocytes from BCs. Adding SCF (20 ng/ml) in the media significantly increased the yields of CD41a+ megakaryocytes (FIG. 3A). A panel of cytokines and factors were also tested in order to achieve high purity and the total yield of megakaryocytes from BCs. These factors including IL9 and BMP4 were previously reported as megakaryocyte promoting factors in other systems[21;22].

As shown in FIG. 3A, addition of IL9 and BMP4 did not show obvious effects of improving the yields of CD41+ cells, comparing to TPO and SCF only. Certain factors, however, did slightly increase the percentage of CD41+ cells (not shown). IL 6, IL11, VEGF and bFGF all slightly increased the yields of megakaryocytes in 4 day liquid culture without additional feeding. However, mixing these factors together did not show a consistent synergistic effect (not shown). Additionally, the addition of serum or methylcellulose matrix to the cultures was also tried; these modifications did not significantly improve the yield of CD41 megakaryocytes. Of note, a specific ROCK signaling inhibitor (Y27632), which was shown to promote megakaryocyte endomitosis and proplatelet formation[23;24], was tested. Inclusion of 10 μM ROCK inhibitor during 4 day MK culture dramatically increased the percentage of polyploid cells (data not shown). However, it simultaneously reduced the CD41+ cell count at the end of 4 day culture; therefore it was excluded from the final MK culture conditions.

Based on results from initial tests, TPO 50 ng/ml, SCF 20 ng/ml and IL11 20 ng/ml are included in the MK culture media to achieve optimized megakaryocyte differentiation and expansion from BCs. IL11 was previously reported to enhance both the expansion and maturation of megakaryocytes[25;26]. FIG. 3B shows a time course experiment of liquid culture. Over a 6 day culture period, a five time increase in the cell number of CD41+ megakaryocytes was observed under the current conditions. FACS analyses were performed on day 6 BCS and day 4 MK cultures for two megakaryocyte markers CD41a, CD42b and erythroid marker CD235a. In MK culture, erythroid cells (CD235a+) die quickly in two to three days. In sharp contrast, CD41a+ megakaryocytes increased dramatically. By day 4 in MK culture, more than 90% live cells were expressing CD41a and approximately 80% of these cells were also positive for CD42b, which plays important functional roles in the maturing megakaryocytes (FIG. 3C)[27].

Example 14

Characterizations of Megakaryocytes Derived from BCs

Figure 4:
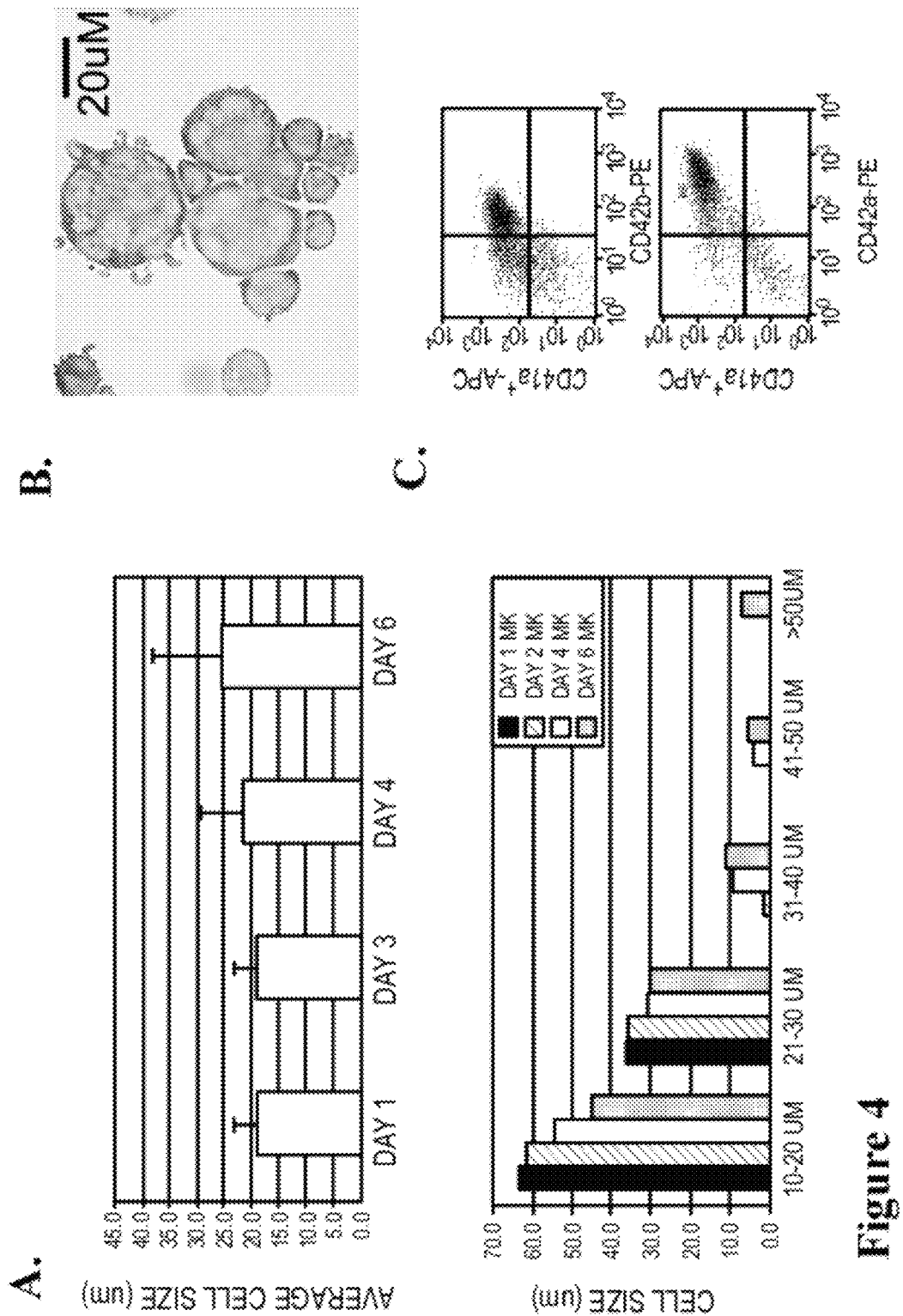
FIG. 4 depicts characterizations of in vitro generated megakaryocytes in accordance with various embodiments of the present invention. A. Time course experiment shows the increase of cell size (upper panel) and the change of cell size distribution (lower panel) during 6 day MK culture. The cell sizes (diameter) were measured using cytospin slides with Giemsa staining. B. Giemsa staining image shows polyploid megakaryocytes. C. FACS dot plots show the expression of both CD42b and CD42a megakaryocyte/platelet specific glycoproteins within CD41a+ megakaryocytes from day 6 MK culture. D. Immunofluorescent image shows the CD41 staining and vWF staining in polyploid megakaryocytes from day 4 MK cultures. E. RT-PCR results show the expression levels of transcription factors regulating erythro/megakaryopoiesis at different stages of in vitro MK generation. Total RNA were isolated from ES, day 4 EB, BCs (day 6 to day 8) and day 4 MKs with RNA easy mini-prep kit (Qiagen). 2 ug total RNA were used cDNA synthesis by using iScript kit (Biorad). GAPDH RT-PCR was done as controls for the amount of input cDNA for each sample. F. Representative phase contrast image shows the proplatelet forming megakaryocytes in day 4 MK culture.
Figure 4:
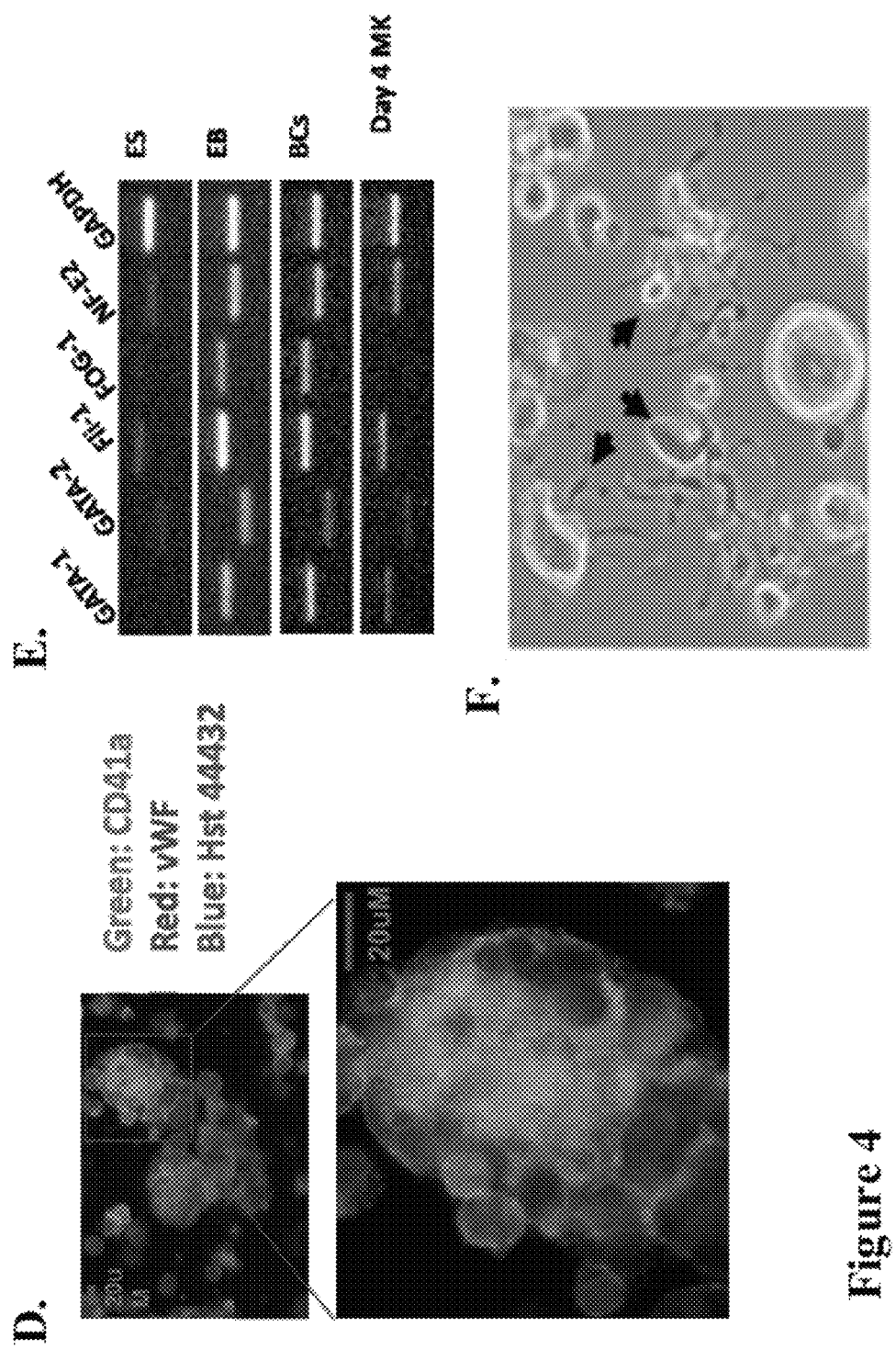

Consistent with the changes of cell surface markers indicating the differentiation and maturation of megakaryocytes, the average cell size gradually increased during MK culture. The maturing megakaryocytes became larger and more heterogeneous in cell sizes (FIG. 4A). In day 1 MK culture about 65% cells had a diameter of 10 to 20 µm. The rest of the cells were 20 to 30 µm. By day 6, more than 20% cells were larger than 40 micron in diameter in cytospin preparations. A small percentage of cells demonstrated phenotypes of polyploid cells in MK culture (FIG. 4B). In addition to CD42b (GP1balpha), glycoprotein CD42a (GPIX) was also highly expressed within the CD41a+ megakaryocytes from the MK cultures (FIG. 4C). Immunofluorescent staining for CD41 and vWF was also performed to examine the characteristic vWF expression in megakaryocyte cytoplasmic granules. As shown in FIG. 4D, large and polyploid cells with mature megakaryocyte phenotype were stained positive for CD41 and granular accumulation of vWF in cytoplasm was detected.

Furthermore, RT-PCR analysis was performed to examine the expression levels of critical transcription regulators including GATA1, GATA2, Fli1, FOG and NFE2 (FIG. 4E) for erythro/megakaryopoiesis. All these transcription factors were strongly induced at the embryoid body stage and showed sustained expression in the day 6 blast cultures. Interestingly, the RNA levels GATA2 and FOG were down regulated in day 4 MK cultures when BCs were directed toward megakaryocyte differentiation and maturation. However, the mechanistic implication of this observation has yet to be determined. RT-PCR results showed the expression of five erythroid-megakaryocytic transcription factors GATA1, GATA2, Flit, FOG1, and NF-E2 during ES, EB, BC and MK cultures.

Example 15

Expansion from hESCs to Megakaryocytes

All the hESC lines that were tested were able to generate megakaryocytes (defined as CD41a+) under the serum-free and stromal-free culture conditions, although the efficiencies among cell lines were variable. After the expansion from hESCs through EB (expansion 1.5 to 6 fold), blast (5 to 12 fold) and MK cultures (1.5 to 4 fold), the system is capable of producing up to 100 million of CD41a+ megakaryocytes from 1 million starting human ES cells. The capacity for megakaryocyte production is summarized for HUES3 and two clinical grade single-blastomere-derived hESC lines, MA01 and MA09 in Table 1.

TABLE 1

Generation of Megakaryocytes from hESCs
Percentages of CD41a+ cells from MK cultures were determined by FACS. Total fold expansion from hESC to megakaryocytes were calculated by multiplying the fold expansion at each step through EB, Blast and MK cultures. HuES3 experiment B is an actual count of MK cells from one million ES cells.

| hESC lines | Experiments | Fold expansion from |
|---|---|---|
| HUES3 | Experiment A | 111 |
|  | Experiment B | 96* |
|  | Experiment C | 30 |
|  | Experiment D | 21 |
|  | Experiment E | 37 |
|  | Experiment F | 16 |
| MA01 | Experiment | 16 |
| MA09 | Experiment | 113 |

Figure 5:
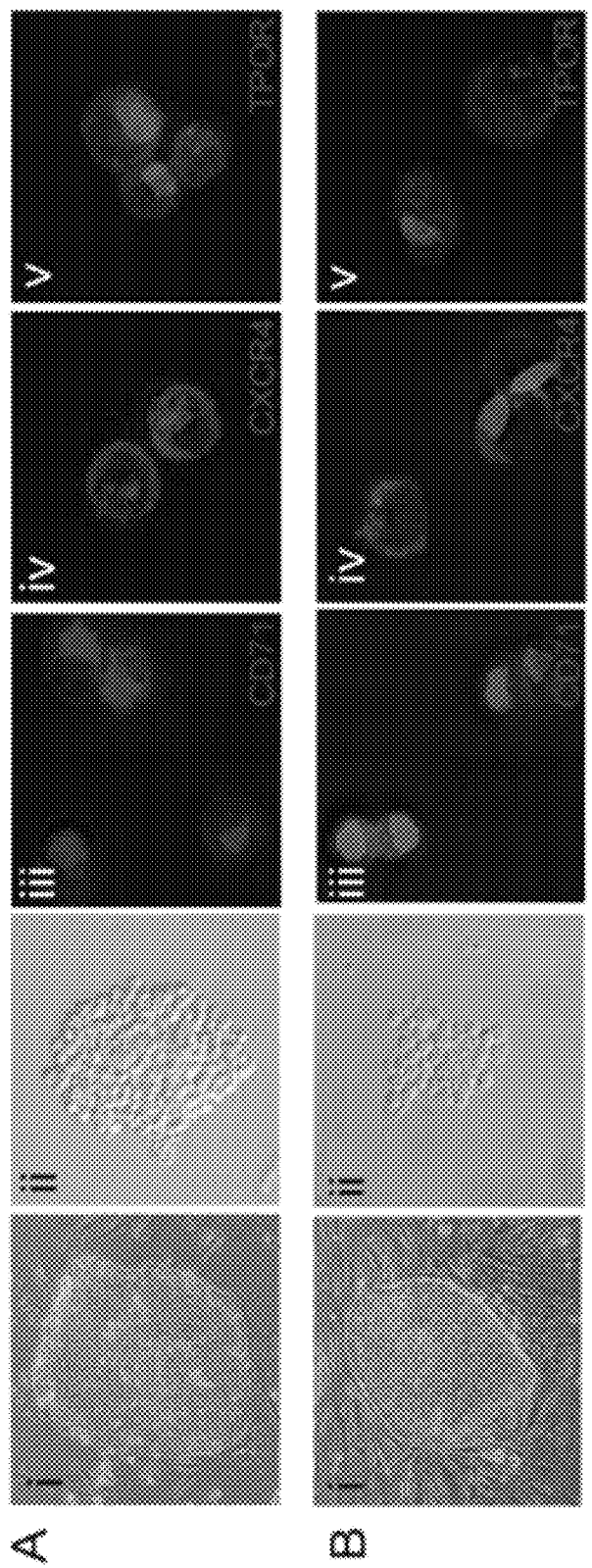
FIG. 5 depicts differentiation of hiPSCs and hESCs toward hemangioblasts/blast cells and hematopoietic cells in accordance with various embodiments of the present invention. A. Hemangioblasts/blast cells (ii, ×400) derived from hESCs (i, ×100) were stained with CD71 (×1000), CXCR4 (×1000) and Tpo receptor (×1000). B. Hemangioblasts/blast cells (ii, ×400) derived from hiPSCs (i, ×100) were stained with CD71 (×1000), CXCR4 (×1000) and Tpo receptor (×1000). C. Multiple types of hematopoietic colony-forming units (CFU) developed from hiPSC-blast cells 14 days after replating, ×100 for CFU-E, CFU-GM and CFU-Mk, ×40 for CFU-G. (D) Hemangioblast/blast cells derived from hiPSCs differentiated into endothelial cells (i, ×200); hiPSC derived endothelial cells formed vascular-like network on Matrigel (ii, ×40), expressed vWF (red) and CD31 (iii, green, ×400) as well as VE-Cadherin (iv, green) with LDL uptake capability (iv, red ×400).
Figure 5:
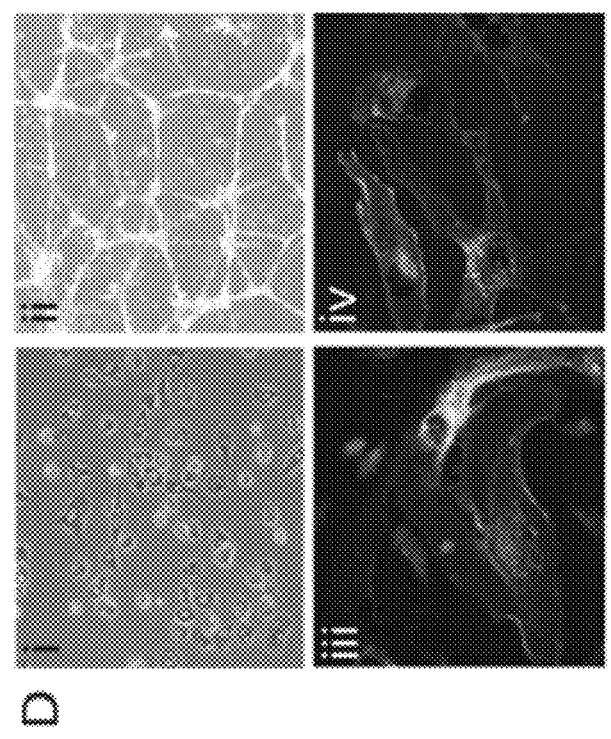
Figure 5:
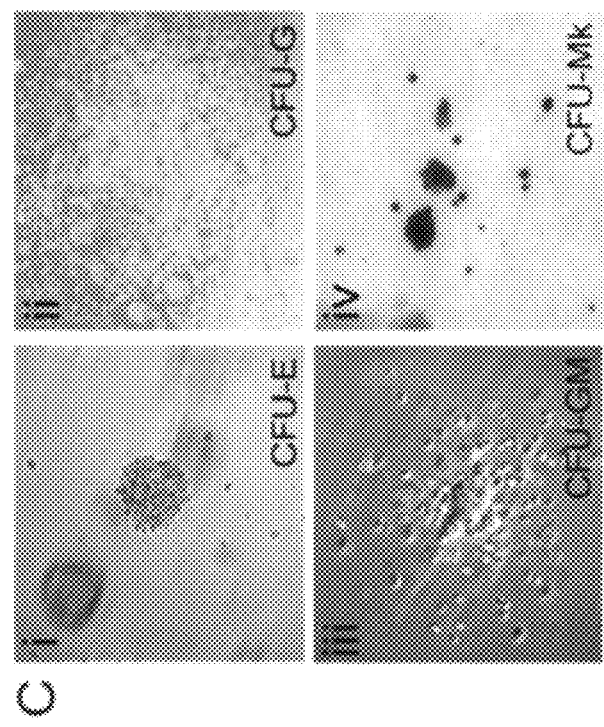

Example 16 hiPSCs are Capable of Differentiating Into Hemangioblasts/BCs, Hematopoietic and Endothelial Cells In Vitro The inventors achieved similar results using hiPSCs generated by the Thomson reprogramming method (lentiviral expression of Oct-4, Sox-2, Nanog, and Lin28). This includes cell lines IMR90-1, Foreskin-1-1, Foreskin-4-1 and Foreskin-4-3. Separately, hiPSCs generated by the Yamanaka reprogramming method (retroviral expression of Oct-4, Sox-2, Klf4, and c-Myc) performed similarly. This includes cell lines rv-hiPS01, rv-hiPS02, rvhiPS03 and rv-hiPS04. These hiPSC lines expressed the standard markers of pluripotency, and formed teratomas after inoculation in SCID mice as reported, and were all morphologically indistinguishable from hESCs (data not shown). Using the methods described herein, hiPSC lines were capable of generating BCs. First, hiPSCs were differentiated into EBs under conditions optimized for the development of BCs, and individual EB cells were plated in blast-growth/expansion medium (BGM) for the development of blast colony. EB cells from all hiPSC lines developed blast colonies six days after plating. Variable efficiencies were observed for the different hiPSC lines (Table 2). Nevertheless, as observed for BCs derived from hESCs (FIG. 5A), these BCs from hiPSCs expressed hemangioblast markers CD71, CXCR-4 and Tpo receptor (FIG. 5B), but majority of these BCs did not express CD31, CD34 and KDR as demonstrated by immunocytochemical analyses. After replating in hematopoietic colony-forming media supplemented with a spectrum of cytokines for 10 to 14 days, erythroid (CFU-E), myeloid (CFU-G and CFU-GM), and macrophage (CFU-M, not shown) hematopoietic cell colonies developed (FIG. 5C). BCs also formed CFU-MK with the potential to differentiate into megakaryocytes (FIG. 5C-iv). Furthermore, hiPSCs generated using viral-free vectors, such as transfection of reprogramming proteins Oct4, Sox2, Klf4, and c-Myc, demonstrate similar potential for BC development, MK and platelet generation. These results clearly demonstrate that hiPSCs generated with different combinations of reprogramming factors using different delivery systems (Lentivirus, Retrovirus, transfection) are capable of differentiating into hemangioblasts, hematopoietic and endothelial lineages under serum-free conditions.

TABLE 2

Differentiation efficiencies of human induced pluripotent stem cells (hiPS)

| | hiPSCs | | | | | | | |
|---|---|---|---|---|---|---|---|---|
| | Thomson Method (Oct-4, Sox-2, Nanog, Lin28) | | | | Yamanaka Method (Oct-4, Sox-2, Nanog, Lin28) | | | |
| Sources Cell Lines | IMR90 | Foreskin 1-1 | Foreskin 4-1 | Foreskin 4-3 | Rv-siPS01 | Rv-siPS02 | Rv-siPS03 | Rv-siPS04 |
| BC Efficiency | ++* | ± | ± | ± | ± | ± | ± | ± |
| CFU Efficiency | + | ± | ± | ± | ± | ± | ± | ± |

*For every 100,000 EBs cells plated, (±) represents results of mostly 0 colonies or occassionally obtaining colonies under 10; (+) represents results of constantly obtaining low number of colonies (10 to 30); (++) represents modest efficieincy yield up to 50 blast colonies.

Example 17 hESCs Derived Megakaryocytes Generate Functional Platelets on OP9 Stromal Cells Starting from day 4 in MK culture, a small number (approximately 1 to 2%) hESCs derived megakaryocytes were consistently observed to form proplatelet-like processes under microscope (FIG. 4F). This observation suggests that megakaryocytes generated under stromal-free system are capable of going through the terminal differentiation process.

Recently, Takayama et al. described a stromal cell OP9 based co-culture system for producing functional ES derived platelets (ES-PLTs)[16]. The inventors decided to test the megakaryocytes on this OP9 system as a proof of principle to show that the cells are functionally capable of making platelets. Megakaryocytes generated (derived from HUES3, MA01 and MA09) from MK cultures were plated onto mitotically arrested OP9 cells in the same media supplemented with TPO 100 ng/ml, SCF 50 ng/ml and Heparin 25 U/ml as described in the original report. Proplatelet forming cells (PFCs) and platelet-like particles (ES-PLTs) showed up within 4 days post plating on OP9 stromal layer. ESP-LTs were collected from culture media every two days from day 6 to day 12. From 1 million hESC derived MKs, approximately 2 to 5 hundred thousand ES-PLTs can be recovered from culture during this period of time. The low ES-PLT production efficiency than previously reported could be a result of drastic change of culture conditions. Also, co-culture with OP9 did not significantly increase the polyploidy of plated megakaryocytes, which could also explain the low platelet yield/megakaryocyte. Nonetheless, ES-PLTs recovered from the OP9-coculture were further tested for functionalities that are crucial for normal blood platelets.

Example 18

Thrombin Activated ES-PLTS has Functional Integrin Receptor Binding Activity Integrin-mediated platelet aggregation is essential for thrombus formation in vivo. In circulation, platelets adhere to injured vessel walls via its adhesive receptors. The primary adhesion initiates a signaling cascade leading to the activation of platelet integrin αIIbβ3, leading to platelet stable adhesion, aggregation and thrombus formation. Platelet agonists, such as thrombin, activate the ligand binding function of integrin αIIbβ3. The binding of its main ligand fibrinogen mediates integrin-dependent platelet stable adhesion and aggregation. Activation of αIIbβ3 also mediates the integrin outside-in signaling leading to platelet cytoskeleton reorganization and spreading.

Figure 6:
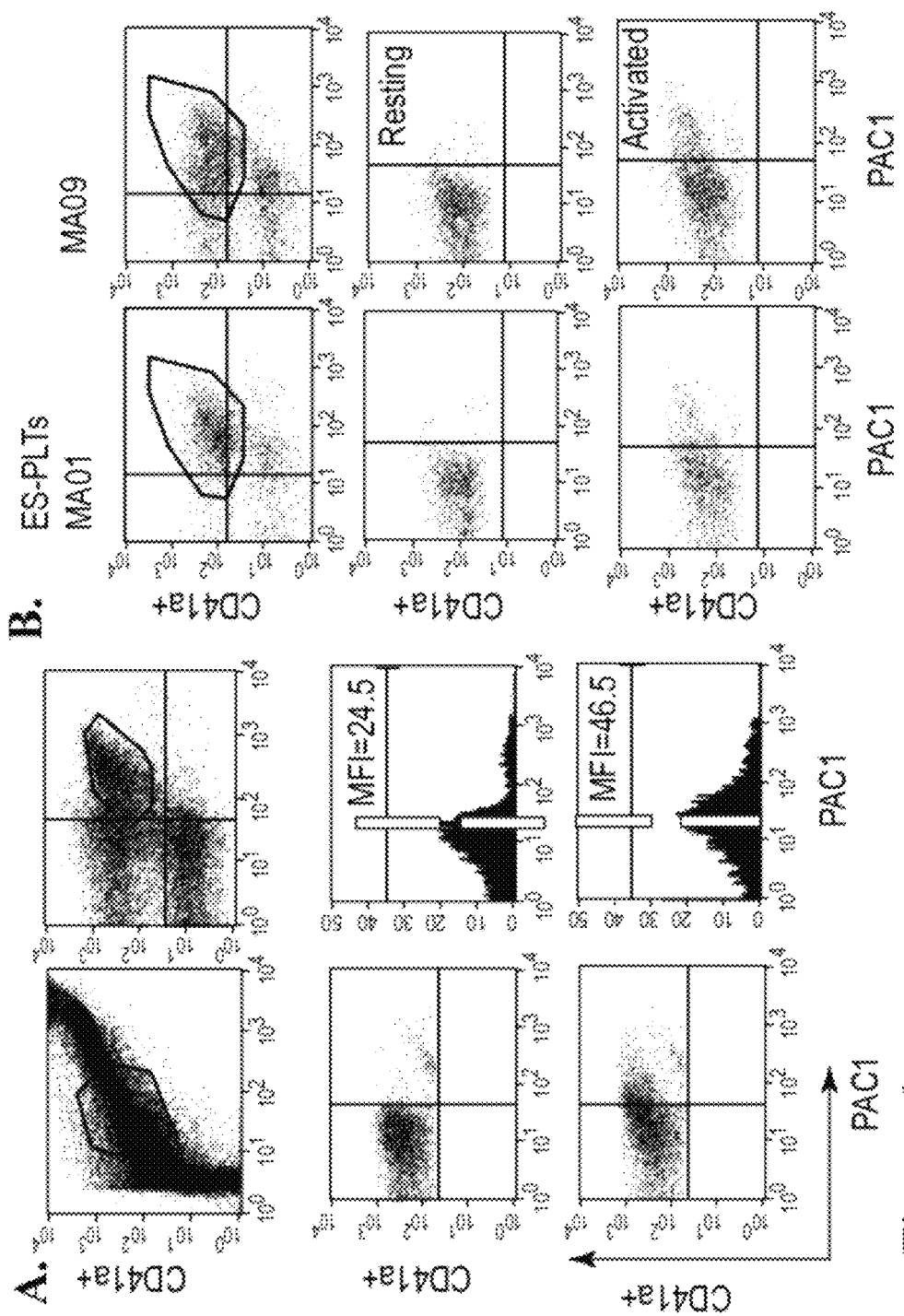
FIG. 6 depicts generation of functional ES derived platelets (ES-PLTs) in accordance with various embodiments of the present invention. A. Dot plots show forward scatter (FSC) and side scatter (SSC) characteristics ES-PLTs derived from OP9 co-culture (top left). Gating was set based on human blood platelets. Top right panel show the expression of CD41a (y axis) and CD42b (x axis) on ES-PLTs. Comparing to resting ES-PLTs (middle panels), thrombin (1 u/ml) treated ES-PLTs showed increased PAC1 binding. Mean Fluorescent Intensity increased approximately two fold in thrombin treated ES-PLTs. B. ES-PLTs derived from MA01 and MA09 clinical grade hESCs also show PAC1 binding in response to thrombin treatment.

ES-PLTs generated from OP9 co-cultures were tested for activation by major agonist of platelets, thrombin. Integrin αIIbβ3 activation was examined by the binding assay with FITC conjugated PAC-1 monoclonal antibody, which only binds to the activated form of integrin αIIbβ3 receptor by FACS analyses. ES-PLTs resuspended in Tyrode's buffer were incubated with a cocktail of anti-human CD41a (integrin αIIb) antibody, CD42b and PAC-1 antibodies. ES-PLTs expressing both CD41a and CD42b glycoproteins on their surface were then gated for PAC-1 binding activity. Upon thrombin stimulation, PAC-1 binding was increased in thrombin treated ES-PLTs compared to the resting controls. This result indicated that ES-PLTs were responsive to the stimulation from platelet agonist (FIG. 6A). ES-PLTs were derived from three hESC lines including two clinical grade hESC lines, MA01 and MA09. All three lines were able to give rise to ES-PLTs capable of PAC-1 binding in response to thrombin stimulation (FIG. 6B).

Integrin outside-in signaling functional property in ES-PLTs was further assessed by spreading assay on immobilized fibrinogen on glass slides. Slides were stained with anti-human CD41a antibody and DAPI to identify platelets. Similar to human plasma platelet control, ES-PLTs adhered and spread on fibrinogen-coated surface and demonstrated the rearrangement of F-actin filaments similar to functional platelets. RGDS peptide, which blocks the fibrinogen binding to platelet integrin receptor, abolished the adhesion and spreading of ES-PLTs on fibrinogen-coated surface, indicating that the spreading is integrin dependent. In the absence of agonists, some platelets showed incomplete spreading on fibrinogen with mainly filopodia formation. When stimulated with platelet agonists, ADP or thrombin, both control plasma platelets and ES-PLTs showed enhanced lamellipodia and actin stress fiber formation (FIG. 7A).

Example 19

ES-PLTs are Able to Participate in Micro-Thrombus Formation

To examine their ability to form agonist-induced aggregation, a critical function of platelets, ES-PLTs were labeled with green fluorescence dye and mixed with plasma-derived platelets. In response to thrombin stimulation under stirring conditions, platelet microaggregates were observed under a phase contrast and fluorescence microscope. Fluorescence labeled hESC-platelets incorporated evenly into those microaggregates together with human plasma-derived platelets. The thrombin induced platelet aggregation was inhibited by the integrin antagonist, RGDS, indicating it is integrin-dependent (FIG. 7B). These results demonstrated that the ES-PLTs were able to work together with blood platelets in the agonist-induced microaggregate formation. In summary, these results indicated that the ES-PLTs derived from the culture system are functionally comparable to human peripheral blood platelets; and these ES-PLTs can be stimulated by physiological platelet agonists.

Example 20

Expression of HLA Class I on ES-PLTs

Human peripheral platelets synthesize and express class I human leukocyte antigens (HLA-ABC) that might contribute to immunity related refractive platelet transfusion[28]. Therefore, the expression of HLA class I on ES-PLTs was also examined by flow cytometry. Normal plasma-derived platelets showed a high level of HLA-ABC expression. ES-PLTs showed a comparable expression level (mean fluorescent intensity) of HLA class I. It has been reported that in addition to the de novo synthesis of HLA in platelets, soluble HLA antigens can also be absorbed from plasma[29]. Platelets derived from hESC in culture conditions may avoid plasma containing HLA antigens from other blood cells, thus reducing the frequency of platelet alloimmunization.

Example 21

Large Scale Generation of MKs from hESC-Derived Hemangioblasts/BCs

Figure 8:
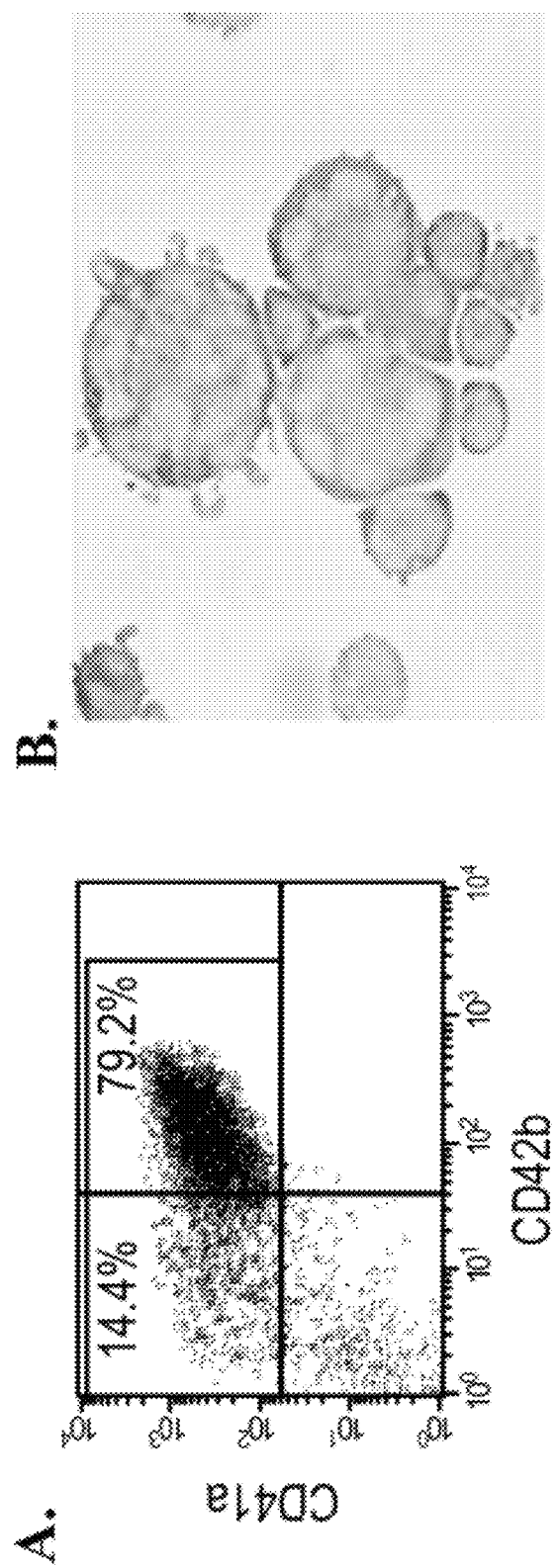
FIG. 8 depicts characterization of megakaryocytes and platelets generated from hESCs in accordance with various embodiments of the present invention. A. FACS analysis of cells on the expression of CD41a and 42b antigens from day 4 MK cultures; B. Giemsa staining image shows polyploid megakaryocytes (100×). C. Immunofluorescence image shows CD41, vWF and DAPI staining in polyploid MKs from day 4 cultures (upper panel 40×, lower panel 100×). D. FACS analysis of MKs for DNA contents; E. Representative phase contrast image shows the proplatelet forming megakaryocytes in day 4 MK culture (40×), F. FACS dot plots show forward scatter (FSC), side scatter (SSC) characteristics (left panel) and the expression of CD41a and CD42b (right panel) on platelets derived from hESCs. Gating was set based on human blood platelets. G. PAC1 binding assay on resting (left panel) and thrombin (1 U/ml) treated hESC-platelets (right panels).
Figure 8:
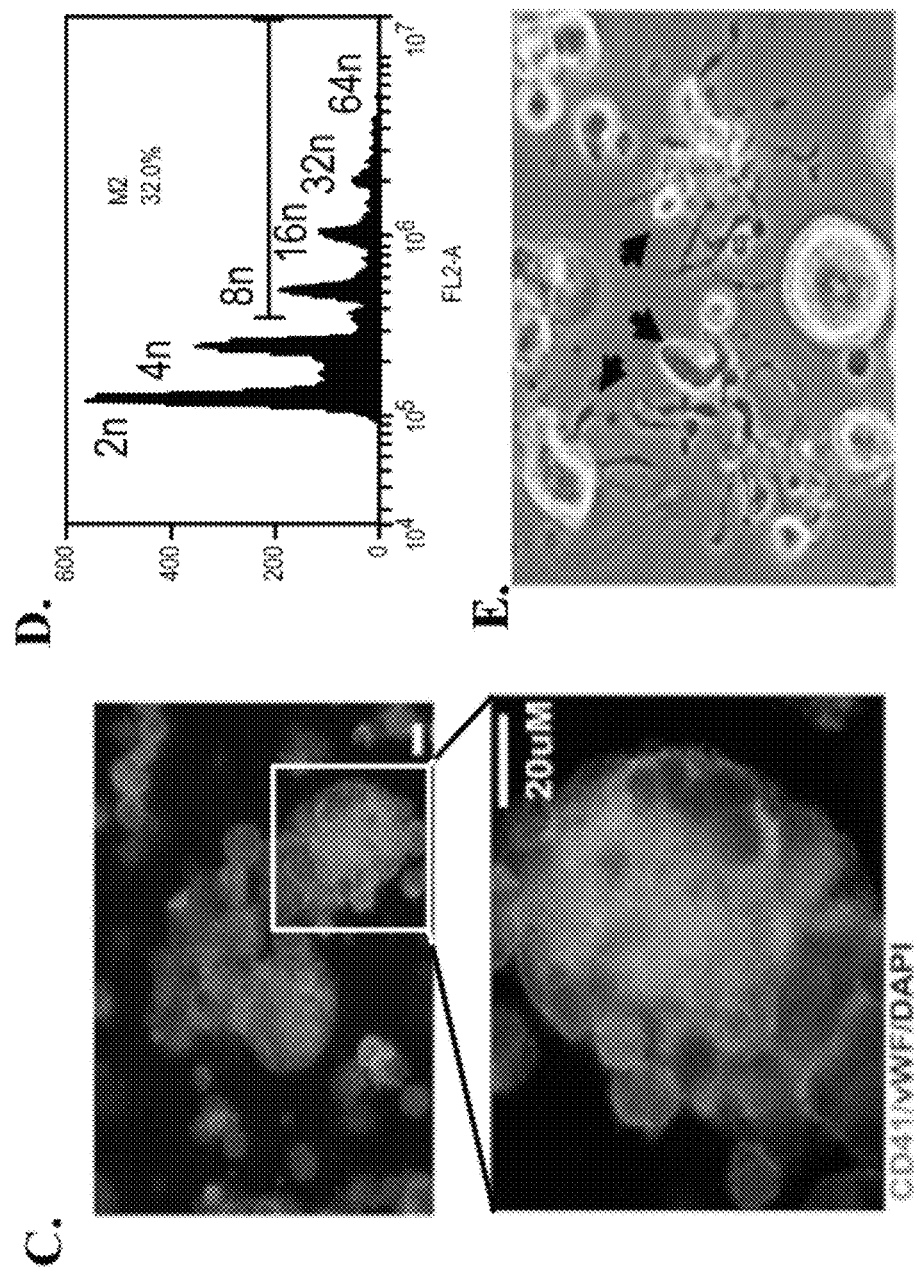
Figure 8:
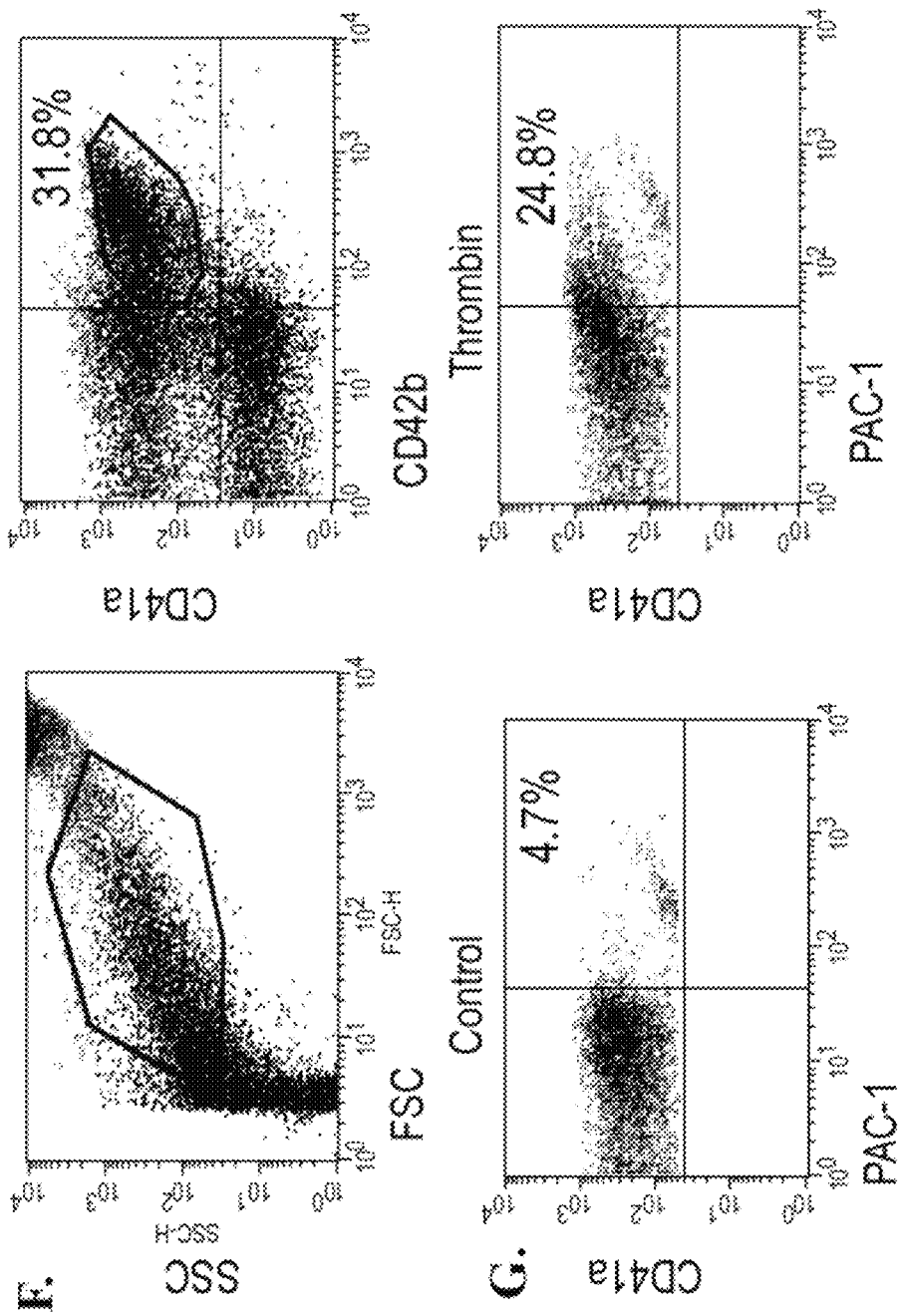

Experiments were performed to determine if hESCderived BCs could also be induced to differentiate into MKs. A five-fold increase in CD41+ MKs was obtained after blast cultures were differentiated for 6 days in serum free Stemline II medium containing TPO, SCF, and IL-11. FACS analyses also showed a rapid decrease of CD235a+ cells (erythroid cells), but a dramatic increase of CD41a+ and CD42b+ cells (MKs) during the initial phase of differentiation. By day 4, over 90% of the cells expressed CD41a, and approximately 80% of the cells were positive for CD42b (which plays an important functional role in the maturation of MKs)[27] (FIG. 8A). In addition to CD42b, glycoprotein CD42a was also highly expressed on the surface of CD41a+ MKs (data not shown). By day 6, over 20% of the cells were larger than 40 μm in size, and >30% were polyploid with DNA content greater than 4N (FIGS. 8B and 8D). Immunofluorescent staining for CD41 and vWF on large and polyploid cells showed characteristic granular accumulation of vWF in the cytoplasm with CD41-positive membrane staining (FIG. 8C), confirming the cells were mature MKs.

All hESC lines tested (WA07 [H7], HuES-3, MA01, and MA09) generated MKs under these serum- and feeder-free culture conditions, although variable efficiencies were observed (Table 3). In eight separate experiments, the total expansion of cells from hESC to CD41a+MK cells ranged from 30 to 111-fold and 18- to 113-fold for HuES-3 and MA09 hESC lines, respectively; up to $6\times10^8$ CD41a+ MKs were generated per 6-well plate of MA09 hESCs ($\approx1.0\times10^7$ hESCs, Table 3). The overall efficiency is approximately two magnitudes higher than previously published methods[16].

TABLE 3

Generation of Megakaryocytes from hESCs via Hemangioblasts

| hESC | Experiments | Generated CD41+ MK (×10⁶) | Fold Expansion from hESC |
|---|---|---|---|
| HuES-3 | 1 | 7 | 30 |
|  | 2 | 15 | 111 |
|  | 3 | 114 | 95 |
|  | 4 | 118 | 104 |
| MA09 | 1 | 22 | 113 |
|  | 2 | 53 | 29 |
|  | 3 | 191 | 18 |
|  | 4 | 604 | 53 |

CD41+ MK cell counts from cultures were calculated by multiplying total numbers of live cells (trypan blue exclusion) and the percentages of CD41a+ cells (FACS analyses). Total fold expansion from hESC to MKs were calculated by multiplying the fold expansion at each step through EB, BC and MK cultures since not all the EB cells or BCs were used for subsequent cultures.

Example 22

Generation of Functional Platelets from hESC-MKs

Starting from day 4 in serum- and feeder-free MK cultures, approximately 1-2% of MKs were observed to form proplatelet-like cellular processes (FIG. 8E). To examine whether functional platelets were generated under feeder-free conditions, the inventors examined CD41a/CD42b expression on hESC-derived platelets (hESC-PLTs) by FACS analyses. Our results showed that majority of hESC-PLTs (gated according the Forward Scatter and Side Scatter patterns of blood platelet controls) generated under feeder-free conditions expressed CD41a. However, less than 5% of these hESC-PLTs were CD42b positive. Recent studies showed that the metalloproteinase inhibitor GM6001 significantly increased the expression of CD42b on mouse ESC-derived platelets[35]. Supplement of GM6001 (100 μM) during late stage of human ESC-PLTs differentiation increased CD41a and CD42b double positive hESC-PLTs to about 15%. The function of feeder-free generated hESC-PLTs was assessed by integrin dependent spreading assay on immobilized fibrinogen and vWF. Anti-human CD41a antibody and DAPI staining were used to identify platelets. Feeder-free generated hESC-PLTs were able to spread on fibrinogen and vWF-coated surfaces (FIG. 11), indicating these hESC-PLTs are functional in vitro.

OP9 or C3H 10T1/2 mouse stromal cells were shown to support in vitro platelet biogenesis. It was tested whether co-culture with OP9 stromal cells facilitated the production of functional platelets from hESC-MKs. MKs generated from HuES-3, MA01 and MA09 cells were plated onto mitotically arrested OP9 cells in the same media supplemented with TPO, SCF, and heparin as previously described[16]. Proplatelet-forming cells and hESC-PLTs appeared within 4 days post plating on OP9 stromal layers. hESC-PLTs were collected from the culture media every two days from day 6 to day 12, and analyzed for CD41a and CD42b expression. In contrast to hESC-PLTs generated under stromal-free conditions, a majority of CD41a+ hESC-PLTs also expressed CD42b (FIG. 8F, right panel).

Figure 9:
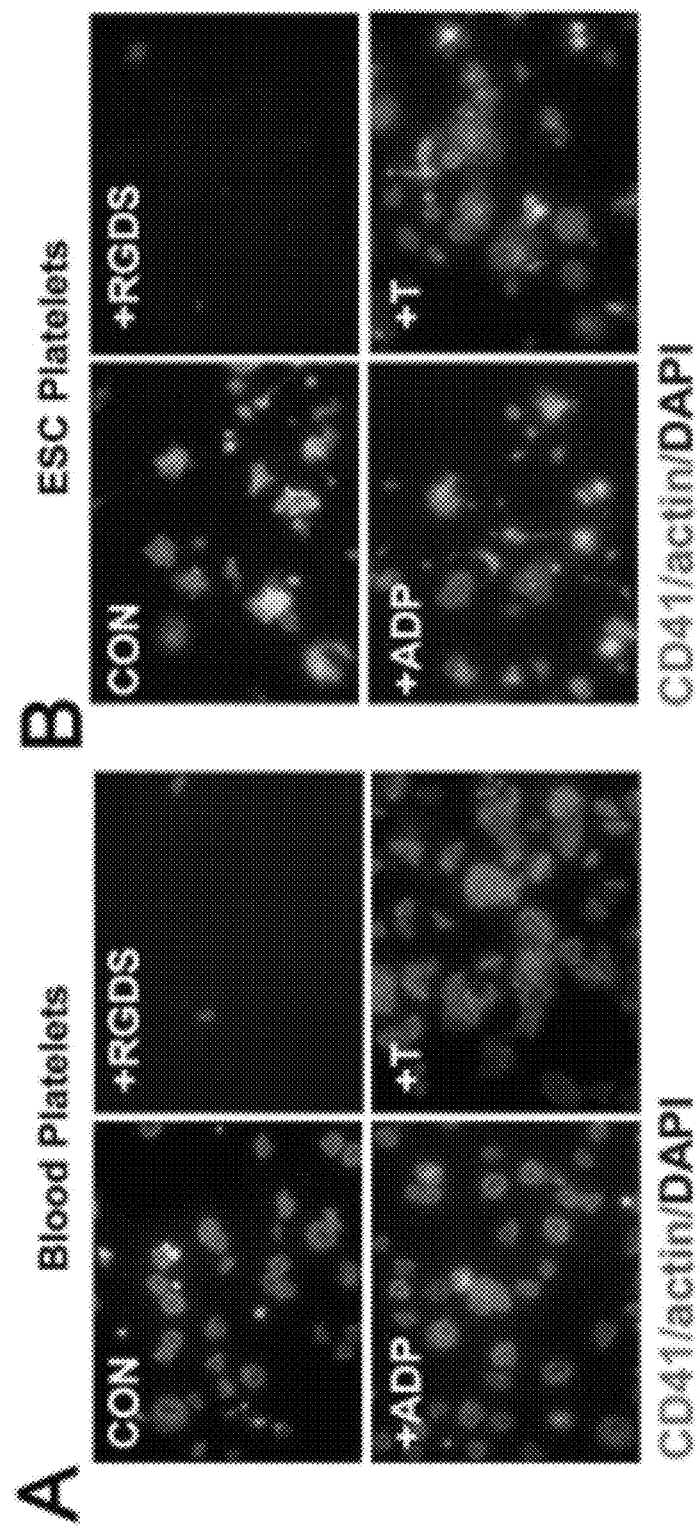
FIG. 9 depicts functional characterization of platelets generated from hESCs in accordance with various embodiments of the present invention. A and B. Microtiter chamber slides were coated with 100 µg/mL fibrinogen. Human blood platelets (A) and hESC-platelets (B) were allowed to spread for 90 minutes. Adherent platelets were stained with Alexa Fluor 568 phalloidin, FITC conjugated antihuman CD41a antibody and DAPI, and photographed under a fluorescence microscope (100×). Platelets were also treated with RGDS (1 mM), ADP (20 µM) or thrombin (T, IU/ml) as indicated. C and D. Micro-aggregate formation assay. Same numbers of PKH67 (green) labeled human blood platelets (C) or hESC-platelets (D) were mixed with unlabeled blood platelets to form aggregates under the stimulation of thrombin (0.5 U/ml). Phase contrast (left panels) and fluorescent images (center panels) were merged (right panels) to show the participation of labeled blood platelets (C, right panel) and hESC platelets (0, right panel) into micro-aggregates. E and F. hESC-platelets ($1.5 \times 10^7$/ml, E) and blood platelets ($1.5 \times 10^7$/ml, F) were resuspended in platelet-depleted plasma. Thrombin (2 U/ml) and $CaCl_2$ (10 mM) were added to the platelet suspensions to induce clot formation/retraction (E and F, left panels). Plasma alone was used as negative controls. Clot cryo-sections were immunostained with anti-human CD41 and anti-human fibrin antibodies followed by secondary rhodamine-conjugated anti-rabbit IgG and FITC conjugated anti-mouse IgM antibodies, respectively. Images were taken under a fluorescence microscope (20×).
Figure 9:
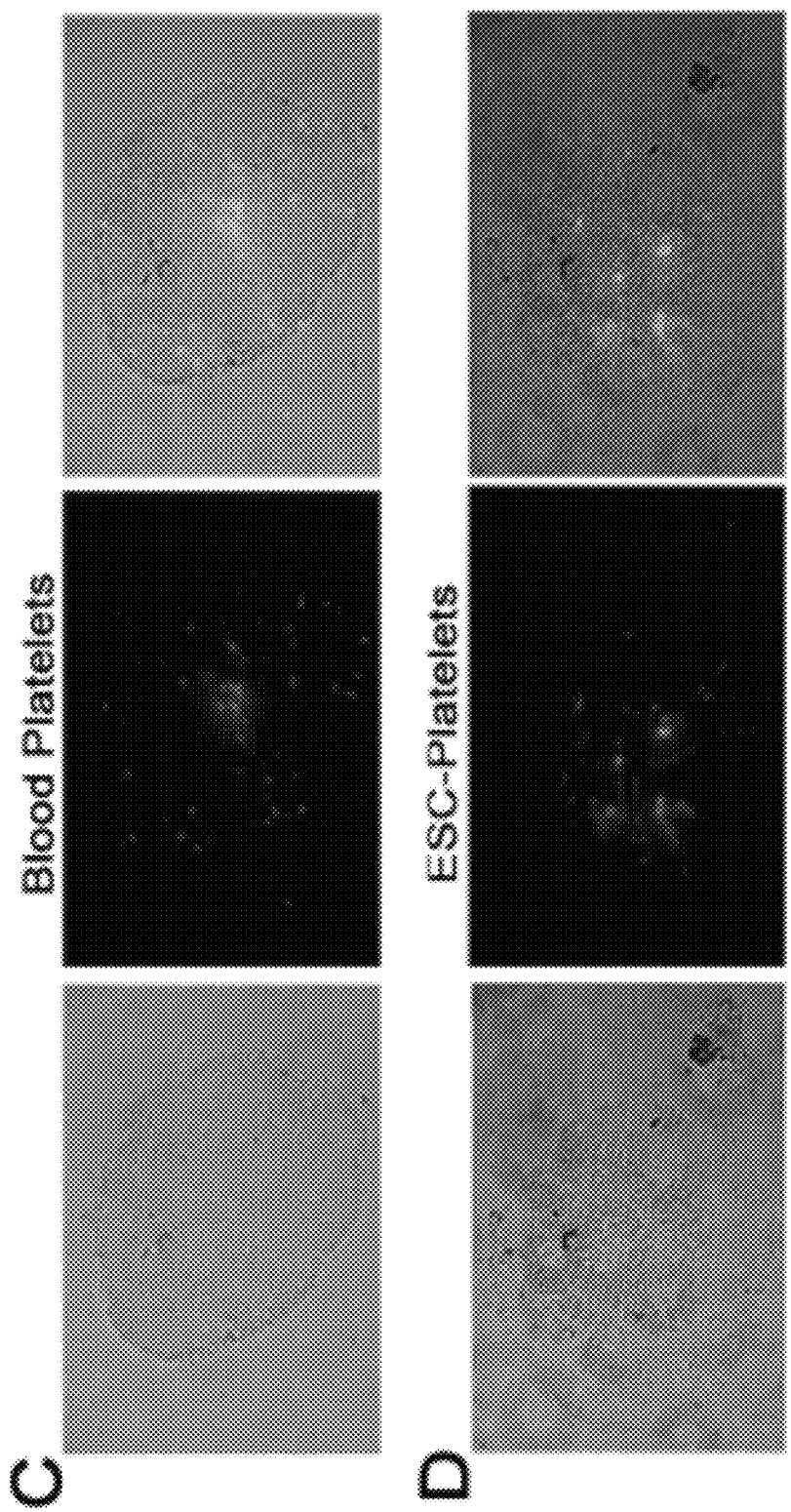
Figure 9:
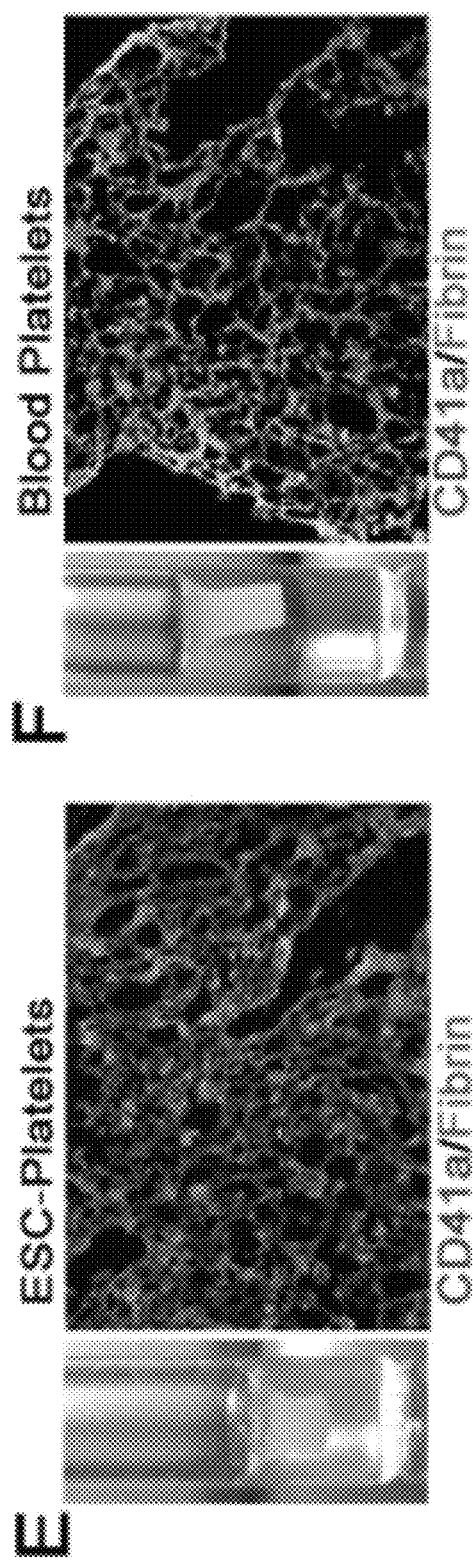
Figure 12:
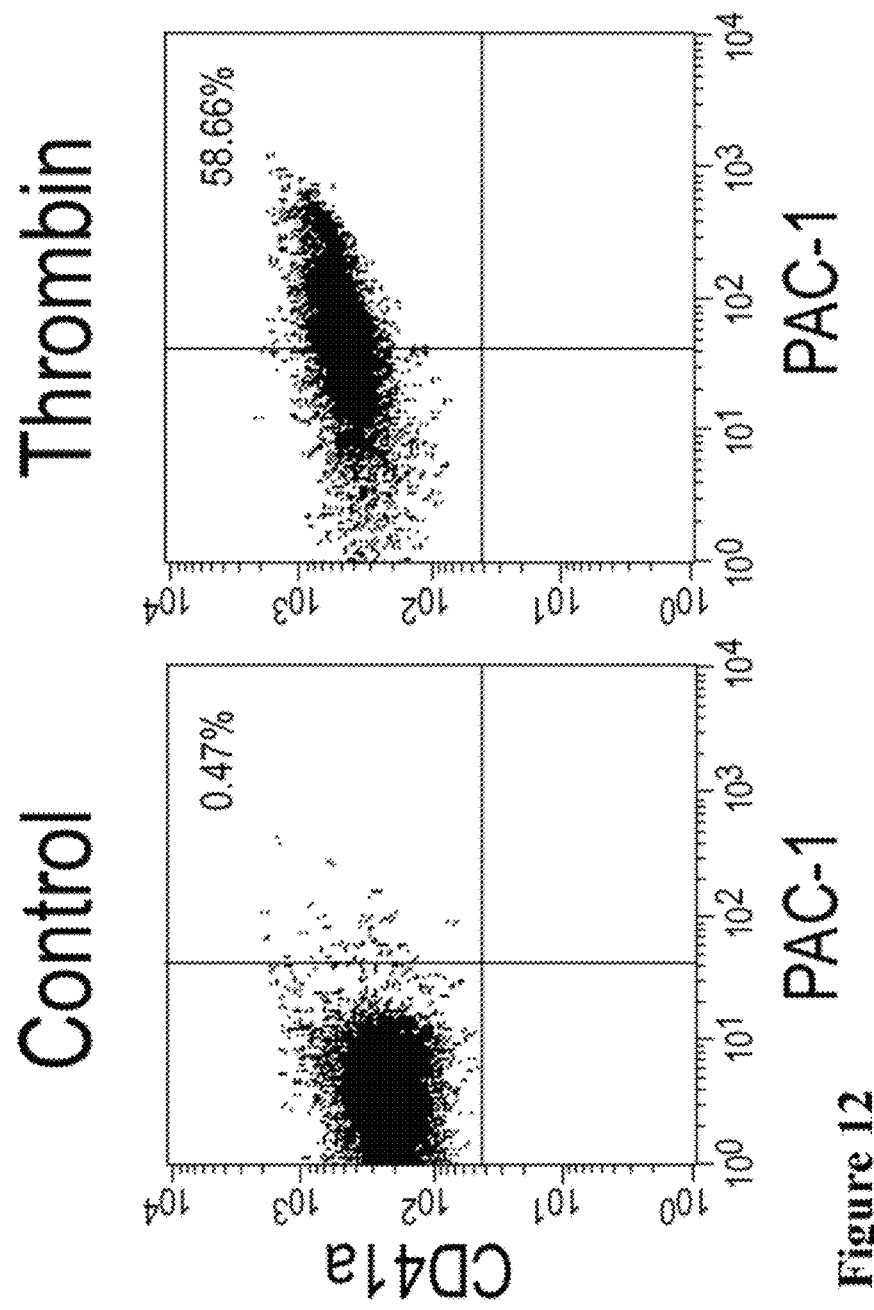
FIG. 12 depicts PAC-1 binding assay for blood platelets in accordance with various embodiments of the present invention. Blood platelets were treated with (right) or without (left) thrombin (1 U/ml), then PAC-1 binding was performed by FACS analysis.
Figure 13:
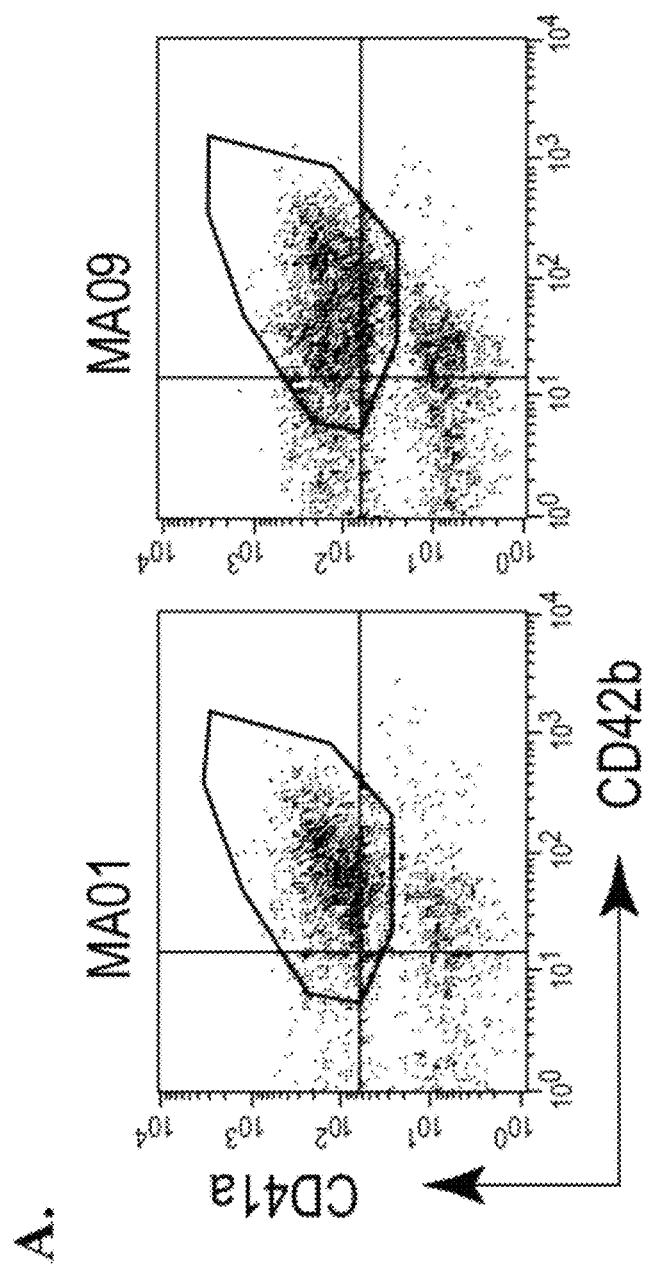
FIG. 13 depicts characterizations of hESC-platelets generated from different hESC lines in accordance with various embodiments of the present invention. A. CD41a and CD42b expression on hESC-platelets derived from clinical grade MA01 and MA09 hESC cells. B. In response to thrombin treatment (1 U/ml), MA01 and MA09 hESC-derived platelets show increased PAC-1 binding (lower panels) comparing to resting controls (upper panels). C. hESC-platelets display HLA-ABC expression comparing to IgG isotype control staining. Histograms of FACS analyses show HLA expression in hESC-platelets. Blood platelets were used as control (left).
Figure 13:
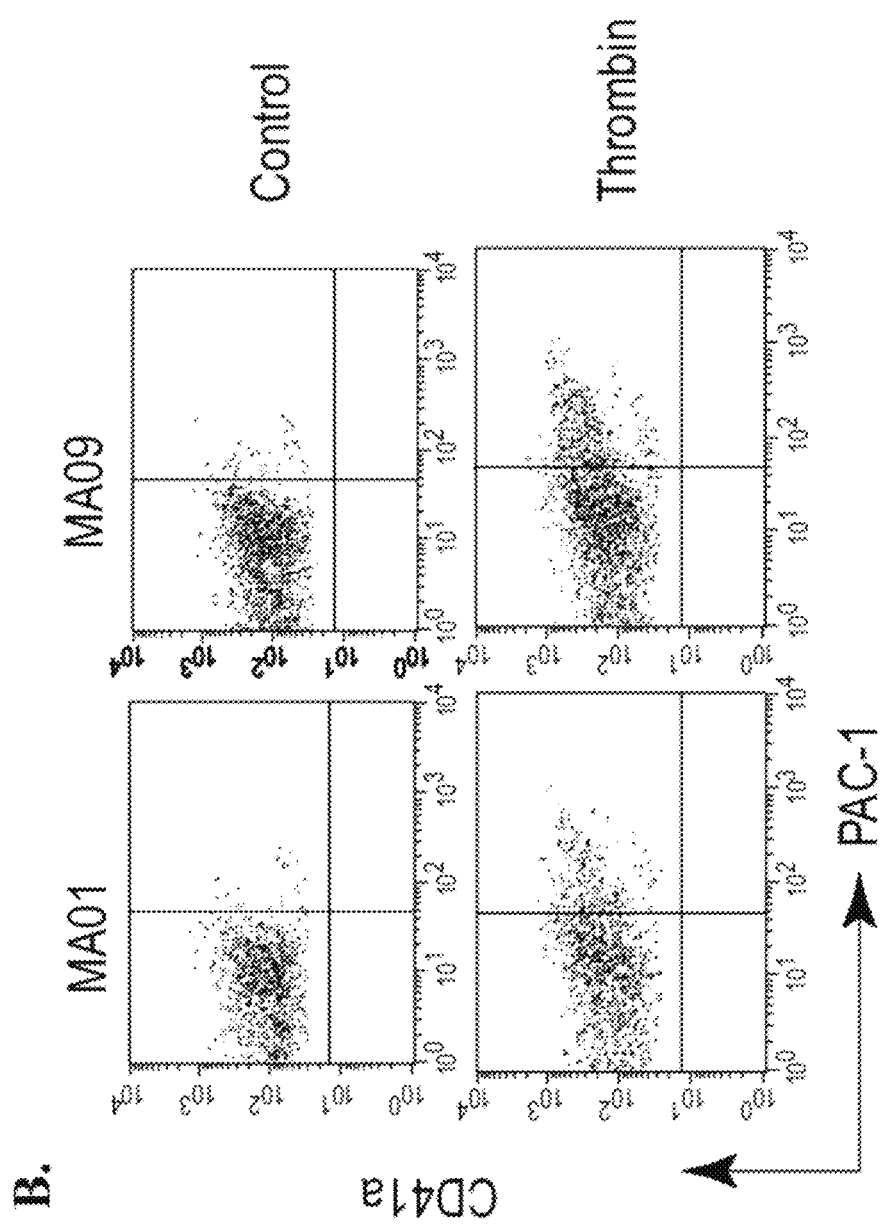
Figure 13:
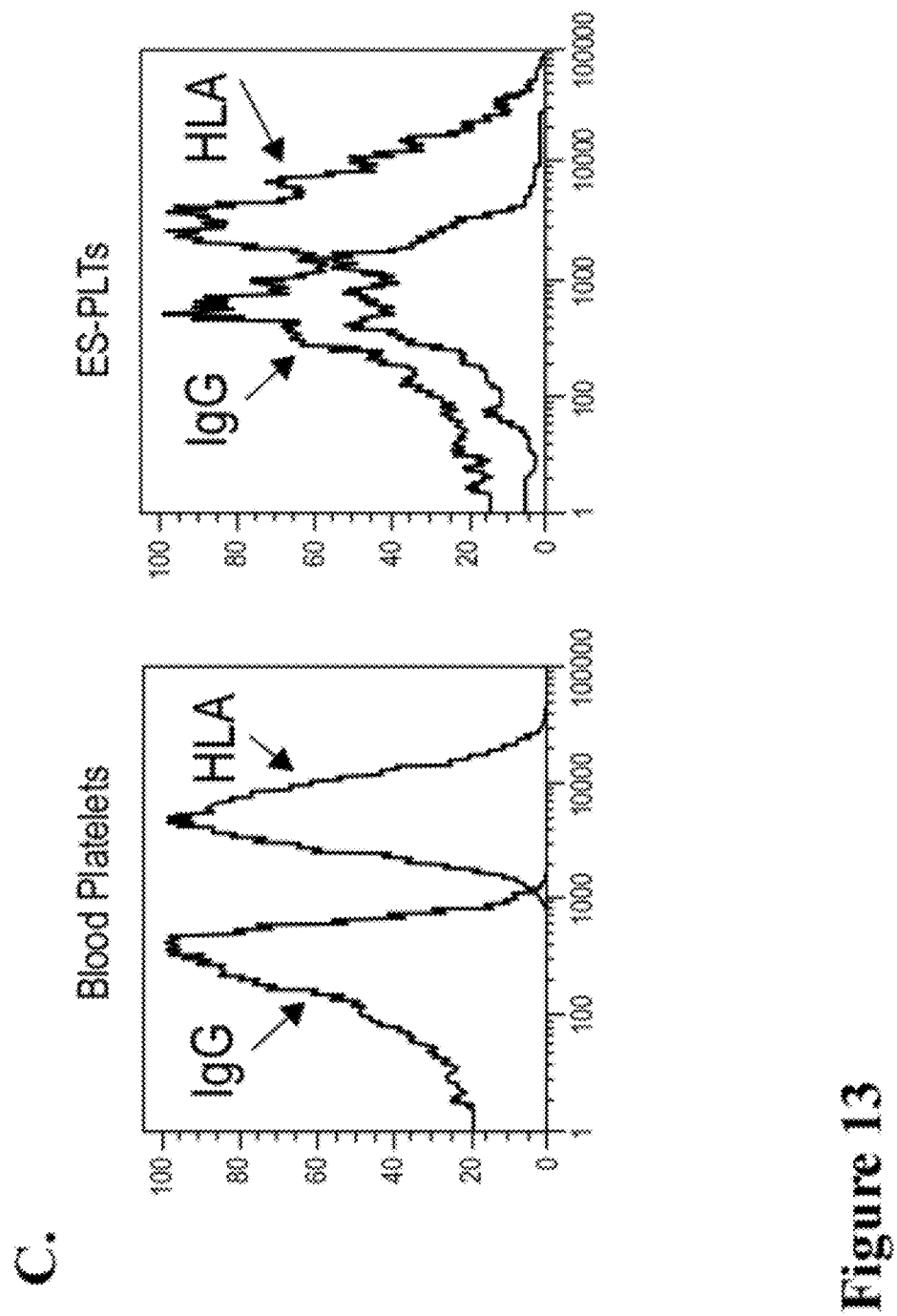

Similar to hESC-PLTs generated under feeder-free conditions, hESC-PLTs produced with OP9 cell co-culture adhered and spread on fibrinogen—(FIG. 9B) and vWF-coated surfaces. RODS peptide, which blocks the fibrinogen binding to the platelet integrin receptor, abolished the adhesion and spreading of both human blood platelets and hESC-PLTs on fibrinogen-coated surfaces (FIG. 9B). Phalloidin staining showed the formation of F-actin stress fibers in hESC-PLTs stimulated with ADP and thrombin (FIG. 9B), similar to that in human blood platelets (FIG. 9A). The size of hESC-PLTs generated under feeder-free condition or on OP9 stromal cells are slightly larger than human blood platelets, which is similar to platelets generated with mouse ES cells in vitro[35].

hESC-PLTs generated from HuES-3 cells in OP9 co-cultures were also tested for activation by a major agonist of platelets, thrombin. PAC-1 monoclonal antibody, as a fibrinogen mimetic, only binds to the activated form of integrin αIIbβ3 receptor. Upon thrombin stimulation, a PAC-1 binding assay was performed on hESC-PLTs generated from OP9 co-culture. Approximately five-fold increase in PAC-1 binding in thrombin treated hESC-PLTs comparing to resting controls (FIG. 8G). Although the increase of PAC-1 bind after thrombin stimulation is weaker than that of peripheral platelet controls (24.8% of hESC-PLTs vs. 58.6% of blood platelets, FIG. 12), but is similar to platelets generated from hESCs previously reported by Takayama et al. [16] hESC-PLTs derived from two clinical grade hESC lines, MA01 and MA09, also expressed CD41a and CD42b antigens (FIG. 13A), and were able to bind PAC-1 in response to thrombin stimulation (FIG. 13B). hESC-PLTs also expressed HLA class I antigens on their surface (FIG. 13C).

Example 23 hESC-PLTs Participate in Micro-Aggregate Formation and Clot Formation/Retraction Platelet adhesion to injured vessel walls initiates a signaling cascade leading to the activation of platelet integrin αIIbβ3. Activated integrin mediates platelet aggregation and thrombus formation[45]. To examine their ability to form agonist induced aggregation, a critical function of platelets, hESC-PLTs were labeled with green fluorescence dye and mixed with human blood platelets. In response to thrombin stimulation under stirring conditions, the formation of micro-aggregates by hESC-PLTs and blood platelets was demonstrated using phase contrast and fluorescence microscopy (FIG. 9D). The labeled hESC-PLTs incorporated into micro-aggregates together with human blood platelets. The distribution of hESC-PLTs in these micro-aggregates was similar to that of the same number of blood platelets labeled with fluorescent dye (FIG. 9C). These results demonstrate that hESC-PLTs work together with human blood platelets in agonist-induced micro-aggregate formation.

At vascular injury sites, activated platelets interact with fibrin generated from plasma fibrinogen, leading to thrombus formation and clot retraction[46]. To examine their ability to facilitate clot formation and retraction, hESC-PLTs were suspended in platelet-depleted plasma and thrombin was added to induce clot formation and retraction. No clot formed in platelet-depleted plasma without the supplementation of additional platelets even with more than 1 hour thrombin stimulation. In contrast, addition of hESC-PLTs to platelet-depleted plasma led to clot formation and retraction in less than 30 minutes after thrombin stimulation (FIG. 9E, left panel). Immunofluorescent staining of cryo-sections of hESC-PLT clots showed mesh-like networks that were stained positive for both fibrin and CD41a (FIG. 9E, right panel), similar to clot sections formed with human blood platelets (FIG. 9F). These results indicate that hESC-PLTs promote fibrin clot formation and possess integrin αIIbβ3 dependent contractile ability to form compact platelet plugs.

Figure 10:
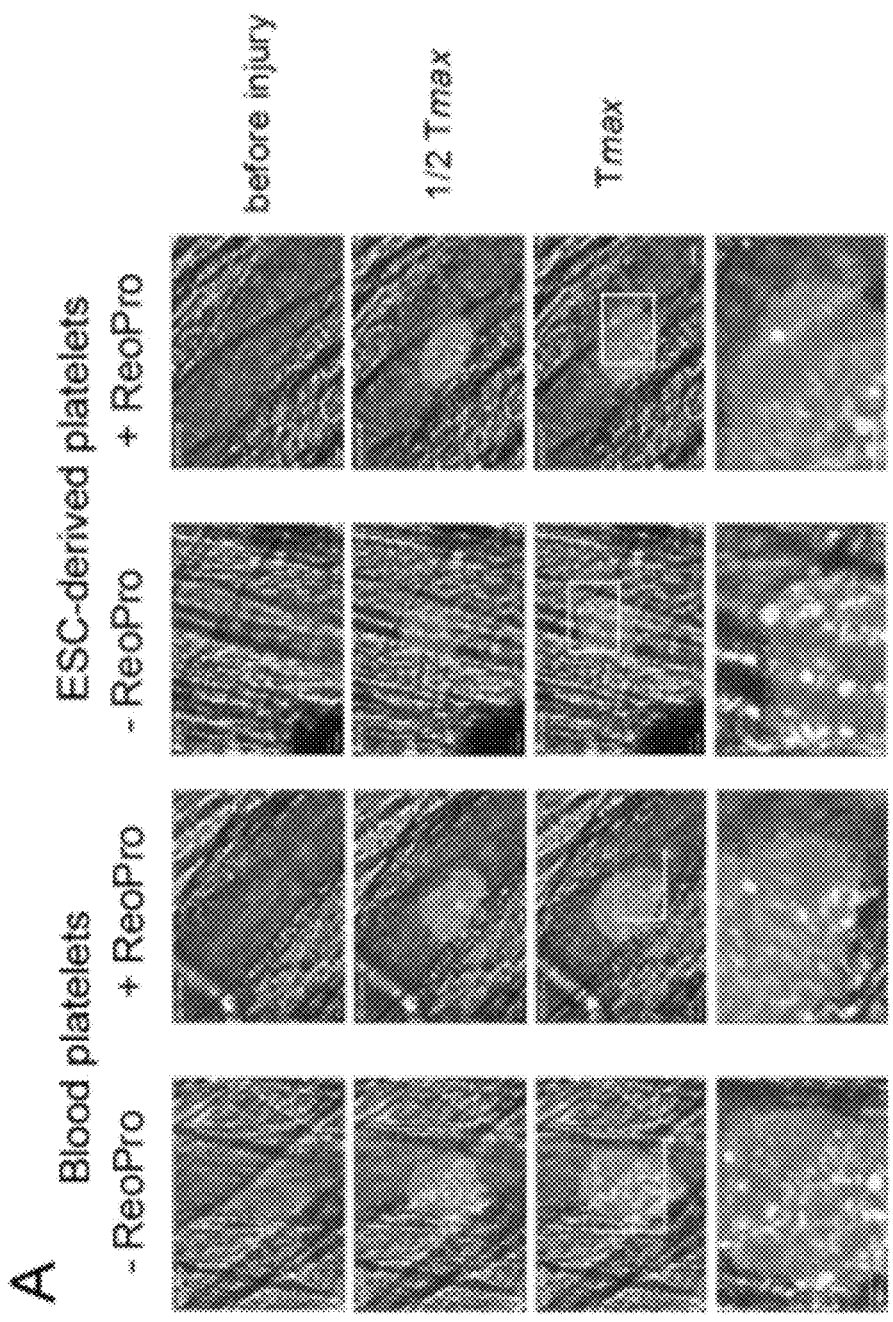
FIG. 10 depicts the incorporation of hESC-PLTs into the developing mouse platelet thrombus at the site of laser-induced arteriolar injury in live mice in accordance with various embodiments of the present invention. Calcein AM-labeled human blood platelets or ESC-derived platelets, 50-100 µl ($5-10 \times 10^5$ platelets), were infused through a femoral artery cannulus immediately after laser induced vascular injury. The developing mouse platelet thrombus was monitored by infusion of Dylight 649-labeled anti-CD42 (0.05 µg/g body weight). After generation of 2-3 thrombi, the labeled platelets were pretreated with ReoPro, 20 µg for $2 \times 10^6$ human platelets in 200 µl, and were infused after the vessel injury in the same mouse. Another 2-3 thrombi were generated. Data were collected for 3 minutes following vessel injury. A. Representative fluorescence images are shown at three time points (0, ½ Tmax, and Tmax) following vascular injury. Magnified images of the area within the white rectangle are shown at the bottom. Bar=10 µm. B and C. The number of labeled human platelets circulating into the microvessel (B) and incorporated into the developing mouse platelet thrombus at the site of vessel injury (C) was counted over 3 minute after vascular injury. Data represent mean±S.E.M. (n=5-8 thrombi in 3 mice). *P<0.05 and **P<0.01 versus a control, Student t-test.
Figure 10:
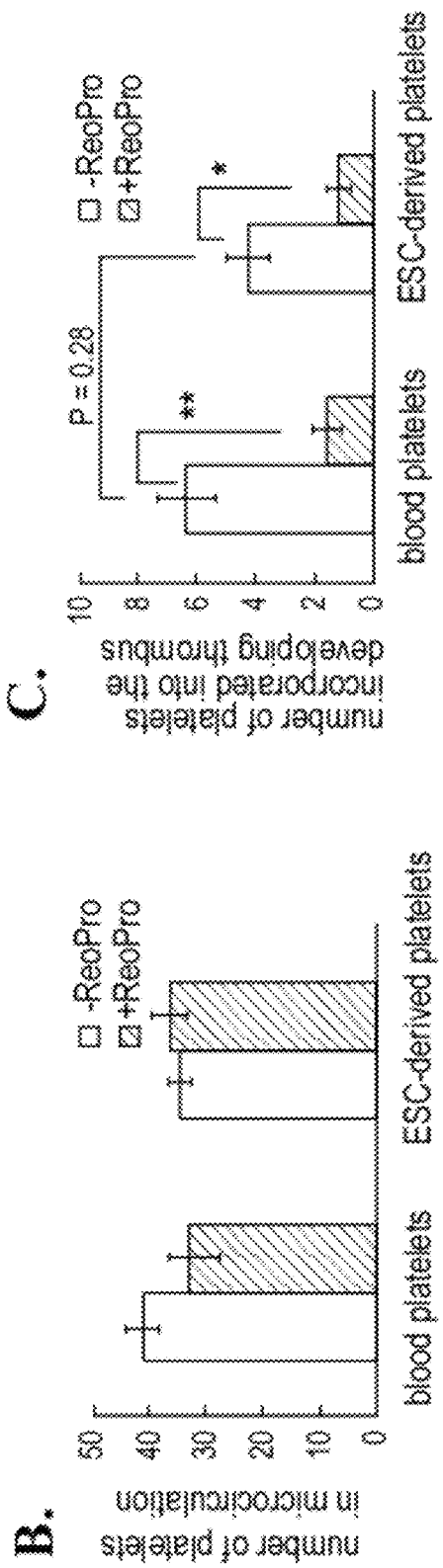

Example 24 hESC-PLTs are Incorporated into the Developing Platelet Thrombus at the Site of Laser-Induced Arteriolar Injury in Living Mice To determine if hESC-PLTs are functional in vivo, the inventors performed fluorescence intravital microscopy in living mice. The cremaster muscle arteriole was injured by micropoint laser ablation. Mouse platelet thrombus formed rapidly with a Tmax of 70-95 second after vascular injury as described previously[47]. When human peripheral platelets, $5-10 \times 10^5$, were infused after injury, 41.0±2.8 circulating platelets were detected in the microcirculation (FIG. 10B). Among them, 6.4±1.1 platelets were incorporated into the developing mouse platelet thrombus at the site of vascular injury at a Tmax (73 second) after vascular injury (FIGS. 10A and 10C, video 1 (not shown)). To confirm that the incorporation of human blood platelets into the developing mouse platelet thrombus is mediated by αIIbβ3 integrin, human platelets were pretreated with ReoPro (a Fab fragment of a human-murine chimeric monoclonal antibody which binds to αIIbβ3 integrin on human platelets and inhibits its function)[48] prior to infusion. The number of circulating platelets was not significantly affected by ReoPro (32.4±4.4, FIG. 10B), whereas the number of human platelets binding to the developing platelet thrombus was significantly reduced by treatment with ReoPro to 1.6±0.5 at a Tmax (67 second) after vascular injury (FIGS. 10A and 10C, video 2 (not shown), P<0.01). These results indicate that human platelets bind to the developing mouse platelet thrombus at the site of vascular injury, and that such binding is mediated by αIIbβ3 integrin. ReoPro did not affect mouse platelet thrombus formation at the site of vascular injury.

When $5-10 \times 10^5$ hESC-PLTs were infused after vascular injury, 34.8±1.7 circulating platelets were detected in the microcirculation (FIG. 10B). Among them, 4.3±0.7 platelets bound to the growing mouse platelet thrombus at the site of vascular injury at a Tmax (72 second) after injury (FIGS. 10A and 10C, video 3 (not shown)). The number of human blood platelets and hESC-PLTs incorporating into the developing mouse platelet thrombus at the injury site was not statistically significant (P=0.28). Pretreatment of hESC-PLTs with ReoPro significantly reduced the number of platelets incorporated into the mouse platelet thrombus to 1.2±0.4 at a Tmax (99 second) after vascular injury (FIGS. 10A and C, Supplemental video 4, P<0.05). These results indicate that hESC-PLTs, like normal control blood platelets, are functional at the site of vascular injury in vivo.

Example 25

Animals

Male wild-type mice (C57BL/6, 6-8 week-old) were purchased from Jackson Laboratory (Bar Harbor, Me.). The University of Illinois Institutional Animal Care and Use Committee approved all animal care and experimental procedures.

Example 26

Generation of MKs from hESCs Via Hemangioblasts/BCs

Hemangioblast/BC generation from hESC lines (HuES-3, H7 [WA07], MA01, and MA09) was performed as previously reported[17:20]. BCs from day 6 to 8 cultures were purified and plated (1 to 5×10$^5$/ml) in Stemline II media supplemented with 50 ng/ml TPO, 20 ng/ml SCF and 20 ng/ml IL-11 (Peprotech) to induce BC differentiation toward MKs. Half of the MK culture media was replaced with fresh media every 2 or 3 days. Platelets generation from MKs were performed under feeder-free condition or co-culture with OP9 or C3H 10T1/2 stromal cells. For feeder-free condition, MKs from day 4 to 6 MK cultures were collected and resuspended in IMDM medium supplemented with 100 ng/ml TPO, 50 ng/ml SCF and 25 U/ml sodium heparin as described[16], and refreshed every 2 days. Platelets were collected from day 4 to day 12 for analyses. GM6001 (100 µM) was added in late differentiation culture for some experiments. For co-culture experiments, OP9 or C3H 10T1/2 stromal cells were maintained in α-MEM with 15% fetal bovine serum (Hyclone). Confluent OP9 or C3H 10T1/2 cells were treated with 100 ng/ml mitomycin-C the day before co-culture. Cells were gently washed twice with PBS and recovered over night in OP9 culture media prior to co-culture. MKs from day 4 to 6 MK cultures were collected and plated on OP9 or CH1/2 stromal cells with medium as described above. Platelets were collected from day 4 to day 12 for analyses.

Example 27

FACS Analysis

Cells from blast cultures or MK cultures are monitored routinely by flow cytometry analyses on FACSCalibur (Becton Dickinson) or Accuri C6 Cytometer (Accuri Cytometers). Fluorochrome-conjugated antibodies for lineage markers, CD41a, CD42a, CD42b and CD235a (BD Biosciences) were used to characterize MK and erythroid lineages. Antibodies were freshly prepared (1:100 dilution for CD42a and CD42b antibodies; 1:250 dilution for CD41a antibody; 1:2000 for CD235a antibody) in PBS buffer with 5% fetal bovine serum (FBS). Typically 1 to 2×10$^5$ cells were used for antibody labeling. Cells were stained in a 100 µl antibody cocktail for 1 hour on ice, then washed twice with buffer, and resuspended in 250 µl buffer supplemented with 1 µg/ml propidium iodide. To detect the expression level of HLA-ABC, platelets were incubated with a fluorescein isothiocyanate (FITC)-conjugated anti-human HLA-ABC antibody or FITC-conjugated mouse immunoglobulin G (IgG) as a control. The samples were then analyzed with FACSCalibur, and data analyzed using Cellquest or Flowjo software. Cell sorting was performed on a BD FACSAria system at the UMASS Medical School Core Facility. Sorted cells were collected by centrifugation at 1000 rpm for 10 minutes and resuspended in appropriate media for colony formation assays. For polyploidy analysis, cells from day 4 MK culture were fixed in 70% ethanol for 2 hours. Cells were then washed once in PBS buffer before staining with 20 µg/ml propidium iodide (Sigma), 20 µg/ml RNase A (Sigma) in PBS buffer overnight at 4° C. Cellular DNA content was analyzed on an Accuri C6 cytometer.

Example 28

Cytospin Preparation, Giemsa and Immunofluorescent Stains

Cells (1 to 2×10$^4$) from either blast cultures or MK cultures were cytospun on polylysine coated slides (Wessco). Slides were used for either Wright-Giemsa (Sigma) or immunofluoroscent staining. Anti-CD41 (DAKO, 1:100) and anti-vWF (DAKO, 1:200) antibodies were used for identifying MKs in cytospin preparations. All incubations were performed at room temperature. Cells were blocked with animal-free blocker (Vector Laboratories) for 30 minutes, incubated with primary antibodies for 1 hour, and then washed three times with PBS. Subsequent incubation and washing was performed in dark. Cells were incubated with secondary antibodies (1:200 each) for 30 minutes, and washed again three times in PBS. DAPI (1 µg/ml) in PBS was used to stain the nuclei DNA for 5 minutes followed by additional 3×PBS washes. Slides were then mounted and examined under Olympus BX51 fluorescence microscope (MVI, Avon, Mass.). Fluorescent images were captured using a QICAM Fast camera (QImaging, Surrey, BC, Canada) and analyzed with Q Capture Pro version 5.1 software (Media Cybernetics Inc., Bethesda, Md.). Phase contrast live cell images were captured using a Nikon microscope, PAXCAM digital camera and PAX-it software.

Example 29

Preparation of Human Blood Platelets and hESC-Derived Platelets

Human platelets were isolated as previously described[49]. Briefly, human platelet-rich plasma was prepared by centrifugation of sodium citrate-treated human blood at 200 g for 20 min. The supernatant was collected and centrifuged at 700 g for 10 min in the presence of 0.5 µM PGE1 and 10% sodium citrate buffer. The pellet was resuspended with HEPES-Tyrode buffer (12 mM NaHCO$_3$, 138 mM NaCl, 5.5 mM Glucose, 2.9 mM KCl, 0.42 mM NaHPO$_4$, 10 mM HEPES, 1 mM CaCl$_2$, 1 mM MgCl$_2$) containing 0.15 µM PGE1, and centrifuged at 800 g for 5 min. The pellet was resuspended in RPMI1640 containing 0.1% fatty acid-free bovine serum albumin, 2 mM CaCl$_2$, and 1 mM MgCl$_2$. Final suspensions of washed platelets were adjusted to 1×10$^7$ platelet/ml. Approval to obtain blood samples was obtained from the University of Illinois-Chicago review board. Informed consent was provided. In some experiments, human blood samples were also obtained from commercial source (AllCells, Emeryville, Calif.). For hESC-PLTs, culture media containing hESC-PLTs were gently collected, apyrase (1 U/ml) and EDTA (5 mM) (Sigma-Aldrich, St Louis, Mo.) were added to prevent platelet activation. hESC-PLTs were enriched and washed as described above. Washed blood platelets and hESC-PLTs were incubated at 37° C. for 0.5-2 hours before functional assays.

Example 30

Platelet Spreading on Immobilized Fibrinogen and vWF

Chamber slides with microtiter wells (Nalgen Nunc, Rochester, N.Y.) were coated with 100 µg/mL fibrinogen or vWF (30 g/ml) (Sigma-Aldrich, St Louis, Mo.) in 0.1M NaHCO$_3$ (pH 8.3) at 4° C. overnight. Washed human blood platelets or hESC-PLTs (1×10$^7$/mL) were allowed to adhere and spread on fibrinogen coated wells at 37° C. for 90 minutes. In some experiments, platelets were preincubated with an integrin antagonist, RGDS peptide, for 5 minutes before loading. In other experiments, platelets were mixed with ADP (20 µM) or thrombin (1 U/ml) (Sigma-Aldrich, St Louis, Mo.), and immediately loaded onto fibrinogen or vWF coated wells. After washing with PBS buffer, cells were fixed, permeabilized, and stained with Alexa Fluor 568 phalloidin (Molecular Probes, Eugene, Oreg.), FITC conjugated anti-human CD41a antibody (Dako cytomation, Carpinteria, Calif.) and DAPI. Adherent platelets were viewed with an Olympus BX51 fluorescence microscope using a PlanApo lens at 100×/1.40 oil objective. Images were acquired using a QICAM Fast camera and processed with Q Capture version 5.1 software.

Example 31

Formation of Platelet Micro-Aggregates

Washed human blood platelets and hESC-PLTs were resuspended in modified Tyrode buffer and labeled with a PKH67 Green Fluorescent Cell Linker (10 μM, Sigma, St. Louis, Mo.). Human blood platelets ($6 \times 10^7$) were mixed with fluorescence-labeled human blood platelets ($3 \times 10^5$) or hESC-PLTs ($3 \times 10^5$) in a 450 μL cuvette (Chronolog, Havertown, Pa.), treated with thrombin (0.5 U/mL) and stirred at 1200 rpm at 37° C. to trigger platelet aggregation. In control experiments, platelets were preincubated with RGDS peptide at 37° C. for 5 minutes before addition of thrombin, and aggregation assay was performed as above. Platelet micro-aggregates in 50 μL buffer were spread onto a glass slide and visualized under an Olympus BX51 fluorescence microscope.

Example 32

PAC-1 Binding Assay

Human blood platelets or hESC-PLTs with or without thrombin stimulation (1 U/ml, incubation at room temperature for 20 minute) were stained with APC-conjugated CD41a, PE-conjugated CD42b and FITC-conjugated PAC-1 antibodies in modified Tyrode's buffer. The samples were then analyzed using FACSCalibur. Forward scatter and side scatter gating were determined using human blood platelets as controls. Flow cytometry data were analyzed using Cellquest or Flowjo software.

Example 33

Clot Formation and Retraction

Human blood platelets or hESC-PLTs (approx $1.5 \times 10^7$/ml) were resuspended in 50 μL platelet-depleted plasma in a siliconized glass tube (Kimble Chase, Vineland, N.J.). Thrombin (2 U/ml) and 10 mM $CaCl_2$ were added to the cells to induce clot formation and retraction. The clots were allowed to retract at 37° C. for 1 hour and photographed. Clots were embedded in Tissue-Tek OCT compound and Tissue-Tek Cryomolds (Sakura Finetek, Torrance, Calif.), and then frozen in dry ice. Clot sections in 10 μm were made using a cryostat microtome Microm HM 560 (Thermo Scientific, Kalamazoo, Mich.).

Slides were fixed with methanol/acetone (1:3) for 30 minutes, washed with PBS and permeabilized with 0.1% Triton X-100, 0.1 M Tris, 10 mM EGTA, 0.15 NaCl, 5 mM $MgCl_2$ and 1% bovine serum albumin (BSA), pH 7.5. After blocking with 5% BSA and washing, sections were immunostained with rabbit anti-human integrin αIIb (clone H-160) and mouse anti-human fibrin (clone UC45) antibodies (Santa Cruz Biotech, Santa Cruz, Calif.). Sections were then incubated for 1 h in 1:200 secondary anti-rabbit IgG conjugated to rhodamine and anti-mouse IgM conjugated with FITC antibodies (Jackson ImmunoResearch Lab). Images were taken as described above.

Example 34

Intravital Microscopy

Widefield, multi-channel intravital microscopy of the cremaster muscle microcirculation was performed as previously described[47;50]. Male mice were anesthetized by an intraperitoneal injection of ketamine (125 mg/kg, Bedford Laboratories, Bedford, Ohio) and xylazine (25 mg/kg, Akorn Inc., Decatur, Ill.). A tracheal tube was inserted and the mouse was placed on a thereto-controlled blanket (37° C.). To maintain anesthesia, the ketamine and xylazine solution, 50 μl, was administered every 30 minute through a cannulus placed in the jugular vein. Further, a cannulus filled with saline containing 10 U/ml heparin was placed in the femoral artery. After the scrotum was incised, the cremaster muscle was exteriorized onto an intravital microscopy tray. The muscle preparation was superfused with thermo-controlled (37° C.) and aerated (95% $N_2$, 5% $CO_2$) bicarbonate-buffered saline throughout the experiment.

The cremaster muscle arteriolar wall was injured by laser ablation using a Micropoint Laser System (Photonics Instruments, South Windsor, Conn.) as described previously[47]. The developing mouse platelet thrombus was monitored by infusion of Dylight 649-labeled anti-CD42 (Emfret Analytics, 0.05 μg/g body weight). One or two pulses were ablated on inside vessel wall to initiate platelet thrombus formation. Human blood platelets or hESC-PLTs labeled with calcein AM (Invitrogen), 50-100 μl ($5-10 \times 10^5$ platelets), were infused through a femoral artery cannulus right after the vessel injury. Multiple thrombi were studied in one mouse, with new thrombi formed along the upstream of earlier thrombi to avoid any contribution from thrombi generated earlier. The new thrombi were generated after the labeled human platelets previously infused were completely cleared. After generation of 2-3 thrombi, the labeled human platelets pretreated with ReoPro (Centocor), 20 μg for $2 \times 10^6$ human platelets in 200 μl, 50-100 μl, were infused after the vessel injury in the same mouse. Another 2-3 thrombi were generated. Human blood platelets and hESC-PLTs were studied in different mice. Microvessel data were obtained using an Olympus BX61WI microscope with a 60× objective. Digital images were captured with a high speed digital camera (Hamamatsu C9300) through an intensifier (Video Scope International, Dulles, Va.). Fluorescence images were analyzed using Slidebook v5.0 (Intelligent Imaging Innovations, Denver, Colo.). Fluorescence images were captured at exposure times of 10-100 millisecond and bright field images were captured with exposure times of 20 millisecond. Data were collected for 3 minute following vessel wall injury. To simplify the image analysis, the dynamic range of the intensity of each pseudocolor was binarized. The number of human platelets circulating in the microvessel and incorporated into the developing mouse platelet thrombus at the site of vessel injury was counted over 3 minute after vascular injury.

Example 35

Statistical Analysis

Data were statistically analyzed by Student t-test for comparison of two groups using GraphPad Prism (GraphPad Software). Differences were considered significant at $P<0.05$.

Example 36

Platelet Purification Method Using Density Centrifugation for Platelets Generated from Hemangioblasts Platelets from MK differentiation culture include particles that are CD41a negative. These particles can constitute up to 50% of the particles from MK differentiation culture and it is desirable to increase the purity of platelet preparations. Density centrifugation methods using mediums which preserve viability and morphological indensity, such as low viscosity Percoll medium, were used to separate the CD41a negative particles from the platelets. Human peripheral platelets, separated into a thin layer, were removed from the CD41a negative particles without abrogating the capacity for PAC-1 binding and integrin activation.

Various embodiments of the invention are described above in the Detailed Description. While these descriptions directly describe the above embodiments, it is understood that those skilled in the art may conceive modifications and/or variations to the specific embodiments shown and described herein. Any such modifications or variations that fall within the purview of this description are intended to be included therein as well. Unless specifically noted, it is the intention of the inventors that the words and phrases in the specification and claims be given the ordinary and accustomed meanings to those of ordinary skill in the applicable art(s).

The foregoing description of various embodiments of the invention known to the applicant at this time of filing the application has been presented and is intended for the purposes of illustration and description. The present description is not intended to be exhaustive nor limit the invention to the precise form disclosed and many modifications and variations are possible in the light of the above teachings. The embodiments described serve to explain the principles of the invention and its practical application and to enable others skilled in the art to utilize the invention in various embodiments and with various modifications as are suited to the particular use contemplated. Therefore, it is intended that the invention not be limited to the particular embodiments disclosed for carrying out the invention.

While particular embodiments of the present invention have been shown and described, it will be obvious to those skilled in the art that, based upon the teachings herein, changes and modifications may be made without departing from this invention and its broader aspects and, therefore, the appended claims are to encompass within their scope all such changes and modifications as are within the true spirit and scope of this invention. It will be understood by those within the art that, in general, terms used herein are generally intended as "open" terms (e.g., the term "including" should be interpreted as "including but not limited to," the term "having" should be interpreted as "having at least," the term "includes" should be interpreted as "includes but is not limited to," etc.).

REFERENCES

1. Guerriero R, Mattia G. Testa U et al. Stromal cell-derived factor 1 alpha increases polyploidization of megakaryocytes generated by human hematopoietic progenitor cells. Blood 2001; 97:2587-2595.
2. Matsunaga T, Tanaka 1, Kobune M et al. Ex vivo large-scale generation of human platelets from cord blood CD34+ cells. Stem Cells 2006; 24:2877-2887.
3. Kaufman D S, Hanson E T, Lewis R L, Auerbach R, Thomson J A. Hematopoietic colony-forming cells derived from human embryonic stem cells. Proc. Natl. Acad. Sci. U.S.A. 2001; 98.: 10716-10721.
4. Lu S-J, Li F, Vida L, Honig G R. CD34+CD38– hematopoietic precursors derived from human embryonic stem cells exhibit an embryonic gene expression pattern. Blood 2004; 103:4134-4141.
5. Chadwick K, Wang L, Li L et al. Cytokines and BMP-4 promote hematopoietic differentiation of human embryonic stem cells. Blood 2003 2003; 102:906-915.
6. Chang K H, Nelson A M, Cao H et al. Definitive-like erythroid cells derived from human embryonic stem cells coexpress high levels of embryonic and fetal globins with little or no adult globin. Blood 2006; 108:1515-1523.
7. Tian X, Morris J K, Linehan J L, Kaufman D S. Cytokine requirements differ for stroma and embryo id body-mediated hematopoiesis from human embryonic stem cells. Exp. Hematol. 2004; 32:1000-1009.
8. Vodyanik M A, Bork J A, Thomson J A, Slukvin I I. Human embryonic stem cell-derived CD34+ cells: efficient production in the coculture with OP9 stromal cells and analysis of lymphohematopoietic potential. Blood 2005; 105:617-626.
9. Wang L, Menendez P, Shojaei F et al. Generation of hematopoietic repopulating cells from human embryonic stem cells independent of ectopic HOXB4 expression. J. Exp. Med. 2005; 201:1603-1614.
10. Woll P S, Martin C H, Miller J S, Kaufman D S. Human embryonic stem cell-derived NK cells acquire functional receptors and cytolytic activity. J. Immunol. 2005; 175: 5095-5103.
11. Zambidis E T, Peault B, Park T S, Bunz F, Civin C I. Hematopoietic differentiation of human embryonic stem cells progresses through sequential hematoendothelial, primitive, and definitive stages resembling human yolk sac development. Blood 2005; 106:860-870.
12. Qiu C, Hanson E, Olivier E et al. Differentiation of human embryonic stem cells into hematopoietic cells by coculture with human fetal liver cells recapitulates the globin switch that occurs early in development. Exp. Hematol. 2005; 33:1450-1458.
13. Zhan X, Dravid G, Ye Z et al. Functional antigen-presenting leucocytes derived from human embryonic stem cells in vitro. Lancet 2004; 364:163-171.
14. Ledran M H, Krassowska A, Armstrong L et al. Efficient hematopoietic differentiation of human embryonic stem cells on stromal cells derived from hematopoietic niches. Cell Stem Cell 2008; 3:85-98.
15. Gaur M, Kamata T, Wang S et al. Megakaryocytes derived from human embryonic stem cells: a genetically tractable system to study megakaryocytopoiesis and integrin function. J. Thromb. Haemost. 2006; 4:436-442.
16. Takayama N, Nishikii H, Usui J et al. Generation of functional platelets from human embryonic stem cells in vitro via ES-sacs, VEGF-promoted structures that concentrate hematopoietic progenitors. Blood 2008; 111: 5298-5306.

17. Lu S J, Feng Q, Caballero S et al. Generation of functional hemangioblasts from human embryonic stem cells. Nat. Methods 2007; 4:501-509.
18. Klimanskaya I, McMahon J. Approaches of derivation and maintenance of human ES cells: Detailed procedures and alternatives. In: Lanza Rea, ed. Handbook of Stem Cells. Volume 1: Embryonic Stem Cells. New York, USA: Elsevier/Academic Press; 2004:437-449.
19. Lu S J, Luo C, Holton K et al. Robust generation of hemangioblastic progenitors from human embryonic stem cells. Regen. Med. 2008; 3:693-704.
20. Lu S J, Feng Q, Park J S et al. Biologic properties and enucleation of red blood cells from human embryonic stem cells. Blood 2008; 112:4475-4484.
21. Fujiki H, Kimura T, Minamiguchi H et al. Role of human interleukin-9 as a megakaryocyte potentiator in culture. Exp. Hematol. 2002; 30:1373-1380.
22. Jeanpierre S, Nicolini F E, Kaniewski B et al. BMP4 regulation of human megakaryocytic differentiation is involved in thrombopoietin signaling. Blood 2008; 112:3154-3163.
23. Lordier L, Jalil A, Aurade F et al. Megakaryocyte endomitosis is a failure of late cytokinesis related to defects in the contractile ring and Rho/Rock signaling. Blood 2008; 112:3164-3174.
24. Chang Y, Aurade F, Larbret F et al. Proplatelet formation is regulated by the Rho/ROCK pathway. Blood 2007; 109:4229-4236.
25. Taguchi K, Saitoh M, Arai Y et al. Disparate effects of interleukin 11 and thrombopoietin on megakaryocytopoiesis in vitro. Cytokine 2001; 15:241-249.
26. Philipp C S, Remmler J, Zucker-Franklin D. The effects of Mpl-ligand, interleukin-6 and interleukin-11 on megakaryocyte and platelet alpha-granule proteins. Thromb. Haemost. 1998; 80:968-975.
27. Kanaji T. Russell S, Cunningham J et al. Megakaryocyte proliferation and ploidy regulated by the cytoplasmic tail of glycoprotein Ibalpha. Blood 2004; 104:3161-3168.
28. Santoso S, Kalb R, Kiefel V, Mueller-Eckhardt C. The presence of messenger RNA for HLA class I in human platelets and its capability for protein biosynthesis. Br. J. Haematol. 1993; 84:451-456.
29. Lalezari P, Driscoll A M. Ability of thrombocytes to acquire HLA specificity from plasma. Blood 1982; 59:167-170.
30. Sullenbarger B, Bahng J H, Gruner R, Kotov N, Lasky L C. Prolonged continuous in vitro human platelet production using three-dimensional scaffolds. Exp. Hematol. 2009; 37:101-110.
31. Giammona L M, Fuhrken P G, Papoutsakis E T, Miller W M. Nicotinamide (vitamin B3) increases the polyploidisation and proplatelet formation of cultured primary human megakaryocytes. Br. J. Haematol. 2006; 135:554-566.
32. Nagata Y, Yoshikawa J, Hashimoto A et al. Proplatelet formation of megakaryocytes is triggered by autocrine-synthesized estradiol. Genes Dev. 2003; 17:2864-2869.
33. Larson M K, Watson S P. Regulation of proplatelet formation and platelet release by integrin alpha IIb beta3. Blood 2006; 108:1509-1514.
34. Klimchenko O, Mori M, Distefano A et al. A common bipotent progenitor generates the erythroid and megakaryocyte lineages in embryonic stem cell-derived primitive hematopoiesis. Blood 2009; 114:1506-1517.
35. Nishikii H, Eto K, Tamura N et al. Metalloproteinase regulation improves in vitro generation of efficacious platelets from mouse embryonic stem cells. J. Exp. Med. 2008; 205:1917-1927.
36. Furie B, Furie B C. Mechanisms of thrombus formation. N. Engl. J. Med. 2008; 359: 938-949.
37. Day S M, Reeve J L, et al. Murine thrombosis models. Thromb. Haemost. 2004; 92: 486-494.
38. Sachs U J and Nieswandt B. In vivo thrombus formation in murine models. Circ. Res. 2007; 100: 979-991.
39. Furie B and Furie B C. In vivo thrombus formation. J. Thromb. Haemost. 2007; 5 Suppl 1: 12-17.
40. Junt T, Schulze H, et al. Dynamic visualization of thrombopoiesis within bone marrow. Science 2007; 317: 1767-1770.
41. Yu J, Hu J, et al. Human induced pluripotent stem cells free of vector and transgene sequences. Science 2009; 324: 797-801.
42. Takahashi K, Tanabe K, et al. Induction of pluripotent stem cells from adult human fibroblasts by defined factors. Cell 2007; 131: 861-872.
43. Yu J, Vodyanik M A. et al. Induced pluripotent stem cell lines derived from human somatic cells. Science 2007; 318: 1917-1920.
44. Kim D. Kim C H, et al. Generation of human induced pluripotent stem cells by direct delivery of reprogramming proteins. Cell Stem Cell 2009; 4: 472-476.
45. Ginsberg M H, Du X, Plow E F. Inside-out integrin signalling. Curr. Opin. Cell Biol. 1992; 4: 766-771.
46. Chen Y P, O'Toole T E, et al. A point mutation in the integrin beta 3 cytoplasmic domain (S752-->P) impairs bidirectional signaling through alpha IIb beta 3 (platelet glycoprotein M-IIIa). Blood 1994; 84: 1857-1865.
47. Cho J. Furie B C, et al. A critical role for extracellular protein disulfide isomerase during thrombus formation in mice. J. Clin. Invest 2008; 118: 1123-1131.
48. Coller B S. Anti-GPIIb/IIIa drugs: current strategies and future directions. Thromb. Haemost. 2001; 86: 427-443.
49. Cho J, Mosher D F. Enhancement of thrombogenesis by plasma fibronectin cross-linked to fibrin and assembled in platelet thrombi. Blood 2006: 107; 3555-3563.
50. Falati S, Gross P, et al. Real-time in vivo imaging of platelets, tissue factor and fibrin during arterial thrombus formation in the mouse. Nat. Med. 2002; 8: 1175-1181.
51. Reems J A, Pineault N, and Sun S. In vitro megakaryocyte production and platelet biogenesis: state of the art. Transfus. Med. Rev. 2010; 24: 33-43.
52. Chockalingam P, Sacher R A. Management of patients' refractory to platelet transfusion. J. Infus. Nurs. 2007; 30: 220-225.
53. Hod E, Schwartz J. Platelet transfusion refractoriness. Br. J. Haematol. 2008; 142: 348-360.
54. Tian X, Kaufman D S. Differentiation of embryonic stem cells towards hematopoietic cells: progress and pitfalls. Curr. Opin. Hematol. 2008; 15: 312-318.
55. Wang L, Menendez P, et al. Generation of hematopoietic repopulating cells from human embryonic stem cells independent of ectopic HOXB4 expression. J. Exp. Med. 2005; 201: 1603-1614.

What is claimed is:
1. A method of generating mature human megakaryocytes (MKs), comprising:
(i) providing human hemangioblasts, wherein the human hemangioblasts are CD34$^-$ CD31$^-$,

(ii) culturing the hemangioblasts of step (i) in the presence of TPO and SCF in serum-free conditions to differentiate the hemangioblasts into a population of immature human MKs; and (iii) further culturing the immature human MKs of step (ii) for 4-6 days to undergo endomitosis to obtain mature MKs.

2. The method of claim 1, wherein the hemangioblasts are differentiated in vitro from human pluripotent stem cells.

3. The method of claim 2, wherein the pluripotent stem cells are human embryonic stem cells (hESCs).

4. The method of claim 2, wherein the pluripotent stem cells are human induced pluripotent stem cells (iPSCs).

5. The method of claim 2, wherein the differentiation of pluripotent stem cells comprises dissociation of the pluripotent stem cells and culturing the pluripotent stem cells with medium comprising a growth factor or cytokine selected from the group consisting of BMP-4, VEGF, bFGF, TPO, Flt3 ligand, SCF and combinations thereof to form embryoid bodies (EBs).

6. The method of claim 5, wherein the medium comprises BMP-4 and VEGF and culturing the pluripotent stem cells is for about 48 hours to form the EBs.

7. The method of claim 6, wherein the concentration of BMP-4 is about 50 ng/ml and VEGF is about 50 ng/ml.

8. The method of claim 5, wherein the formed EBs are chemically and/or mechanically dissociated and at least a portion of the culture medium is replaced with medium comprising a growth factor or cytokine selected from the group consisting of BMP-4, VEGF, bFGF, TPO, Flt3 ligand, SCF and combinations thereof to generate the hemangioblasts.

9. The method of claim 8, wherein the concentration of bFGF is about 20 ng/ml, TPO is about 50-100 ng/ml, Flt3 ligand is about 50 ng/ml and SCF is about 50 ng/ml.

10. The method of claim 8, wherein the dissociated EBs are cultured in blast colony growth medium comprising bFGF for about 3 to 4 days to generate the hemangioblasts.

11. The method of claim 8, wherein the medium further comprises IL6, estradiol, vitamin B3, one or more extracellular matrix protein or combinations thereof.

12. The method of claim 4, wherein iPSCs are induced from somatic cells of human origin.

13. The method of claim 12, wherein the somatic cells are from adult or fetal tissue.

14. The method of claim 1, wherein differentiation of the hemangioblasts into the MKs comprises culturing in medium comprising TPO, SCF, and IL11.

15. The method of claim 14, wherein the concentration of TPO is about 50 ng/ml, SCF is about 20 ng/ml and IL11 is about 20 ng/ml.

16. The method of claim 14, further comprising replacing at least a portion of the culture medium with medium comprising TPO, SCF, and IL11 every 2 to 3 days to differentiate the hemangioblasts into the MKs.

17. The method of claim 1, wherein the hemangioblasts are $KDR^-$.

* * * * *